(12) United States Patent  
Kjellbom et al.

(10) Patent No.: US 7,919,587 B2  
(45) Date of Patent: Apr. 5, 2011

(54) ISOLATED AQUAPORIN IN ITS CLOSED CONFORMATION

(75) Inventors: Per Kjellbom, Lund (SE); Kristina Hedfalk, Göteborg (SE); Susanna Törnroth, Göteborg (SE); Maria Ekerot, Lund (SE); Urban Johansson, Lund (SE); Richard Neutze, Västra Frölunda (SE)

(73) Assignee: Hydrogene Lund AB, Lund (SE)

( * ) Notice: Subject to any disclaimer, the term of this patent is extended or adjusted under 35 U.S.C. 154(b) by 0 days.

(21) Appl. No.: 12/066,152

(22) PCT Filed: Sep. 8, 2006

(86) PCT No.: PCT/SE2006/001036  
§ 371 (c)(1),  
(2), (4) Date: May 15, 2009

(87) PCT Pub. No.: WO2007/030071  
PCT Pub. Date: Mar. 15, 2007

(65) Prior Publication Data  
US 2009/0312525 A1    Dec. 17, 2009

Related U.S. Application Data

(60) Provisional application No. 60/717,582, filed on Sep. 15, 2005.

(30) Foreign Application Priority Data

Sep. 9, 2005 (SE) .................................. 0501999

(51) Int. Cl.  
*C07K 14/00* (2006.01)  
*A23J 1/00* (2006.01)

(52) U.S. Cl. ........................................ 530/350; 530/412

(58) Field of Classification Search .................... None  
See application file for complete search history.

(56) References Cited

U.S. PATENT DOCUMENTS 5,741,671 A    4/1998    Agre  
5,763,263 A    6/1998    Dehlinger  
6,313,376 B1   11/2001   Jung et al.

OTHER PUBLICATIONS

Wiencek, J. M. "New Strategies for Protein Crystal Growth" Ann. Rev. Biomed. Eng. 1999, 1, 505-534.*  
Martinez-Ballesta et al. "Different blocking effects of $HgCl_2$ and NaCl on aquaporins of pepper plants." *Journal of Plant Physiology*. vol. 160. 2003. pp. 1487-1492.

(Continued)

*Primary Examiner* — Nashaat T Nashed  
(74) *Attorney, Agent, or Firm* — Merchant & Gould P.C.

(57) ABSTRACT

The invention relates to an isolated aquaporin having a bound ligand, wherein said ligand close the conformation of said aquaporin and inhibit and/or reduce water transport of said aquaporin, and/or a high resolution structure of an isolated aquaporin in a closed conformation characterized by the coordinates deposited at the Protein Data Bank ID:1Z98 and as set forth in Appendix 1, a crystal of said isolated aquaporin as well as the coordinates defining said crystal and the use of said aquaporin, and the use of the high-resolution structure as defined by the coordinates deposited at PDB ID:1Z98 and as set forth in Appendix 1, and a method to produce said aquaporin.

3 Claims, 8 Drawing Sheets  
(1 of 8 Drawing Sheet(s) Filed in Color)

OTHER PUBLICATIONS

Ren et al. "Polymorphism in packing of Aquaporin-1 Tetramers in 2-D Crystals." *Journal of Structural Biology*. vol. 130. 2000. pp. 45-53.

Wan et al. "Gating of water channels (aquaporins) in cortical cells of young corn roots by mechanical stimuli (pressure pulses): effect of ABA and of HgCl$_2$." *J. of Exp. Botany*. vol. 55. No. 396. 2004. pp. 411-422.

Agre et al. "Aquaporin water channels: molecular mechanisms for human diseases." *FEBS Letters*. vol. 555. 2003. pp. 72-78.

Bacon et al. "Docking by Least-squares Fitting of Molecular Surface Patterns." *J. Mol. Biol*. vol. 225. 1992. pp. 849-858.

Bailey. "The CCP4 Suite: Programs for Protien Crystallography." *Acta Cryst*. vol. D50. 1994. pp. 760-763.

Bartlet et al. "CAVEAT: A Program to Facilitate the Structure-derived Design of Biologically Active Molecules." *CAVET: Design of Biologically Active Molecules*. pp. 182-196.

Berendsen et al. "GROMACS: A message-passage parallel molecular dynamics implementation." *Computer Physics Communications*. vol. 91. 1995. pp. 43-56.

Brunger et al. "Crystallography & NMR System: A New Software Suite for Macromolecular Structure Determination." *Acta Cryst*. vol. D54. 1998. pp. 905-921.

Castle. "Aquaporins as targets for drug discovery." *DDT*. vol. 10. No. 7. 2005. pp. 485-493.

De Groot et al. "Water Permeation Across Biological Membranes: Mechanism and Dynamics of Aquaporin-1 and GlpF." www.sciencemag.org. *Science*. vol. 294. 2001. pp. 2352-2357.

Fu et al. "Structure of Clycerol-Conducting Channel and the Basis for Its Selectivity." www.sciencemag.org. *Science*. vol. 290. 2000. pp. 481-486.

Gonen et al. "Aquaporin-O membrane junctions revel the structure of a closed water pore." *Nature*. vol. 429. 2004. pp. 193-197.

Goodsell et al. "Automated Docking of Substrates to Proteins by Simulated Annealing." *Proteins: Structure, Function and Genetics*. vol. 8. 1990. pp. 195-202.

Gorelick et al. "Aquaporin-II: A channel protein lacking apparent transport function expressed in brain." *BMC Biochemistry*. vol. 7. 2006. pp. 1-14.

Han et al. "Water Transport in AQP0 Aquaporin: Molecular Dynamics Studies." *J. Mol. Biol*. vol. 360. 2006. pp. 285-296.

Harries et al. "The channel architecture of aquaporin 0 at a 2.2-A resolution." *PNAS*. vol. 101. No. 39. 2004. pp. 14045-14050.

Humphrey et al. "VMD: Visual Molecular Dynamics." *J. of Molecular Graphics*. vol. 14. 1996. pp. 33-38.

Ishibashi et al. "Cloning and Functional Expression of Second New Aquaporin Abundantly Expressed in Testis." *Biochemical and Biophysical Research Communications*. vol. 237. 1997. pp. 714-718.

Ishibashi et al. "Cloning and Identification of a new member of water channel (AQP10) as an aquaglyceroporin." *Biocimica et Biophysica Acta*. vol. 1576. 2002 pp. 335-340.

Johanson et al. The Complete Set of Genes Encoding Major Intrinsic Proteins in Arabidopsis Provides a Framework for a New Nomenclature for Major Intrinsic Proteins in Plants. *Plant Physiology*. vol. 126. 2001. pp. 1358-1369.

Johansson et al. "The Major Integral Proteins of Spinach Leaf Plasma Membranes are Putative Aquaporins and Are Phosphorylated in Response to Ca$^{2+}$and Apoplastic Water Potential." *The Plant Cell*. vol. 8. 1996. pp. 1181-1191.

Johansson et al. "The role of aquaporins in cellular and whole plant water balance." *Biochemica et Biophysica Acta*. vol. 1465. 2000. pp. 324-342.

Johansson et al. "Water Transport Activity of the Plasma Membrane Aquaporin PM28A Is Regulated by Phosphorylation." *The Plant Cell*. vol. 10. 1998. pp. 451-459.

Jones et al. "Improved Methods for Building Protein Models in Electron Density Maps and the Locations of Errors in these Models." *Acta Cryst*. vol. A47. 1991. pp. 110-119.

Jung et al. "Molecular Structures of the Water Channel through Aquaporin CHIP." *J. of Bio. Chem*. vol. 209. No. 20. 1994. pp. 14648-14654.

Karlsson et al. "Reconstitution of water channel function of an aquaporin overexpressed and purified from *Pichia pastoris*." *FEBS Letters*. vol. 537. 2003. pp. 68-72.

King et al. "From Structure to Disease the Evolving Tale of Aquaporin Biology." *Nature Reviews*. vol. 5. 2204. pp. 687-698.

Kondo et al. "Human aquaporin adipose (AQPap) gene: Genomic structure, promoter analysis and functional mutation." *Eur. J. Biochem*. vol. 269. 2002. pp. 1814-1826.

Kukulski et al. "The 5 A Structure of Heterologously Expressed Plant Aquaporin SoPIP2;1." *J. Mol. Biol*. vol. 350. 2005. pp. 611-616.

Kuntz et al. "A Geometric Approach to Macromolecule-Ligand Interations." *J. Mol. Biol*. vol. 161. 1982. pp. 269-288.

Kuriyama et al. "Molecular Cloning and Expression of a Novel Human Aquaporin from Adipose Tissue with Glycerol Permeability." *Biocehmical and Biophysical Research Communications*. vol. 241. 1997. pp. 53-58.

Laskowski et al. "Aqua and Procheck-NMR: Programs for checking the quality of protein structures solved by NMR." *J. of Biomolecular NMR*. vol. 8. 1996. pp. 477-486.

Ma et al. "cDNA Cloning and Gene Structure of a Novel Water Channel Expressed Exclusively in Human Kidney: Evidence for a Gene Cluster of Aquaporins at Chromosome Locus 12q13." *Genomics*. vol. 35. 1996. pp. 543-550.

Madsen et al. "Interactive motif and fold recognition in protein structures." *J. of Applied Crystallography*. vol. 35. 2002. pp. 137-139.

Martin et al. "3D Database Searching in Drug Design." *J. of Medicinal Chemistry*. vol. 35. No. 12. 1992. pp. 2146-2154.

Miranker et al. "Functionality Maps of Binding Sites: A Multiple Copy Simultaneous Search Method." *Proteins: Structure, Function and Genetics*. vol. 11. 1991. pp. 29-34.

Morishita et al. "Molecular Mechanism and Drug Development in Aquaporin Water Channel Diseases: Aquaporin Superfamily (Superaquaporins): Expansion of Aquaporins Restricted to Multicellular Organisms." *J. Pharmacol Sci*. vol. 96. 2004. pp. 276-279.

Morris et al. "ARP/wARP and Automatic Interpretation of Protein Electron Density Maps." *Methods in Enzymology*. vol. 374. 2003. pp. 229-244.

Murata et al. "Structural determinants of water permeation through aquaporin-1." *Nature*. vol. 407. 2000. pp. 599-605.

Preston et al. "Appearnce of Water Channels in Xenopus Oocytes Expressing Red Cell CHIP28 Protein." *Science*. vol. 256. 1992. pp. 385-387.

Saadoun et al. "Impairment of angiogenesis and cell migration by targeted aquaporin-1 gene disruption." *Nature*. vol. 434. 2005. pp. 786-791.

Savage et al. "Architecture and Selectivity in Aquaporins 2.5: A X-Ray Structure of Aquaporin Z." *PLoS Biology*. vol. 1. pp. 334-340.

Smart et al. "The Pore Dimensions of Gramicidin A." *Biophysical Journal*. vol. 65. 1993. pp. 2455-2460.

Sui et al. "Structural basis of water-specific transport through the AQP1 water channel." *Nature*. vol. 414. 2001. pp. 872-878.

Tamas et al. "A Short Regulatory Domain Restricts Flycerol Transport through Yeast Fpslp." *J. of Biological Chemistry*. vol. 278. No. 8. 2003. pp. 6337-6345.

Tornroth-Horsefield et al. "Structural mechanism of plant aquaporin gating." *Nature*. vol. 439. 2006. pp. 688-694.

Tournaire-Roux et al. "Cytosolic pH regulates root water transport during anoxic stress through gating of aquaporins." *Nature*. vol. 425. 2003. pp. 393-397.

Yang et al. "Water and Glycerol Permeabilities of Aquaporins 1-5 and MIP Determined Quantitatively by Expression of Epitope-tagged Constructs in Xenopus Oocytes." *J. of Biological Chemistry*. vol. 272. No. 26. 1997. pp. 16140-16146.

Yasui et al. "Molecular Mechanisms and Drug Development in Aquaporin Water Channel Diseases: Structure and Function Aquaporins." *J. Pharmacol Sci*. vol. 96. 2004. pp. 260-263.

Zelenina et al. "Copper Inhibits the Water and Glycerol Permeability of Aquaporin-3." *J. of Biological Chemistry*. vol. 279. No. 50. 2004. pp. 51939-51943.

Zelenina et al. "Nickel and Extracellular Acidification Inhibit the Water Permeability of Human Aquaporin-3 in Lung Epithelial Cells." *J. of Biological Chemistry*. vol. 278. No. 32. 2003. pp. 30037-30043.

* cited by examiner

|  | SEQ ID NO: | N terminal | Loop B | Loop D | C terminal |
|---|---|---|---|---|---|
| AtNIP7;1 | 85 | CLPYDI | FGGFP..WSQ | HCGPHQN..... | .PVSPSVSSLLR. |
| ZmNIP3;1 | 86 | VEIPAP | LRHFP..WLQ | ATDTRA..... | .RTQRSFRR... |
| AtSIP1;1 | 87 | ...... | AGVPGDTLFS | LRGPRR..... | .PQRKKQKKA |
| AtSIP1;2 | 88 | ...... | AGVSSDSLFS | LRGPRK..LLAKTFL | .LVQKKQKKA |
| ZmSIP1;1 | 89 | ..MA.. | AGLDSPSLFS | VKGPRN..VILKTFL | .PKPKTKKA |
| ZmSIP1;2 | 90 | ..MA.. | AGVTSPSLFS | VKGPRN..PIIKTWM | .PKPKAKKA |
| AtSIP2;1 | 91 | ...... | SGGFSSFIFS | RKIPGS..FFMKTWI | ..EEQEKPKAKSE |

US 7,919,587 B2

ISOLATED AQUAPORIN IN ITS CLOSED CONFORMATION

FIELD OF THE INVENTION

The invention relates to an isolated aquaporin having a bound ligand, wherein said ligand closes the conformation of said aquaporin and inhibit and/or reduce water transport of said aquaporin, and/or a high resolution structure of an isolated aquaporin in a closed conformation characterised by the coordinates deposited at the Protein Data Bank ID:1Z98 and as set forth in Appendix 1, a crystal of said isolated aquaporin as well as the coordinates defining said crystal and the use of said aquaporin, the use of the high-resolution structure as defined by the coordinates deposited at PDB ID:1Z98 and as set forth in Appendix 1, and a method to produce said aquaporin.

BACKGROUND OF INVENTION

Water is the medium of life. Since biological membranes have only limited intrinsic water permeability cells maintain the flux of water into and out of the cell via a family of water-specific, membrane protein channels called aquaporins (1). Members of the aquaporin family are found in archea, eubacteria and eukaryotes, including fungi, animals and plants. They serve an astonishing variety of physiological functions (5-7) and are easily identified by sequence similarity across all kingdoms of life. In higher eukaryotes, water transport activity of aquaporins is frequently regulated by phosphorylation, pH and osmolarity (6-8). Aquaporins in plants and animals are highly conserved and form large protein families with 35 members in higher plants (9) and 13 members in humans (5,10).

Based upon phylogenetic analyses, plant aquaporins are further divided into four subfamilies and their presence in primitive plants such as the bryophyte *Physcomitrella patens* implies that this specialization was already present in an ancient plant-ancestor (11). There are 13 remarkably conserved plasma membrane aquaporins (Plasma membrane Intrinsic Proteins or PIPs) which are all regulated, and these further separate into two distinct phylogenetic groups (PIP1 and PIP2).

Closure of the plant aquaporin SoPIP2;1 of spinach (formerly called PM28A (2)) has been reported to be triggered by the dephosphorylation of two serine residues: Ser115 in the cytosolic loop B (conserved as Ser in 12, and as Thr in 1, of the 13 *Arabidopsis* PIPs) and Ser274 in the C-terminal region (2,3) (conserved as Ser in 7, and as Thr in 1, of the 8 *Arabidopsis* PIP2s). Both residues are situated in consensus phosphorylation sites. Furthermore, the simultaneous closure of all *Arabidopsis* PIPs upon anoxia was recently reported to depend upon the protonation of a strictly conserved histidine residue in loop D (4), which corresponds to His193 in SoPIP2;1 (SEQ ID NO: 33). It is an intriguing observation that distinct chemical signals acting on residues well separated in sequence induces an identical physiological response within PIPs. While a number of structures have been reported for water (12-16) and glycerol (17) channels, no plant aquaporin structure has yet been determined at high resolution. Gonen et al. (15) reports a low-resolution structure of AQP0. At this resolution (3 Å) water molecules cannot be seen and the authors are not able to conclude that the structure represents a closed aquaporin. This is also clearly stated by the authors in the article (p 194-195: "We note, however, that our resolution is currently limited to 3 Å, and even if a pore appears to be in a closed conformation, it might still be permeable to solutes."). Furthermore, a high-resolution structure of AQP0 (16) with an open conformation show no global change in the structure as compared to the low-resolution AQP0 structure reported in ref 15. Thus, it is likely that the structure in ref 15 represents an open aquaporin. Recently an additional report (35) arrives at the same conclusion that the structure of AQP0 reported in ref 15, as well as in ref 16, is open and not closed to water transport.

In addition, the low-resolution structure of AQP0 presented in Gonen et al. (15) is based on a proteolytically cleaved AQP0. Thus, both the N- and C-terminal regions of the protein are cleaved off and can therefore not participate in closing the pore (36). Kukulski et al. (37) depicts a 5 Å low-resolution structure of an aquaporin that in a previous publication by the same authors had been shown to be open (28). However, from a 5 Å low-resolution structure it is impossible to see if the pore is open or closed.

Furthermore, no gating mechanisms have been unambiguously demonstrated. Therefore it is crucial to establish the atomic structure of an aquaporin in its closed formation. Structural information of the closed conformation is necessary for understanding the mechanism of gating and for structure-based design and development of organic compounds, peptides or antibodies that either stabilize the open conformation or the closed conformation. By obtaining the structure of a closed aquaporin it will for the first time be possible to use that particular structure to modify the gating. This can in plants be done by direct genetic engineering of aquaporins in order to improve stress tolerance, e.g. against drought stress. In mammalian species pharmaceutical compounds that stabilize the closed or the open conformation of aquaporins can be designed based on the closed conformation of the aquaporin SoPIP2;1 (SEQ ID NO: 33) from the plasma membrane of the plant spinach. Such inhibitors and activators are candidate pharmaceutical and cosmeceutical compounds, e.g. antiperspirants. Aquaporins are also important for cell migration during angiogenesis, wound healing, tumour spread and organ regeneration (27), processes that therefore can be modulated by pharmaceutical compounds interacting and modifying the gating of aquaporins. Dysfunction of human aquaporins is associated with clinically important diseases such as polyuria in kidney diseases. Conversely, increased water retention is associated with congestive heart failure, liver cirrhosis and nephritic syndrome. Also pathological skin conditions such as anhidrosis, hyperhidrosis and conditions where the transepidermal water loss is deviating from normal conditions could be targets for aquaporin inhibitors and activators. Moreover, brain edema, glaucoma and skin burns could be treated by inhibitors and activators of aquaporins. The cosmeceutical applications of aquaporin inhibitors and activators include not only antiperspirant but also dermatological conditions where one wants to influence the transepidermal water loss. The atomic structure of the closed conformation of SoPIP2;1 (SEQ ID NO: 33) can also be used for designing novel in silico and in vitro screening systems for pharmaceuticals and cosmeceuticals acting as modulators of aquaporin gating and function. Knowledge of the atomic structure of the closed conformation can also be used to design, and also to screen for, peptides and antibodies that interact with certain epitopes on aquaporins and thus effect activity and gating.

SUMMARY OF THE INVENTION

The object of the present invention is to solve the above, discussed problems in connection with aquaporins and the gating mechanism of aquaporins. This object is achieved by the present invention as specified below.

The object of the present invention, is the isolation and determination of the structure of an aquaporin and thereby enable the possibility to solve all the above mentioned problems.

The invention relates in one aspect to an isolated aquaporin having a bound ligand, wherein said ligand closes the conformation of said aquaporin and inhibit and/or reduce water transport of said aquaporin, and/or a high resolution structure of an isolated aquaporin in a closed conformation characterised by the coordinates deposited at the Protein Data Bank ID:1Z98 and as set forth in Appendix 1, a crystal of said isolated aquaporin as well as the coordinates defining said crystal and the use of said aquaporin, the use of the high-resolution structure as defined by the coordinates deposited at PDB ID:1Z98 and as set forth in Appendix 1, and a method to produce said aquaporin.

In a second aspect, the invention relates to a crystal of an isolated aquaporin in its closed conformation having an atomic structure characterised by the coordinates deposited at the Protein Data Bank ID:1Z98 and as set forth in Appendix 1.

In a third aspect the invention relates to a method of producing an isolated aquaporin having a closed conformation comprising the steps; providing said aquaporin, adding a ligand to said aquaporin; producing crystals and obtaining an aquaporin having a ligand bound to said aquaporin, wherein said ligand closes the conformation of said aquaporin and inhibit and/or reduce water transport through said aquaporin.

In a fourth aspect the invention relates to the use of said isolated aquaporins or said crystal of said aquaporin as well as the coordinates characterising said crystal.

In a final aspect the invention relates to the use of a ligand binding to the cytoplasmic side to close the conformation of an aquaporin.

Further advantages and objects with the present invention will be described in more detail, inter alia with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows sequence comparisons between selected aquaporins. Sequence comparisons between selected aquaporins from plants, animals and bacteria. SoPIP2;1 is indicated with an arrow and important conserved residues among PIPs or PIP2s are indicated at the top together with the number of the corresponding residue in SoPIP2;1. At, *Arabidopsis thaliana*, SEQ ID NO: 9, see also SEQ ID NOs: 10-13, 23-30, 53-55, 58-60, 64, 65, 68, 73-77, 81-85, 87, 88, and 91; Zm, *Zea mays*, SEQ ID NO: 3, see also SEQ ID NOs: 4-8, 16-22, 56, 57, 61-63, 66, 67, 69-72, 78-80, 86, 89, and 90; Pa, *Picea abies*, SEQ ID NO: 14, see also SEQ ID NO: 31; Pp, *Physcomitrella patens*, SEQ ID NOs: 15, see also SEQ ID NO: 32; So, *Spinacea oleracae*, SEQ ID NO: 33; Hs, *Homo sapiens*, SEQ ID NO: 34, see also SEQ ID NOs: 40-44, 46, 47, 49-52; Bt, *Bos taurus*, SEQ ID NO: 35, see also SEQ ID NO: 38; Gg, *Gallus gallus*, SEQ ID NO: 36, see also SEQ ID NO: 39; Xl, *Xenopus leavis*, SEQ ID NO: 37; Ec, *Escherichia coli*, SEQ ID NO: 45, see also SEQ ID NO: 48.

DETAILED DESCRIPTION OF THE INVENTION

Definitions

Figure 2:
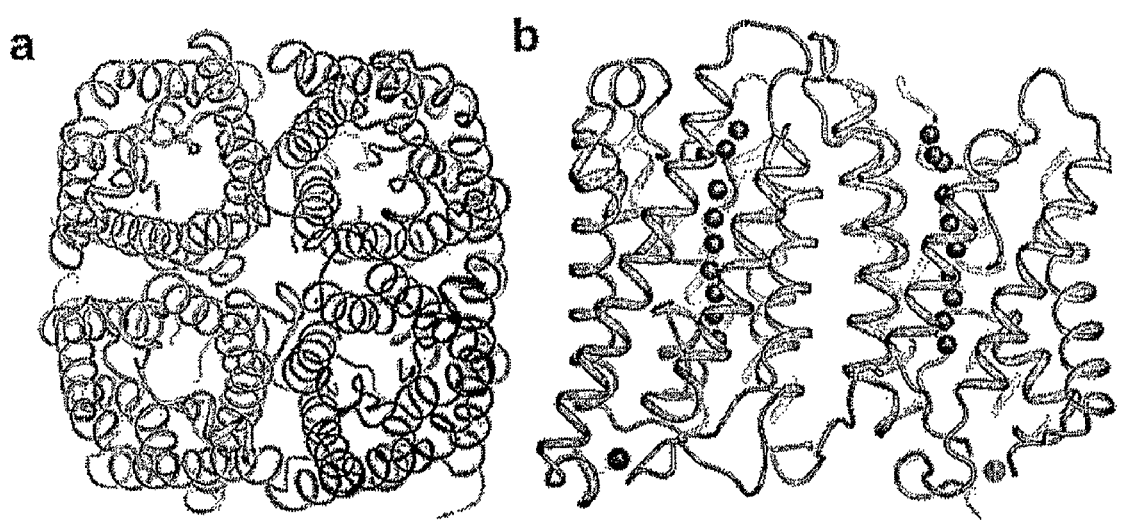
FIG. 2 shows structure of SoPIP2;1 tetramer. SoPIP2;1 tetramer viewed from the extracellular side (a) and two of the monomers viewed from the inside of the tetramer (b). The oxygens of water molecules and the $Cd^{2+}$ ion are indicated as spheres.

In the context of the present application and invention, the following definitions apply:

The term "pore diameter" is intended to mean the diameter at different positions within the pore of the aquaporin.

The term "closed conformation" refers to the structure of a closed aquaporin that do not permit the transfer of water molecules from one side of the water channel to the other side due to a too small pore diameter to allow water to pass The term "aquaporin" is intended to mean a membrane channel protein that facilitate the flux of water and/or other small solutes across biological membranes.

The term "gating mechanism" refers to the way the overall structure and the positions of the individual amino acids change when the aquaporin goes from an open to a closed conformation or visa versa.

The term "ligand" is intended to mean any molecule (or part of a molecule) that is bound or is able to bind selectively and stoichiometrically to one or more specific sites on another molecule, for example a protein. Examples of ligands are peptides, small molecules, $Cd^{2+}$, $Ca^{2+}$, $Mg^{2+}$, $Mn^{2+}$ or any other divalent cation.

The synonymous terms "high resolution" and "atomic resolution" are intended to mean the minimum distance two atoms can be separated from each other and still be seen as two atoms and being below 2.5 Å.

Figure 1A:
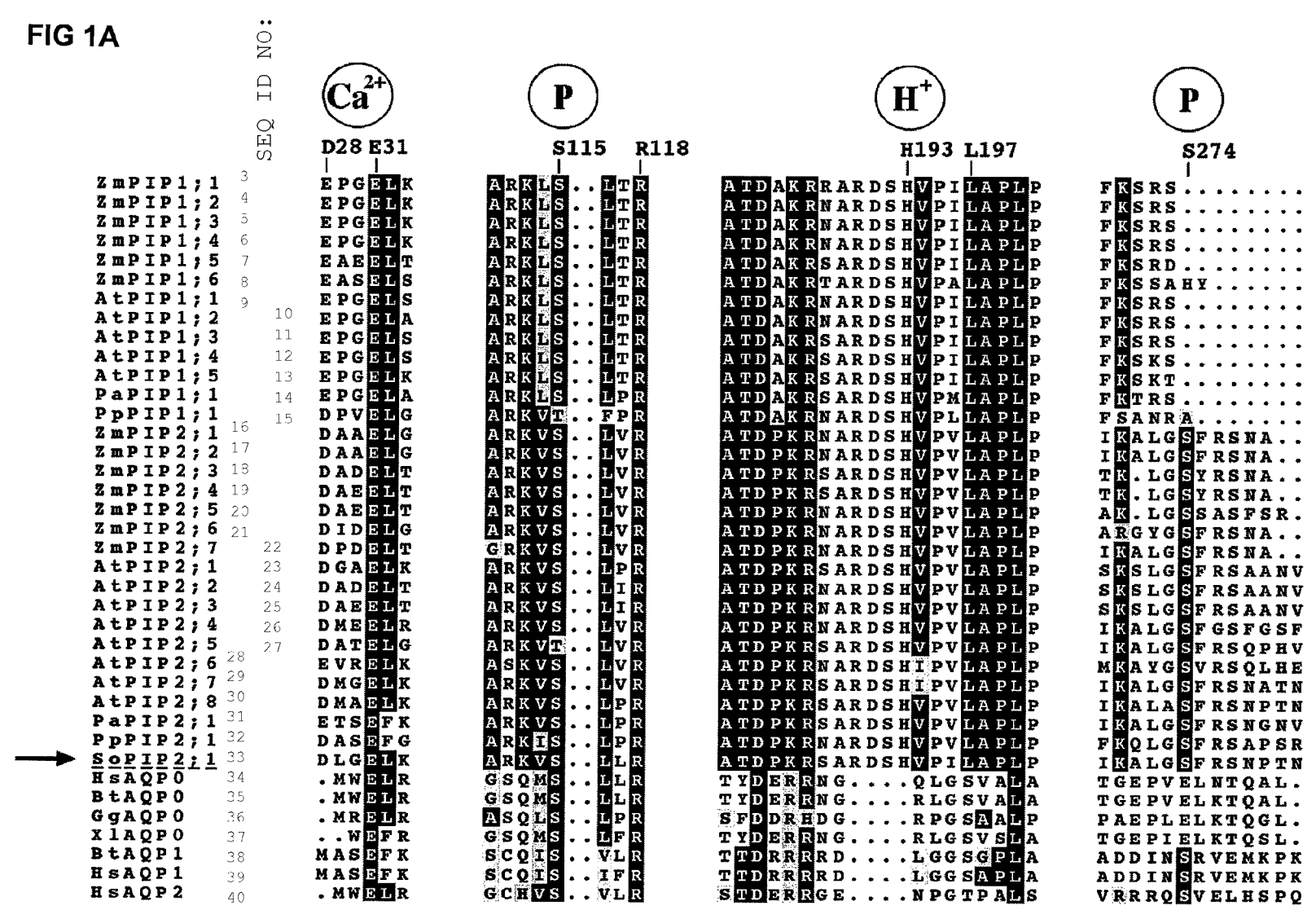

The term "D-loop" is intended to mean at least a stretch of amino acid residues being between the fourth and the fifth membrane spanning region of an aquaporin, in SoPIP2;1 represented by amino acid residues 182-201 (see, e.g., SEQ ID NO: 33), as shown in FIG. 1.

The term "homology modelling" is intended to mean a computational method for determining the structure of a protein based on its similarity to known structures. Given the amino acid sequence of an unknown structure and the solved structure of a homologous protein, each amino acid in the solved structure is mutated, computationally, into the corresponding amino acid from the unknown structure. The accuracy of structures determined by homology modelling depends largely on the degree of similarity between the unknown and the known protein sequence.

The term "atomic coordinates" or "structure coordinates" is intended to mean mathematical coordinates that describe the positions of atoms in crystals of the aquaporin. The diffraction data obtained from the crystals are used to calculate an electron density map of the repeating unit of the crystal. The electron density maps are used to establish the positions (i.e. coordinates X, Y, and Z) of the individual atoms within a single aquaporin. Those of skill in the art understand that a set of structure coordinates determined by X-ray crystallography is not without standard error. For the purpose of this invention, any set of structure coordinates for an aquaporin from any source has a root mean square deviation of non-hydrogen atoms of less than 0.75.ANG. when superimposed on the non-hydrogen atom positions of the said atomic coordinates deposited at the Research Collaboratory for Structural Bioinformatics (RCSB) Protein Data Bank (PDB) (Berman et al., 2000, Nucleic Acids Research, 28, 235-242) with the accession numbers PDB ID:1Z98 and as set forth in Appendix 1. Other examples of aquaporin structures are 1TM8, 1YMG, 1J4N, 1RC2 and 1FX8.

In the list of atomic coordinates set forth in Appendix 1 the term "atomic coordinate" refers to the measured position of an atom in the structure in Protein Data Bank (PDB) format, including X, Y, Z and B for each. The assembly of "atomic coordinate" also refers to "atomic coordinates" or "structure coordinates". The term "atom type" refers to the element whose coordinates are measured. The first letter in the column defines the element. The term "X, Y, Z" refers to the crystallographically defined atomic position of the element measured with respect to the chosen crystallographic origin. The term "B" refers to a thermal factor that measures the mean variation of an atom's position with respect to its average position.

The term "molecular modelling" or "molecular structural technique" is intended to mean the use of computers to draw realistic models of what molecules look like and to make predictions about structure activity relationships of ligands and other agents. The methods used in molecular modelling range from molecular graphics to computational chemistry.

The term "molecular dynamics simulations" is intended to mean computer simulations of the dynamic properties of a molecule such as conformational changes using e.g. the Gromacs simulation suite or VMD (Ref. Berendsen H. J. C., van der Spoel, D. and van Drunen, R., Comp Phys Commun 91, 43 (1995) and Humphrey, W., Dalke, A. &Schulten, K. VDM: visual molecular dynamics. J Mol Graph 14, 33-8 (1996).)

The terms "bind", "binding", "bond", "bonded", when used in reference to the association of "binding agents" such as atoms, molecules, chemical groups or ligands is intended to mean any physical contact or association of two or more atoms, molecules, or chemical groups (e.g., the binding of a ligand with a protein subunit refers to the physical contact between the ligand and the protein subunit). Such contacts and associations include covalent and non-covalent types of interactions.

An Aquaporin

In a first aspect, the invention relates to an isolated aquaporin having a bound ligand, wherein said ligand close the conformation of said aquaporin and inhibit and/or reduce water transport of said aquaporin, and/or a high resolution structure of an isolated aquaporin in a closed conformation characterised by the coordinates deposited at the Protein Data Bank ID:1Z98 and as set forth in Appendix 1. Examples of other aquaporins are those listed in FIG. 1, such as AQP0, 1, 2, 3, 4, 5, 6, 7, 8, 9, 10, 11, 12 or SoPIP2:1. Said ligand may be a ligand as defined above. Examples of ligands are $Cd^{2+}$, $Ca^{2+}$, $Mg^{2+}$, $Mn^{2+}$ or any other divalent cation. The ligand may be bound at different sites on the aquaporin, such as at the cytoplasmic side. The ligand may for example be a non-covalently bound ligand. The ligand bound closed conformation can be defined by a structure at high resolution. By determination of the structure of an isolated and crystallized aquaporin, a closed aquaporin conformation was obtained for the first time at atomic resolution. This enabled the possibility to deduce the gating mechanism of an aquaporin for the first time. The structure of such a closed aquaporin will enable the possibility to design new pharmaceutical (e.g., diuretics and inhibitors of angiogenesis) and cosmeceutical (e.g., antiperspirants) compounds that either stabilize the closed conformation or the open conformation. Since aquaporins are evolutionary very well conserved all the way from bacteria to plants and mammals, such compounds can be effective on aquaporins in many or all species. The atomic structure of a closed aquaporin such as SoPIP2;1 can also be used for structure based drug design and also for designing screening methods, both in silico and in vitro, for identifying inhibitors and activators of aquaporins. By obtaining the structure of a closed aquaporin and then using that particular structure it will be possible by genetic engineering to modify the gating and functioning of plant aquaporins, and to generate new plant varieties with improved stress tolerance against drought.

Furthermore, the invention relates to an aquaporin having a pore diameter of around 2.1 Å at the constriction region and less than that in the pore towards the cytosolic vestibule when the aquaporin is closed. The pore diameter is defined by the boundaries of the water conducting pore. The pore diameter may be measured by the use of a program such as the HOLE program described by Smart et al., Biophys J 65, 2455-2460 (1993). The structure was determined using a crystallised form of an aquaporin wherein the aquaporin prior to crystallisation was produced in Pichia pastoris, i.e., overproduction of a heterologous eukaryotic protein as described below under the Examples. The structure was solved at 2.1 Å resolution.

Figure 3:
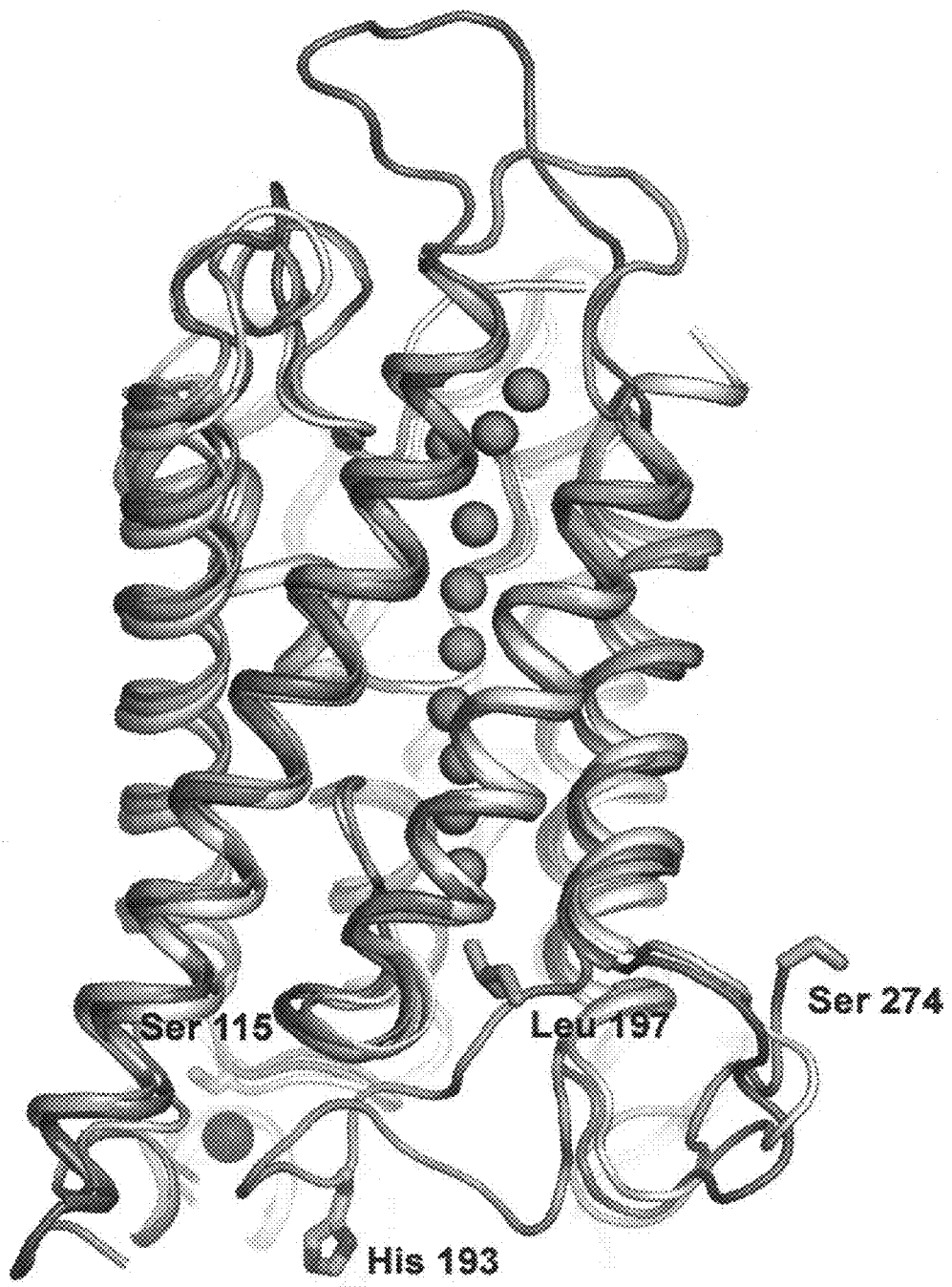
FIG. 3 shows structural comparisons of eukaryotic aquaporins. Overlay of AQP0, AQP1 and SoPIP2;1. The D-loop with His193 and Leu 197 (SEQ ID NO: 33) is blocking the pore in SoPIP2;1 whereas the D-loops of AQP0 and AQP1 are occupying the same space as the C-terminal region in SoPIP2;1 ending with Ser274 (SEQ ID NO: 33). The $Cd^{2+}$ ion is indicated by the sphere at the lower left side of the figure.
Figure 5:
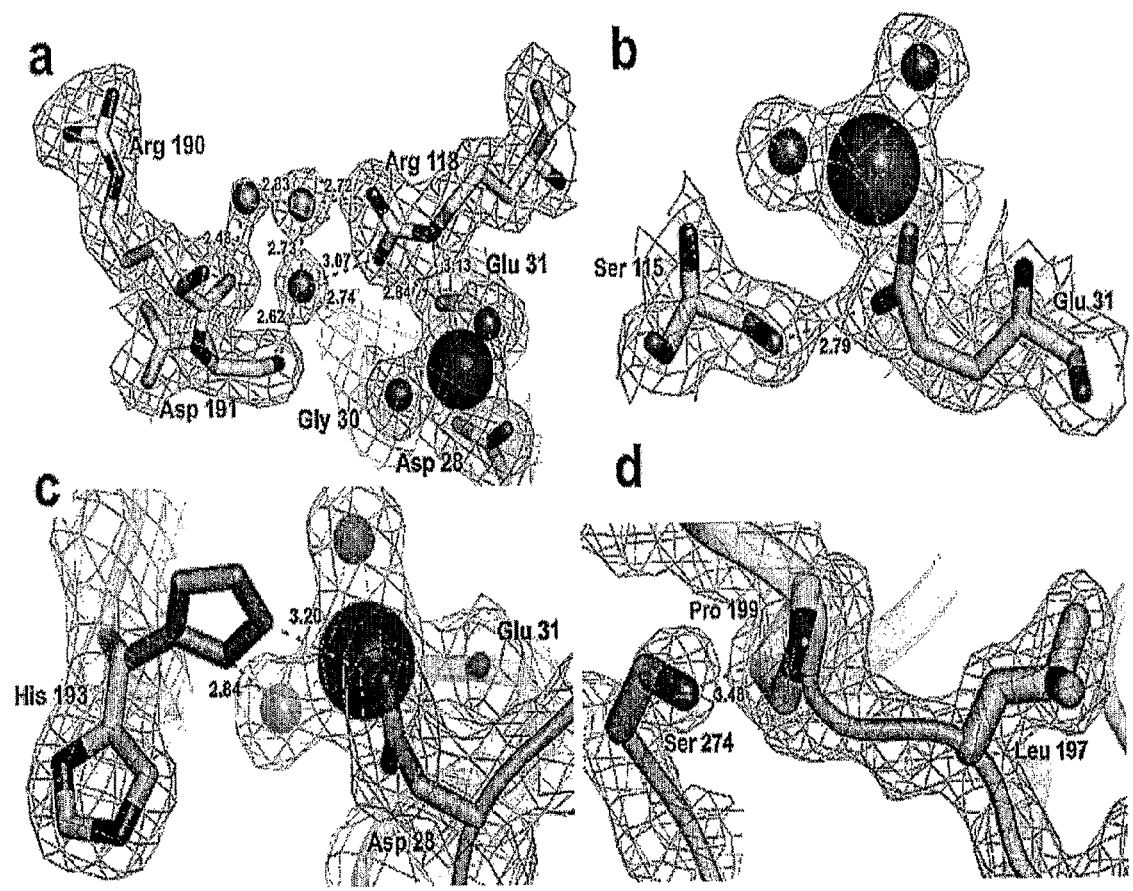
FIG. 5 shows electron density at the sites of regulation of SoPIP2;1 by phosphorylation and pH. Electron density at the sites of regulation by phosphorylation and pH for SoPIP2;1. a, Close up view of the divalent cation binding site showing the location of the $Cd^{2+}$ ion and the network of H-bonds linking Gly30 and Glu31 via Arg118 to Arg190 and Asp191 (SEQ ID NO: 33) of loop D. b, Close up view of the phosphorylation residue Ser115 illustrating its H-bond to Glu31 (SEQ ID NO: 33). c, Close up view of His193 (SEQ ID NO: 33). When protonated an alternate conformation for His 193 may be adopted which forms a salt bridge to Asp28 (SEQ ID NO: 33). d, Electron density for Ser274 which contacts Pro199 and Leu200 (SEQ ID NO: 33) of a neighboring monomer of the SoPIP2;1 tetramer. All $2F^{obs}$—$F^{calc}$ maps are contoured at 1.0σ.
Figure 6:
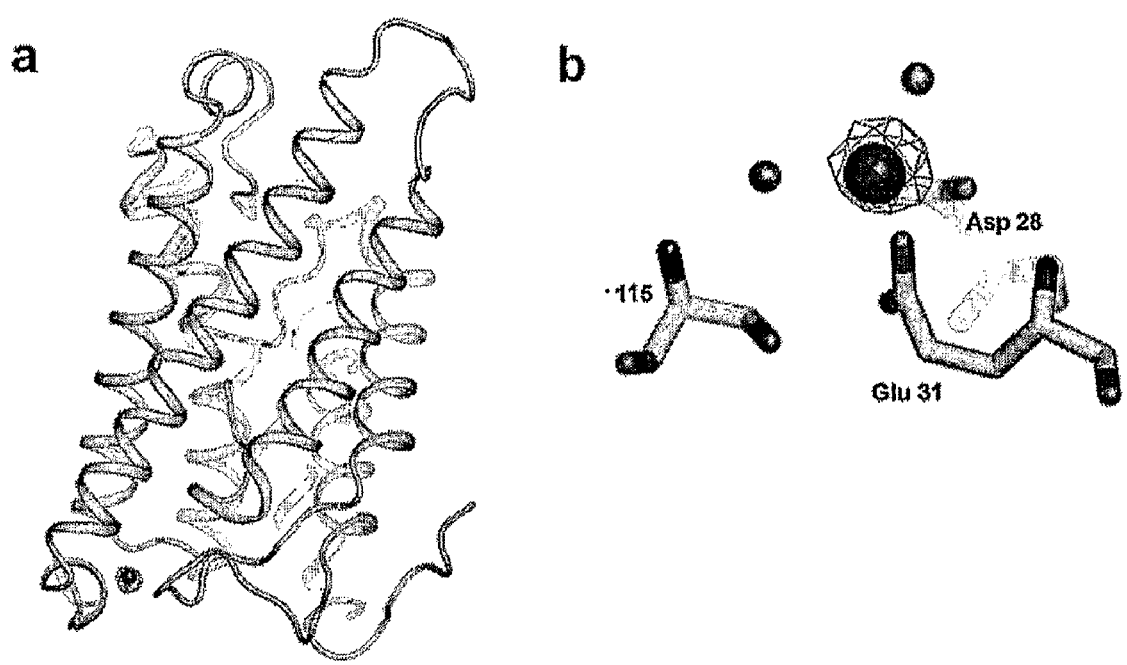
FIG. 6 shows difference anomalous density map for $Cd^{2+}$ ion. Difference anomalous density map illustrating the location of a single metal. a, Long distance view of the map. b, Close up view of the map near the assigned $Cd^{2+}$ binding site. This map is contoured at 5σ.

Additionally the aquaporin may be eukaryotic, such as selected from the group consisting of human, plant or animal aquaporins. Examples of plant species are spinach, sugar beet, Arabidopsis, maize, rice, wheat, barley, oats and mammalian species are human, bovine, sheep and other mammals, along with non-eukaryotic organisms such as yeast or bacteria. One specific example being the aquaporin from the plant spinach (SoPIP2;1, SEQ ID NO: 33), the present invention, was crystallised as a tetramer displaying extended hydrophobic interactions between monomers as shown in FIG. 2. By the use of the X-ray crystal structure of SoPIP2;1 and then overlay the X-ray structure with the structure of another aquaporins, such as the bovine AQP0 (16) and AQP1 (13) it was possible to identify that they had an identical structural core consistent with the "hour-glass model" (19), differing only by 0.8 Å r.m.s.d. on Cα atoms within the transmembrane regions (FIG. 3). SoPIP2;1, bovine AQP0 (16) and AQP1 (13). Likewise, the half-helices formed by loops B (cytosolic) and E (extracellular), with the Asn-Pro-Ala aquaporin signature motif at the N terminal ends, fold into the channel from opposite sides of the membrane and together create a seventh transmembrane region, which is perfectly preserved structurally. Seven water molecules are observed within the SoPIP2;1 channel (FIG. 3), revealing an unbroken water network stretching almost fully through the pore with a maximum distance of only 3.1 Å between each water. The D-loop of the aquaporin or parts thereof being involved in the closed conformation of the aquaporin. The D-loop or part thereof being involved in the gating mechanism like a door which opens and closes. A key residue in this respect is the fully conserved Leu197 (SEQ ID NO: 33) of loop D in SoPIP2;1, which inserts into a cavity near the entrance of the channel and, in combination with His99, Val104 and Leu108 (FIG. 4b, SEQ ID NO: 33), creates a hydrophobic barrier blocking the pore. Calculations of the channel width, using HOLE (23) establish that the pore narrows to a diameter of approximately 1.4 Å at Leu197 and narrows further to 0.8 Å near Pro195 and Val194 (FIG. SEQ ID NO: 33). This compares with the minimum pore diameter of 2.1 Å within the SoPIP2;1 constriction region (9) and is insufficient to allow the passage of water. Loop D and Leu197 (SEQ ID NO: 33) are also key to understanding the molecular mechanism of channel opening or closure in response to specific biochemical signals. In FIGS. 4b and c two water molecules separated by 6.4 Å are visible on either side of the hydrophobic barrier associated with Leu197, and one of these forms H-bonds to His99 and the main-chain oxygen of Pro 195 (SEQ ID NO: 33). Should a conformational change in loop D concomitantly displace Leu197, Pro195 and Val194 (SEQ ID NO: 33), then a pathway between these two water molecules extending into the cytosol would open. Analogy with the 2.1 Å pore-diameter of the constriction region implies that a displacement of these loop D residues by as little as 1.3 Å could be sufficient to open the channel. It has been postulated that divalent cations may play a role in aquaporin regulation (1, 2, 21) and inhibition (24,25). In FIGS. 2 and 3 a heavy-metal (FIG. 6 shows the anomalous difference density map) is observed near loop D and is assigned as $Cd^{2+}$ since the addition of this ion improved the crystal quality. $Cd^{2+}$ may be replaced by another divalent cation in vivo, and a search for similar structural motifs (26) revealed 13 PDB entries containing $Ca^{2+}$. As such, we postulate that this metal binding site likely binds $Ca^{2+}$ in vivo. This site is implicated in regulation since it serves to anchor loop D, through a network involving ionic interactions and H-bonds (FIG. 5a), onto a short α-helix of the N-terminus (FIG. 3) and thus appears to be critical for defining the unique conformation of loop D observed for SoPIP2;1. Specifically, Arg190 and Asp191 of loop D are connected to the side-chain of Arg118 (strictly conserved in PIPs) and Gly30 via a H-bond network containing three water molecules (SEQ ID NO: 33). Arg118 in turn forms H-bonds to Glu31 (strictly conserved in PIPs) which ligates the $Cd^{2+}$ ion (FIG. 5a, SEQ ID NO: 33). Significantly, the hydroxyl group of the conserved phosphorylation site Ser115 also forms a H-bond to Glu31 (FIG. 5b, SEQ ID NO: 33). It is therefore apparent that the covalent attachment of a phosphate group onto the hydroxyloxygen of Ser115 would significantly perturb the conformation of Glu31, which would result in disrupting the crucial water mediated H-bond network from Arg118 to Arg190 and Asp191 (FIG. 5a, SEQ ID NO: 33). We suggest that the disruption of this anchoring network would profoundly alter the conformation of loop D, and the resulting structural change would be sufficient to displace Leu197, Pro195 and Val194 (SEQ ID NO: 33) and thereby unplug the entrance into the aquaporin channel from the cytosol. It is even possible that this displacement may result in loop D adopting a conformation somewhat closer to that of AQP0 and AQP1 (FIG. 3).

Conversely, when Ser115 is phosphorylated and the water channel is open, the protonation of His193 (SEQ ID NO: 33) (strictly conserved) closes the channel (4). A mechanism for pH-regulated PIP gating also emerges from the structure of SoPIP2;1. In FIG. 5c the conformation of His193 (SEQ ID NO: 33) is shown. At low pH where His193 is protonated, a simple rotation of the histidine side-chain (FIG. 5c) would enable it to form a salt bridge to Asp28 (SEQ ID NO: 33) (conserved in PIPs as either Asp or Glu). In this manner the H-bond mediated anchor for loop D onto the N-terminus (FIG. 5a), which we suggest is lost upon Ser115 (SEQ ID NO: 33) phosphorylation, would be recovered. As such the structure of Ser115 (SEQ ID NO: 33) phosphorylated SoPIP2;1 at low pH can be expected to be similar to that reported here, with the cytosolic side of the aquaporin being capped by loop D and Leu197, Pro195 and Val194 (SEQ ID NO: 33) effectively blocking the water channel.

A structural framework for aquaporin regulation may also be proposed when considering the phosphorylation of Ser274 (SEQ ID NO: 33) (conserved in PIP2 homologues). In this case, however, Ser274 (SEQ ID NO: 33) is distant from the $Cd^{2+}$ site. Instead, Ser274 (SEQ ID NO: 33) is located in the C-terminal region, of SoPIP2;1 which extends towards the four-fold axis of the tetramer and interacts with the main-chain nitrogen of Pro199 (SEQ ID NO: 33) of an adjacent monomer (FIGS. 2b, 5d), which is the final residue of loop D. Should Ser274 (SEQ ID NO: 33) become phosphorylated then this interaction would be profoundly affected, and the creation of a cluster of four negative phosphate charges in close proximity should induce a significant conformational change in the C-terminal region. An interaction between Ser274 (SEQ ID NO: 33) of one monomer with residues in loop D of another monomer in the aquaporin tetramer also suggests an orchestrated regulation of the monomers within homotetramers.

The closed conformation of SoPIP2;1 (SEQ ID NO: 33) was crucial for discerning a gating mechanism and the positions of specific amino acids in the closed conformation, that previously biochemical and genetic experiments had identified as important for gating, immediately suggest how the closed structure can be stabilized and destabilized.

According to a second aspect, the invention relates to an aquaporin comprising an atomic structure characterised by the coordinates deposited at the Protein Data Bank ID:1Z98 and as set forth in Appendix 1 and to phases computed from the coordinates of said atomic structure deposited. A person skilled in the art can easily by the use of the deposited Protein Data Bank ID:1Z98 and as set forth in Appendix 1 in combination with one or more molecular structural technique, develop new aquaporins or binding agents such as inhibitors to aquaporins as well as modify the inhibitors.

The disclosed isolated aquaporin crystal structure of said aquaporin as well as the coordinates characterising said crystal may be used to screen for binding agents, or ligands, that stabilise and/or destabilise the closed conformation of said aquaporin or to create homology models of closed aquaporins. Other uses are to identify binding agents (ligands) or identification of at least one genetic modification capable of affecting the gating mechanism of said aquaporin, such as by an in silico technique. Another use is the development of genetically modified plants, such as agricultural plants.

Accordingly, water channels are functionally characterized by heterologous overexpression in *Xenopus laevis* oocytes. The method is described in detail in references 1 and 2. The oocytes have low intrinsic water permeability, allowing detection of any increase in water permeability due to the expressed aquaporin. In this system AQP1, 2, 3, 4, 5, 7, 8, 9 and 10 (see, e.g., SEQ ID NOs: 38-42 and 44) have high water permeabilities compared to AQP0, 6 and 11 (see, e.g., SEQ ID NOs: 34-37, 43, and 46) that are considered as poor water channels (Table 1; see also table 1 in Castle N A, Drug Discov. Today. 2005, 10, 485-93). AQPs with a high water permeability are primary targets for binding agents, ligands, that stabilize and/or destabilize a closed conformation since only a minor or no effect is expected by modulation of a poor or non-functional water channel.

TABLE 1

Water permeabilites for mammalian aquaporins and SoPIP2;1

| | Water permeability[a] | $P_f$-values ($\mu$m/s)[b] | Reference[c] |
|---|---|---|---|
| AQP0 (see, e.g., SEQ ID NOs: 34-37) | Low | 13 ± 2 | 38 |
| AQP1 (see, e.g., SEQ ID NOs: 38 and 39) | High | 190 ± 20 | 38 |
| AQP2 (see, e.g., SEQ ID NO: 40) | High | 100 ± 10 | 38 |
| AQP3 | High | 80 ± 20 | 38 |
| AQP4 (see, e.g., SEQ ID NO: 41) | High | 290 ± 10 | 38 |
| AQP5 (see, e.g., SEQ ID NO: 42) | High | 100 ± 10 | 38 |
| AQP6 (see, e.g., SEQ ID NO: 43) | Low | 7.4 ± 0.7 | 39 |
| AQP7 | High | 150 | 40 |
| AQP8 (see, e.g., SEQ ID NO: 44) | High | 205 ± 12 | 41 |
| AQP9 | High | 289 ± 66 | 42 |
| AQP10 | High | 87 | 43 |
| AQP11 (see, e.g., SEQ ID NO: 46) | Low | 15 ± 6 | 44 |
| AQP12 (see, e.g., SEQ ID NO: 47) | NK[c] | NK | |
| SoPIP2;1 (SEQ ID NO: 33) | High | 110 | 2 |

[a]Water permeabilites were categorized as either high or low based on $P_f$ values, using a cut off value of 50 $\mu$m/s.
[b]Osmotic water permeability ($P_f$-values, average ± SD) were determined by heterologous overexpression in *Xenopus laevis* oocytes. 5 to 50 ng of cRNA encoding an aquaporin were injected. After a preincubation to allow protein expression, oocytes were transferred to hypotonic media and the swelling rates were recorded and used to calculate the $P_f$-values.
[c]NK, not known The invention also relates to a method of how to produce said aquaporin. The method comprises the steps of providing said aquaporin, adding a ligand to said aquaporin, producing crystals and obtaining an aquaporin having a ligand bound to the cytoplasmic side of said aquaporin, wherein said ligand close the conformation of said aquaporin and inhibit and/or reduce water transport through said aquaporin. The method being described in the examples.

Methods of Using the Isolated Aquaporin

The invented isolated aquaporin having a closed conformation, wherein said closed conformation is obtained by binding a ligand to said aquaporin as defined above, said crystal as well as said atomic structure may be used in several applications such as to screen for binding agents (ligand) that stabilise and/or destabilise the closed conformation of said aquaporin or to create homology models of closed aquaporins based on the closed structure as defined by the coordinates deposited at PDB ID:1Z98 and as set forth in Appendix 1, to create molecular dynamics simulations of such homology models of eukaryotic or prokaryotic aquaporins, to identify binding agents or identification of at least one genetic modification capable of affecting the gating mechanism of said aquaporin, such as by an in silico technique or to develop genetically modified plants, such as agricultural plants.

According to another aspect, the invention relates to a method of obtaining a binding agent (ligand) comprising: attaching a number of aquaporins or parts thereof being defined above to a solid support and obtaining an array; adding a number of agents to said array; allowing said agents to bind to said aquaporins or parts thereof; removing said agents which have not bound to said aquaporin or parts thereof and identifying and obtaining said agents which have bound to said aquaporins or parts thereof. In certain aspects one or more steps may be used such as attaching a number of aquaporins having a open conformation and then performing the same steps as with the aquaporins with a closed conformation. By adding such steps it is possible to discriminate between agents, which binds to the aquaporins having a closed conformation from those binding to the aquaporins having an open conformation. The most commonly used assay being a High Throughput Assays. The power of high throughput screening is utilized to test new compounds, which are identified or designed for their ability to interact with an aquaporin of the invention. (For general information on high-throughput screening see, for example, Devlin, 1998, High Throughput Screening, Marcel Dekker; U.S. Pat. No. 5,763,263). High throughput assays commonly use one or more different assay techniques including, but not limited to, those described below. Said solid support may be any solid support such as a column, an array, a membrane, a sandwich assay, competitive or competition assay, latex agglutination assay, homogeneous assay, micro-titre plate format and the micro-particle based assay.

The aquaporin may be bound to the support by for instance covalent attachment, hydrophobic interactions and/or ionic interactions. The number of agents may be a mixture of different agents, natural, synthetic, semisynthetic or a mixture thereof and organic compounds. After the agents have had the opportunity to bind to the aquaporin, the unbound agents are removed by for example washing by the use of a water solution of buffers such as TRIS, PBS or MOPS. After removal of the unbound agents, the bound agents are to be identified which may be performed by for example NMR, MS and antibodies, such as monoclonal antibodies. The antibodies can be labelled in various ways, including: enzyme-linked immunosorbent assay (ELISA); radioimmuno assay (RIA); fluorescent immunoassay (FIA); chemiluminescent immunoassay (CLIA); and labeling the antibody with colloidal gold particles (immunogold).

According to a further aspect, the invention relates to a method of obtaining an aquaporin binding agent comprising: using the atomic coordinates as defined above and at least one molecular structural technique to determine which agents interacts with an aquaporin and identifying and obtaining said aquaporin binding agent. Such a method may also contain one or more additional steps, such as those mentioned above in which open aquaporins are used in the same way as the aquaporins having a closed conformation to discriminate between agents which binds one or both of the different types of aquaporins. For basic information on molecular modelling, see, for example, M. Schlecht, Molecular Modelling on the PC, 1998, John Wiley & Sons; Gans et al., Fundamental Principals of Molecular Modelling, 1996, Plenum Pub. Corp.; N. C. Cohen (editor), Guidebook on Molecular Modelling in Drug Design, 1996, Academic Press; and W. B.

Smith, Introduction to Theoretical Organic Chemistry and Molecular Modelling, 1996. The molecular structural technique may be one of MOSFLM, SCALA, MOLREP, REFMAC5, NCSREF and CNS.

According to a further aspect, the invention relates to a method of obtaining a modified agent comprising: using the atomic coordinates as defined above and at least one molecular modelling technique to determine how to modify the interaction of an agent with an aquaporin; modifying said agent based on the determination obtained in step (a) and producing and obtaining a modified agent. The modifications of the agent may be addition, elimination, modification or substitution of functional groups. There are several softwares that may be used and they include as follows; GRID (Goodford, P. J., "A Computational Procedure for Determining Energetically Favourable Binding Sites on Biologically Important Macromolecules" J. Med. Chem., 28, pp. 849-857 (1985)).

The use of software such as GRID, a program that determines probable interaction sites between probes with various functional group characteristics and the macromolecular surface, is used to analyze the surface sites to determine structures of similar inhibiting proteins or compounds. The GRID calculations, with suitable inhibiting groups on molecules (e.g., protonated primary amines) as the probe, are used to identify potential hotspots around accessible positions at suitable energy contour levels. GRID is available from Oxford University, Oxford, UK.

MCSS (Miranker, A. and M. Karplus, "Functionality Maps of Binding Sites: A Multiple Copy Simultaneous Search Method." Proteins: Structure, Function and Genetics, 11, pp. 29-34 (1991)). MCSS is available from Molecular Simulations, Burlington, Mass.

AUTODOCK (Goodsell, D. S. and A. J. Olsen, "Automated Docking of Substrates to Proteins by Simulated Annealing" Proteins: Structure. Function, and Genetics, 8, pp. 195-202 (1990)). AUTODOCK is available from Scripps Research Institute, La Jolla, Calif.

DOCK (Kuntz, I. D. et al., "A Geometric Approach to Macromolecule-Ligand Interactions" J. Mol. Biol., 161, pp. 269-288 (1982)).

The program DOCK may be used to analyze an active site or ligand binding site and suggest ligands with complementary steric properties. DOCK is available from University of California, San Francisco, Calif.

Once suitable chemical entities, compounds, or agents have been selected, they can be assembled into a single ligand or compound or inhibitor or activator. Assembly may proceed by visual inspection of the relationship of the fragments to each other on the three-dimensional image displayed on a computer screen in relation to the atomic coordinates of the aquaporin and/or its complexes with analogues. This would be followed by manual model building using software such as Quanta or Sybyl.

Useful programs to aid one of skill in the art in connecting the individual chemical entities, compounds, or agents include but are not limited to:

CAVEAT (Bartlett, P. A. et al, "CAVEAT: A Program to Facilitate the Structure-Derived Design of Biologically Active Molecules". In molecular Recognition in Chemical and Biological Problems", Special Pub., Royal Chem. Soc., 78, pp. 82-196 (1989)).

Several methodologies for searching three-dimensional databases to test pharmacophore hypotheses and select compounds for screening are available. These include the program CAVEAT (Bacon et al. J. Mol. Biol., 225: 849-858 (1992)) which uses databases of cyclic compounds which can act as "spacers" to connect any number of chemical fragments already positioned in the active site. This allows one skilled in the art to quickly generate hundreds of possible ways to connect the fragments already known or suspected to be necessary for tight binding. CAVEAT is available from the University of California, Berkeley, Calif.

3D Database systems such as MACCS-3D (MDL Information Systems, San Leandro, Calif.). This area is reviewed in Martin, Y. C., "3D Database Searching in Drug Design", J. Med. Chem., 35, pp. 2145-2154 (1992).

HOOK (available from Molecular Simulations, Burlington, Mass.).

The invented crystal of the aquaporin may be used for several purposes including the methods mentioned above to gain information, which can be used to identify compound as well as modify aquaporins. By obtaining the structure of a closed aquaporin it will be possible to use the knowledge of that particular structure to modify the gating. This can in plants be done by direct genetic engineering of aquaporins in order to improve stress tolerance, e.g. against drought stress. In mammalian species pharmaceutical compounds that stabilize the closed or the open conformation of aquaporins can be designed based on the closed conformation of SoPIP2;1 (SEQ ID NO: 33). Such inhibitors and activators are candidate pharmaceutical and cosmeceutical compounds, e.g. antiperspirants.

In a final aspect, the invention relates to the use of a ligand to close the conformation of an aquaporin. The ligand to be used being defined and mentioned above.

Following examples are intended to illustrate, but not to limit, the invention in any manner, shape, or form, either explicitly or implicitly.

EXAMPLES

Example 1

Expression in *Pichia pastoris*

As Described in Ref 28

The SoPIP2;1 cDNA (GeneBank accession number L77969) was originally amplified using the forward primer EcoRI-YPM28A (5'-CGGAATTCAAAATGTCTAAG-GAAGTAAGT-3', SEQ ID NO:1) and the reverse primer PM28A-REV (5'-GAAGATCTTTAATTGGTAGGGT-TGCT-3', SEQ ID NO:2). The forward primer has a EcoRI restriction site (underlined) and yeast start codon. The reverse primer has the original stop codon after PM28A and a BglII restriction site (underlined). The PCR product was cloned into pPICZB (Invitrogen) and the resulting plasmid pPM28A-PICZ was sequenced.

PM28A constructs were transformed into the wild-type *P. pastoris* strain X-33 (Invitrogen) and transformants with the highest expression according to immunostaining (TetraHis antibodies, Qiagen) were selected and grown on a large scale.

Example 2

Purification of SoPIP2;1

As Described in Ref 28 and 36

The strain was grown in a 3 L fermentor typically resulting in 230 g wet cells/L culture after 24 h of methanol induction. Before breaking, the cells were resuspended in Breaking Buffer (50 mM potassium phosphate, pH 7.5, 5% glycerol), frozen in liquid nitrogen and broken using an X-press. Unbroken cells were collected at 10 000 g, 30 min at 4° C. The 10 000 g supernatant was further centrifuged at 100 000 g, 1.5 h at 4° C. to collect the membrane fraction. Peripheral membrane proteins and proteins adhering to the membranes were removed by urea (4 M urea, 5 mM Tris-HCl, pH 9.5, 2 mM EDTA, 2 mM EGTA)/alkali (20 mM NaOH) treatment. The membrane was washed in each buffer and collected by centrifugation after each wash as described above. SoPIP2;1 (SEQ ID NO: 33) was solubilised in 5% OG (Anatrace) in Buffer A (20 mM HEPES-NaOH, pH 7.0, 50 mM NaCl, 10% glycerol, 2 mM beta-mercapto ethanol) at room temperature for 30 min. Solubilised material was collected at 160 000 g, 30 min at 4° C. Solubilised material was loaded on a Resource S column (20 mM HEPES-NaOH, pH 7.0, 1% OG) followed by a Superdex 200 column (20 mM Tris-HCl, pH 7.5, 100 mM NaCl, 1% OG).

Example 3

Crystallisation

The purified sample was concentrated using a VivaSpin 20 concentrator (cutoff MW 10 kDa, VivaScience) to a final concentration of 15 mg/ml.

Crystals were obtained by the hanging drop vapour diffusion technique. 1 μl of sample was mixed 1:1 with the reservoir solution containing 0.1 M Tris-HCl pH 8.0, 30% PEG 400 and 0.1 M NaCl. 0.1 M $CdCl_2$ was added to the drop in a 1:10 ratio.

The crystallisation setups were left to equilibrate at 4° C. Crystals appeared within a few days and reached the maximum dimension of 0.1 μm within 1 week. Crystals were directly frozen in liquid nitrogen without the need for further cryo-protecting.

X-ray diffraction data collection: A complete data set to 2.1 Å resolution was collected from a frozen crystal at −80° C. at the Swiss Light Source (SLS) beamline X06SA, Switzerland. Image data were processed using MOSFLM and scaled using SCALA of the CCP4 suite (29). Crystals belong to the space group 14 with 2 molecules in the asymmetric unit. The cell dimensions are a=b=90.0 Å, c=188.9 Å.

The atomic structure characterised by the coordinates are deposited at the Protein Data Bank ID:1Z98 and as set forth in Appendix 1.

TABLE 1

Data collection and refinement statistics

| Data Collection | |
| --- | --- |
| Space group | I4 |
| Cell dimensions | |
| a, b, c (Å) | 90.0, 90.0, 188.9 |
| α, β, γ (°) | 90.0, 90.0, 90.0 |
| *Resolution (Å) | 40.0-2.1 (2.27-2.1) |
| *†$R_{sym}$ | 0.098 (0.431) |
| *I/σI | 5.0 (1.8) |
| *Completeness (%) | 99.8 (99.8) |
| *Redundancy | 3.9 (3.2) |
| Refinement | |
| *Resolution (Å) | 40.0-2.1 (2.27-2.1) |
| No. reflections | 41486 |
| ‡$R_{work}$/§$R_{free}$ | 0.181/0.208 |
| No. atoms | |
| Protein | 3756 |
| Ligand/ion | 2 |
| Water | 200 |

TABLE 1-continued

Data collection and refinement statistics

| B-factors | |
| --- | --- |
| Protein | 29.7 |
| Ligand/ion | 30.6 |
| Water | 39.6 |
| R.m.s deviations | |
| Bond lengths (Å) | 0.02 |
| Bond angles (°) | 1.540 |

*Values in parentheses indicate statistics for the highest resolution shell.
†$R_{sym}$ = Ó | $I_o$ − <I> |/Ó $I_o$ × 100%, where $I_o$ is the observed intensity of a reflection and <I> is the average intensity obtained from multiple observations of symmetry related reflections.
‡$R_{work}$ = Ó |$F_{obs}$| − k|$F_{calc}$||/Ó |$F_{obs}$| × 100%.
§$R_{free}$ is calculated from 5% of the data which was excluded from refinement.

Example 4

Molecular Replacement & Structural Refinement

Molecular replacement was carried out using the program MOLREP from the CCCP4i-program suite with the coordinates of bovine AQP1 (PDB entry 1J4N) (SEQ ID NO: 38) as the model. Using two copies of the model in the molecular replacement search, a clear solution with a correlation coefficient and R-factor of 34.3% and 53.1% respectively was found. The crystal packing was checked using the program O (30) and there were no overlaps between molecules. Automated model building was carried out using ARP/WARP (31) and the resulting model was docked to the correct sequence using GUISIDE2. The calculated electron density map at this stage was already of very good quality. Water molecules were picked using ARP/WARP. The model was subjected to multiple rounds of refinement in REFMAC5 (29), NCSREF (29) and CNS (32) with manual rebuilding in O between each round. During refinement, NCS restraints between the two molecules in the asymmetric unit (molecule A and B) were used. The current model contains 251 residues (24-274) and one $Cd^{2+}$ each for molecule A and B and 200 water molecules. The R-factor and Rfree are 18.1% and 20.8% respectively. The quality of the structure was checked in PROCHECK (33).

Assignment of $Cd^{2+}$: A single metal binding site was unambiguously observed as a dominant peak (still visible at 10.0σ) in the anomalous difference density map (FIG. 6) and was identified as a divalent cation due its coordination properties. Since the addition of 0.1 M $CdCl_2$ to crystals improved diffraction from 3.7 Å to 2.1 Å resolution, we further assigned this cation as $Cd^{2+}$. This assignment was justified by recovering a B-factor of 29.8 $A^2$ for the $Cd^{2+}$ after refinement, similar to that of the side chains of its two protein ligands (average B-factor of 27 $A^2$). A search for similar binding sites using SPASM (34) yielded 13 hits (PDB entries 1BQQ; 1CGE; 1CGL; 1HY7; 1JK3; 1M31; 1MMQ; 1MNC; 1Q3A; 1RM8; 1RMZ; 1ROS; 830C) containing $Ca^{2+}$ binding sites, and no other metals were found. We therefore make the identification that the $Cd^{2+}$ binding site is likely to be $Ca^{2+}$ in vivo.

Example 5

Characterising the Channel

Figure 4:
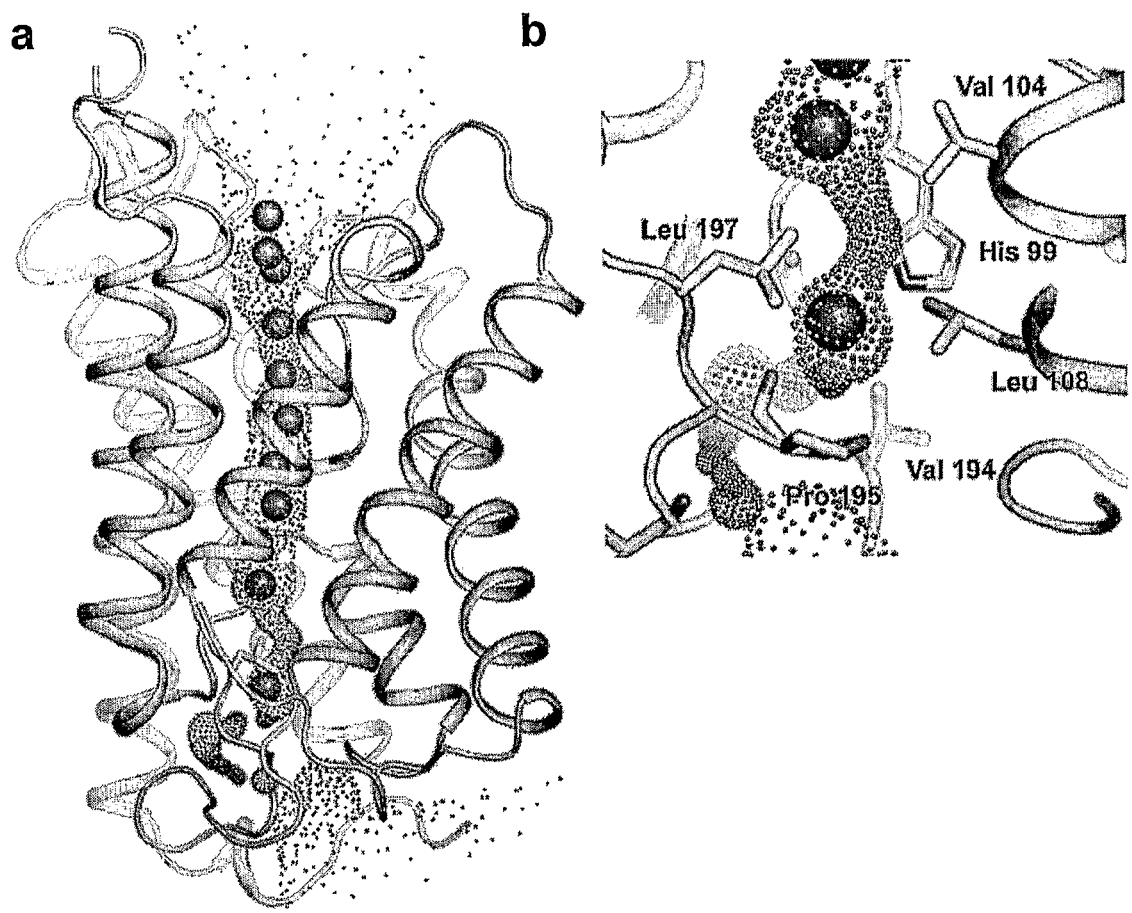
FIG. 4 shows representation of the closed conformation of SoPIP2;1. Representation of the closed conformation of SoPIP2;1. a, The pore diameter of the closed conformation of SoPIP2;1 calculated using HOLE represented as a funnel with dots illustrating the pore boundaries. b, A close up view of the pore near the gating region of loop D characterized by Leu197, Pro195 and Val194 (SEQ ID NO: 33).

The package HOLE (23) was used to calculate the pore diameter for SoPIP2;1 (SEQ ID NO: 33), (FIG. 4). With this package a pore diameter of 2.1 Å was recovered at the constriction region, apparently smaller than the effective diameter of water. This paradox is resolved by appreciating that HOLE returns an average diameter assuming a spherical pore, which is an approximation.

REFERENCES

1. Preston, G. M., Carroll, T. P., Guggino, W. B. & Agre, P. Appearance of water channels in *Xenopus* oocytes expressing red cell CHIP28 protein. Science 256, 385-387 (1992).
2. Johansson I., Karlsson M., Shukla V. K., Chrispeels M. J., Larsson C. & Kjellbom P. Water transport activity of the plasma membrane aquaporin PM28A is regulated by phosphorylation. Plant Cell 10, 451-459 (1998).
3. Johansson, I., Larsson, C., Ek, B. & Kjellbom, P. The major integral proteins of spinach leaf plasma membranes are putative aquaporins and are phosphorylated in response to $Ca^{2+}$ and apoplastic water potential. Plant Cell 8, 1181-1191 (1996).
4. Tournaire-Roux, C., Sutka M., Javot H., Gout E., Gerbeau P., Luu D. T., Bligny R. & Maurel C. Cytosolic pH regulates root water transport during anoxic stress through gating of aquaporins. Nature 425, 393-397 (2003).
5. King, L. S., Kozono, D. & Agre, P. From structure to disease: the evolving tale of aquaporin biology. Nat Rev Mol Cell Biol 5, 687-698 (2004).
6. Agre, P. & Kozono, D. Aquaporin water channels: molecular mechanisms for human diseases. FEBS Lett 555, 72-78 (2003).
7. Johansson, I., Karlsson, M., Johanson, U., Larsson, C. & Kjellbom, P. The role of aquaporins in cellular and whole plant water balance. Biochim Biophys Acta 1465, 324-342 (2000).
8. Tamas, M. J., Karlgren S., Bill R. M., Hedfalk K., Allegri L., Ferreira M., Thevelein J. M., Rydstrom J., Mullins J. G. & Hohmann S. A short regulatory domain restricts glycerol transport through yeast Fps 1p. J Biol Chem 278, 6337-6345 (2003).
9. Johanson, U., Karlsson M., Johansson I., Gustaysson S., Sjovall S., Fraysse L., Weig A. R. & Kjellbom P. The complete set of genes encoding major intrinsic proteins in *Arabidopsis* provides a framework for a new nomenclature for major intrinsic proteins in plants. Plant Physiol 126, 1358-1369 (2001).
10. Morishita, Y., Sakube, Y., Sasaki, S. & Ishibashi, K. Molecular mechanisms and drug development in aquaporin water channel diseases: aquaporin superfamily (superaquaporins): expansion of aquaporins restricted to multicellular organisms. J Pharmacol Sci 96, 276-279 (2004).
11. Borstlap, A. C. Early diversification of plant aquaporins. Trends Plant Sci 7, 529-530 (2002).
12. Murata, K., Mitsuoka K., Hirai T., Walz T., Agre P., Heymann J. B., Engel A. & Fujiyoshi Y. Structural determinants of water permeation through aquaporin-1. Nature 407, 599-605 (2000).
13. Sui, H., Han, B. G., Lee, J. K., Walian, P. & Jap, B. K. Structural basis of water-specific transport through the AQP1 water channel. Nature 414, 872-878 (2001).
14. Savage, D. F., Egea, P. F., Robles-Colmenares, Y., O'Connell, J. D. & Stroud, R. M. Architecture and selectivity in aquaporins: 2.5 a X-ray structure of aquaporin Z. PLoS Biol 1, E72 (2003).
15. Gonen, T., Sliz, P., Kistler, J., Cheng, Y. & Walz, T. Aquaporin-0 membrane junctions reveal the structure of a closed water pore. Nature 429, 193-197 (2004).
16. Harries, W. E., Akhavan, D., Miercke, L. J., Khademi, S. & Stroud, R. M. The channel architecture of aquaporin 0 at a 2.2-A resolution. Proc Natl Acad Sci USA 101, 14045-14050 (2004).
17. Fu, D. et al. Structure of a glycerol-conducting channel and the basis for its selectivity. Science 290, 481-486 (2000).
19. Jung, J. S., Preston, G. M., Smith, B. L., Guggino, W. B. & Agre, P. Molecular structure of the water channel through aquaporin CHIP. The hourglass model. J Biol Chem 269, 14648-14654 (1994).
21. de Groot, B. L. & Grubmuller, H. Water permeation across biological membranes: mechanism and dynamics of aquaporin-1 and G1 pF. Science 294, 2353-2357 (2001).
23. Smart, O, S., Goodfellow, J. M. & Wallace, B. A. The pore dimensions of gramicidin A. Biophys J 65, 2455-2460 (1993).
24. Zelenina, M., Bondar, A. A., Zelenin, S. & Aperia, A. Nickel and extracellular acidification inhibit the water permeability of human aquaporin-3 in lung epithelial cells. J Biol Chem 278, 30037-30043 (2003).
25. Zelenina, M., Tritto, S., Bondar, A. A., Zelenin, S. & Aperia, A. Copper inhibits the water and glycerol permeability of aquaporin-3. J Biol Chem 279, 51939-51943 (2004).
26. Madsen, D. & Kleywegt, G. J. Interactive motif and fold recognition in protein structures. J Appl Crystallogr 35, 137-139 (2001).
27. Saadoun, S., Papadopoulos, M. C., Hara-Chikuma, M. & Verkman, A. S. Impairment of angiogenesis and cell migration by targeted aquaporin-1 gene disruption. Nature 434, 786-792 (2005).
28. Karlsson, M., Fotiadis D., Sjovall S., Johansson I., Hedfalk K., Engel A. & Kjellbom P. Reconstitution of water channel function of an aquaporin overexpressed and purified from *Pichia pastoris*. FEBS Lett 537, 68-72 (2003).
29. Bailey, S. The CCP4 Suite: Programs for Protein Crystallography. Acta Crystallogr D 50, 760-763 (1994).
30. Jones, T. A., Zou, J.-Y., Cowan, S. W. & Kjeldgaard, M. Improved methods for building protein models in electron density maps and the location of errors in these models. Acta Cryst A 47, 110-119 (1991).
31. Morris, R. J., Perrakis, A. & Lamzin, V. S. ARP/wARP and automatic interpretation of protein electron density maps. Methods Enzymol 374, 229-244 (2003).
32. Brunger, A. T., Adams P. D., Clore G. M., DeLano W. L., Gros P., Grosse-Kunstleve R. W., Jiang J. S., Kuszewski J., Nilges M., Pannu N. S., Read R. J., Rice L. M., Simonson T. & Warren G. L. Crystallography & NMR system: A new software suite for macromolecular structure determination. Acta Crystallogr D 54, 905-921 (1998).
33. Laskowski, R. A., Rullmannn, J. A., MacArthur, M. W., Kaptein, R. & Thornton, J. M. AQUA and PROCHECK-NMR: programs for checking the quality of protein structures solved by NMR. J Biomol NMR 8, 477-486 (1996).
34. Madsen, D. & Kleywegt, G. J. Interactive motif and fold recognition in protein structures. J Appl Crystallogr 35, 137-139 (2001).
35. Han B. G., Guliaev A. B., Walian P. J. & Jap B. K. Water transport in AQP0 aquaporin: molecular dynamics studies. J Mol Biol 360, 285-296 (2006).
36. Törnroth-Horsefield S., Wang Y., Hedfalk K., Johanson U., Karlsson M., Tajkhorshid E., Neutze R. & Kjellbom P. Structural mechanism of plant aquaporin gating. Nature 439, 688-694 (2006)
37. Kukulski W., Schenk A. D., Johanson U., Braun T., de Groot B. L., Fotiadis D., Kjellbom P. & Engel A. The 5 Å structure of heterologously expressed plant aquaporin SoPIP2;1. J Mol Biol 350, 611-616 (2005).
38. Yang B. & Verkman A. S. Water and glycerol permeability of aquaporins 1-5 and MIP determined quantitatively by expression of epitope-tagged constructs in *Xenopus* oocytes. J Biol Chem 272, 16140-16146 (1997).
39. Ma T., Yang B., Kuo W. L. & Verkman A S. cDNA cloning and gene structure of a novel water channel expressed exclusively in human kidney: evidence for a gene cluster of aquaporins at chromosome locus 12q13. Genomics 35, 543-550 (1996).
40. Kondo H., Shimomura I., Kishida K., Kuriyama H., Makino Y., Nishizawa H., Matsuda M., Maeda N., Nagaretani H., Kihara S., Kurachi Y., Nakamura T., Funahashi T. & Matsuzawa Y. Human aquaporin adipose (AQPap) gene. Genomic structure, promoter analysis and functional mutation. Eur J Biochem 269, 1814-1826 (2002).
41. Ishibashi K., Kuwahara M., Kageyama Y., Tohsaka A., Marumo F. & Sasaki S. Cloning and functional expression of a second new aquaporin abundantly expressed in testis. Biochem Biophys Res Commun. 237, 714-718 (1997).
42. Kuriyama H., Kawamoto S., Ishida N., Ohno I., Mita S., Matsuzawa Y., Matsubara K. & Okubo K. Molecular cloning and expression of a novel human aquaporin from adipose tissue with glycerol permeability. Biochem Biophys Res Commun 241, 53-58 (1997).
43. Ishibashi K., Morinaga T., Kuwahara M., Sasaki S. & Imai M. Cloning and identification of a new member of water channel (AQP10) as an aquaglyceroporin. Biochim Biophys Acta 1576, 335-340 (2002).
44. Gorelick D. A., Praetorius J., Tsunenari T., Nielsen S. & Agre P. Aquaporin-11: a channel protein lacking apparent transport function expressed in brain. BMC Biochem 7, 14 (2006).

The invention claimed is:

1. A crystalline closed aquaporin of SEQ ID NO:33, wherein said aquaporin is a spinach aquaporin denoted SoPIP2;1 and comprises a bound cadmium ion; the crystal being in space I4 and having unit cell dimensions a, b, c (Å) 90.0, 90.0, 188.9 and α, β, γ (°) 90.0, 90.0, 90.0.

2. The aquaporin according to claim 1, wherein said aquaporin is a crystal of an aquaporin having a high resolution structure characterized by the atomic coordinates set forth in Appendix 1.

3. A method of producing a crystalline aquaporin according to claim 1 by the hanging drop vapor diffusion technique comprising:
   providing an aqueous solution of an aquaporin consisting of the amino acid sequence according to SEQ ID NO: 33;
   adding an aqueous solution containing Tris-HCl pH 8.0, PEG 400 and NaCl to said aqueous solution of the aquaporin;
   provide a hanging drop of the aqueous solution comprising said aquaporin, Tris-HCl pH 8.0, PEG 400 and NaCl, over a reservoir solution containing Tris-HCl pH 8.0, PEG 400 and NaCl at the same concentrations as the aqueous solution added to the aqueous solution of said aquaporin;
   adding $CdCl_2$ to said drop; and
   leave the crystallization setup to equilibrate to produce crystals comprising the aquaporin.

* * * * *

SEQUENCE LISTING

```
<160> NUMBER OF SEQ ID NOS: 91

<210> SEQ ID NO 1
<211> LENGTH: 29
<212> TYPE: DNA
<213> ORGANISM: Artificial Sequence
<220> FEATURE:
<223> OTHER INFORMATION: Forward PCR Primer EcoRI-YPM28A

<400> SEQUENCE: 1
cggaattcaa aatgtctaag gaagtaagt                                      29

<210> SEQ ID NO 2
<211> LENGTH: 26
<212> TYPE: DNA
<213> ORGANISM: Artificial Sequence
<220> FEATURE:
<223> OTHER INFORMATION: Reverse PCR Primer PM28A-REV

<400> SEQUENCE: 2
gaagatcttt aattggtagg gttgct                                         26

<210> SEQ ID NO 3
<211> LENGTH: 287
<212> TYPE: PRT
<213> ORGANISM: Zea mays

<400> SEQUENCE: 3

Met Glu Gly Lys Glu Glu Asp Val Arg Leu Gly Ala Asn Lys Phe Ser
1               5                   10                  15

Glu Arg His Ala Ile Gly Thr Ala Ala Gln Gly Thr Asp Asp Lys Asp
            20                  25                  30

Tyr Lys Glu Pro Pro Ala Pro Leu Phe Glu Pro Gly Glu Leu Lys
        35                  40                  45

Ser Trp Ser Phe Tyr Arg Pro Gly Ile Ala Glu Phe Val Ala Thr Phe
    50                  55                  60

Leu Phe Leu Tyr Ile Ser Ile Leu Thr Val Met Gly Val Ser Lys Ser
65                  70                  75                  80

Thr Ser Lys Cys Ala Thr Val Gly Ile Gln Gly Ile Ala Trp Ser Phe
                85                  90                  95

Gly Gly Met Ile Leu Ala Leu Val Tyr Cys Thr Ala Gly Ile Ser Gly
            100                 105                 110

His Ile Asn Pro Ala Val Thr Phe Gly Leu Phe Leu Ala Arg Lys Leu
```

```
                    115                 120                 125
Ser Leu Thr Arg Ala Val Phe Tyr Ile Ile Met Gln Cys Leu Gly Ala
130                 135                 140

Ile Cys Gly Arg Gly Val Val Lys Gly Phe Gln Gln Gly Leu Tyr Met
145                 150                 155                 160

Gly Asn Gly Gly Arg Arg Asn Val Val Ala Pro Gly Tyr Thr Lys Gly
                165                 170                 175

Asp Gly Leu Gly Ala Glu Ile Val Gly Thr Phe Ile Leu Val Tyr Thr
            180                 185                 190

Val Phe Ser Ala Thr Asp Ala Lys Arg Arg Ala Arg Asp Ser His Val
        195                 200                 205

Pro Ile Leu Ala Pro Leu Pro Ile Gly Phe Ala Val Phe Leu Val His
    210                 215                 220

Leu Ala Thr Met Gly Ile Thr Gly Thr Gly Ile Asn Pro Ala Arg Ser
225                 230                 235                 240

Leu Gly Ala Ala Val Ile Tyr Asn Gln His His Ala Trp Ala Asp His
                245                 250                 255

Trp Ile Phe Trp Val Gly Pro Phe Ile Gly Ala Ala Leu Ala Ala Ile
            260                 265                 270

Tyr His Gln Val Ile Ile Arg Ala Ile Pro Phe Lys Ser Arg Ser
        275                 280                 285

<210> SEQ ID NO 4
<211> LENGTH: 289
<212> TYPE: PRT
<213> ORGANISM: Zea mays

<400> SEQUENCE: 4

Met Glu Gly Lys Glu Asp Val Arg Leu Gly Ala Asn Lys Phe Ser
1               5                   10                  15

Glu Arg Gln Pro Ile Gly Thr Ala Ala Gln Gly Ala Ala Asp Asp Lys
                20                  25                  30

Asp Tyr Lys Glu Pro Pro Ala Pro Leu Phe Glu Pro Gly Glu Leu
            35                  40                  45

Lys Ser Trp Ser Phe Tyr Arg Ala Gly Ile Ala Glu Phe Val Ala Thr
50                  55                  60

Phe Leu Phe Leu Tyr Ile Thr Ile Leu Thr Val Met Gly Val Ser Lys
65                  70                  75                  80

Ser Thr Ser Lys Cys Ala Thr Val Gly Ile Gln Gly Ile Ala Trp Ser
                85                  90                  95

Phe Gly Gly Met Ile Phe Ala Leu Val Tyr Cys Thr Ala Gly Ile Ser
            100                 105                 110

Gly Gly His Ile Asn Pro Ala Val Thr Phe Gly Leu Phe Leu Ala Arg
        115                 120                 125

Lys Leu Ser Leu Thr Arg Ala Leu Phe Tyr Ile Ile Met Gln Cys Leu
    130                 135                 140

Gly Ala Val Cys Gly Ala Gly Val Val Lys Gly Phe Gln Gln Gly Leu
145                 150                 155                 160

Tyr Met Gly Asn Gly Gly Ala Asn Val Val Ala Pro Gly Tyr Thr
                165                 170                 175

Lys Gly Asp Gly Leu Gly Ala Glu Ile Val Gly Thr Phe Ile Leu Val
            180                 185                 190

Tyr Thr Val Phe Ser Ala Thr Asp Ala Lys Arg Asn Ala Arg Asp Ser
        195                 200                 205

His Val Pro Ile Leu Ala Pro Leu Pro Ile Gly Phe Ala Val Phe Leu
```

```
                 210                 215                 220
Val His Leu Ala Thr Ile Pro Ile Thr Gly Thr Gly Ile Asn Pro Ala
225                 230                 235                 240

Arg Ser Leu Gly Ala Ala Ile Ile Tyr Asn Arg Asp His Ala Trp Asn
                245                 250                 255

Asp His Trp Ile Phe Trp Val Gly Pro Phe Ile Gly Ala Ala Leu Ala
260                 265                 270

Ala Ile Tyr His Gln Val Ile Ile Arg Ala Ile Pro Phe Lys Ser Arg
                275                 280                 285

Ser

<210> SEQ ID NO 5
<211> LENGTH: 292
<212> TYPE: PRT
<213> ORGANISM: Zea mays

<400> SEQUENCE: 5

Met Glu Gly Lys Glu Asp Val Arg Leu Gly Ala Asn Lys Phe Ser
1               5                   10                  15

Glu Arg Gln Pro Ile Gly Thr Ala Ala Gln Gly Ala Gly Ala Gly Asp
                20                  25                  30

Asp Asp Lys Asp Tyr Lys Glu Pro Pro Ala Pro Leu Phe Glu Pro
            35                  40                  45

Gly Glu Leu Lys Ser Trp Ser Phe Tyr Arg Ala Gly Ile Ala Glu Phe
50                  55                  60

Val Ala Thr Phe Leu Phe Leu Tyr Ile Thr Val Leu Thr Val Met Gly
65                  70                  75                  80

Val Ser Lys Ser Thr Ser Lys Cys Ala Thr Val Gly Ile Gln Gly Ile
                85                  90                  95

Ala Trp Ser Phe Gly Gly Met Ile Phe Ala Leu Val Tyr Cys Thr Ala
                100                 105                 110

Gly Ile Ser Gly Gly His Ile Asn Pro Ala Val Thr Phe Gly Leu Phe
                115                 120                 125

Leu Ala Arg Lys Leu Ser Leu Thr Arg Ala Ile Phe Tyr Ile Ile Met
130                 135                 140

Gln Cys Leu Gly Ala Ile Cys Gly Ala Gly Val Val Lys Gly Phe Gln
145                 150                 155                 160

Gln Gly Leu Tyr Met Gly Asn Gly Gly Gly Ala Asn Val Val Ala Pro
                165                 170                 175

Gly Tyr Thr Lys Gly Asp Gly Leu Gly Ala Glu Ile Val Gly Thr Phe
                180                 185                 190

Ile Leu Val Tyr Thr Val Phe Ser Ala Thr Asp Ala Lys Arg Asn Ala
                195                 200                 205

Arg Asp Ser His Val Pro Ile Leu Ala Pro Leu Pro Ile Gly Phe Ala
210                 215                 220

Val Phe Leu Val His Leu Ala Thr Ile Pro Ile Thr Gly Thr Gly Ile
225                 230                 235                 240

Asn Pro Ala Arg Ser Leu Gly Ala Ala Ile Ile Tyr Asn Arg Asp His
                245                 250                 255

Ala Trp Ser Asp His Trp Ile Phe Trp Val Gly Pro Phe Ile Gly Ala
                260                 265                 270

Ala Leu Ala Ala Ile Tyr His Gln Val Ile Ile Arg Ala Ile Pro Phe
                275                 280                 285

Lys Ser Arg Ser
            290
```

<210> SEQ ID NO 6
<211> LENGTH: 292
<212> TYPE: PRT
<213> ORGANISM: Zea mays

<400> SEQUENCE: 6

Met Glu Gly Lys Glu Glu Asp Val Arg Leu Gly Ala Asn Lys Phe Ser
1               5                   10                  15

Glu Arg Gln Pro Ile Gly Thr Ala Ala Gln Gly Ala Gly Ala Gly Asp
            20                  25                  30

Asp Asp Lys Asp Tyr Lys Glu Pro Pro Ala Pro Leu Phe Glu Pro
        35                  40                  45

Gly Glu Leu Lys Ser Trp Ser Phe Tyr Arg Ala Gly Ile Ala Glu Phe
    50                  55                  60

Val Ala Thr Phe Leu Phe Leu Tyr Ile Thr Val Leu Thr Val Met Gly
65                  70                  75                  80

Val Ser Lys Ser Thr Ser Lys Cys Ala Thr Val Gly Ile Gln Gly Ile
                85                  90                  95

Ala Trp Ser Phe Gly Gly Met Ile Phe Ala Leu Val Tyr Cys Thr Ala
            100                 105                 110

Gly Ile Ser Gly Gly His Ile Asn Pro Ala Val Thr Phe Gly Leu Phe
        115                 120                 125

Leu Ala Arg Lys Leu Ser Leu Thr Arg Ala Ile Phe Tyr Ile Ile Met
    130                 135                 140

Gln Cys Leu Gly Ala Ile Cys Gly Ala Gly Val Val Lys Gly Phe Gln
145                 150                 155                 160

Gln Gly Leu Tyr Met Gly Asn Gly Gly Gly Ala Asn Val Val Ala Pro
                165                 170                 175

Gly Tyr Thr Lys Gly Asp Gly Leu Gly Ala Glu Ile Val Gly Thr Phe
            180                 185                 190

Ile Leu Val Tyr Thr Val Phe Ser Ala Thr Asp Ala Lys Arg Asn Ala
        195                 200                 205

Arg Asp Ser His Val Pro Ile Leu Ala Pro Leu Pro Ile Gly Phe Ala
    210                 215                 220

Val Phe Leu Val His Leu Ala Thr Ile Pro Ile Thr Gly Thr Gly Ile
225                 230                 235                 240

Asn Pro Ala Arg Ser Leu Gly Ala Ala Ile Ile Tyr Asn Arg Asp His
                245                 250                 255

Ala Trp Ser Asp His Trp Ile Phe Trp Val Gly Pro Phe Ile Gly Ala
            260                 265                 270

Ala Leu Ala Ala Ile Tyr His Gln Val Ile Ile Arg Ala Ile Pro Phe
        275                 280                 285

Lys Ser Arg Ser
    290

<210> SEQ ID NO 7
<211> LENGTH: 288
<212> TYPE: PRT
<213> ORGANISM: Zea mays

<400> SEQUENCE: 7

Met Glu Gly Lys Glu Glu Asp Val Arg Leu Gly Ala Asn Arg Tyr Ser
1               5                   10                  15

Glu Arg Gln Pro Ile Gly Thr Ala Ala Gln Gly Thr Glu Glu Lys Asp
            20                  25                  30

Tyr Lys Glu Pro Pro Ala Pro Leu Phe Glu Ala Glu Leu Thr
        35              40                  45

Ser Trp Ser Phe Tyr Arg Ala Gly Ile Ala Glu Phe Val Ala Thr Phe
50                      55                  60

Leu Phe Leu Tyr Ile Ser Ile Leu Thr Val Met Gly Val Ser Lys Ser
65                  70                  75                  80

Ser Ser Lys Cys Ala Thr Val Gly Ile Gln Gly Ile Ala Trp Ser Phe
                85                  90                  95

Gly Gly Met Ile Phe Ala Leu Val Tyr Cys Thr Ala Gly Ile Ser Gly
            100                 105                 110

Gly His Ile Asn Pro Ala Val Thr Phe Gly Leu Phe Leu Ala Arg Lys
            115                 120                 125

Leu Ser Leu Thr Arg Ala Leu Phe Tyr Met Val Met Gln Cys Leu Gly
130                 135                 140

Ala Ile Cys Gly Ala Gly Val Val Lys Gly Phe Gln Glu Gly Leu Tyr
145                 150                 155                 160

Met Gly Ala Gly Gly Ala Asn Ala Val Asn Pro Gly Tyr Thr Lys
            165                 170                 175

Gly Asp Gly Leu Gly Ala Glu Ile Val Gly Thr Phe Val Leu Val Tyr
            180                 185                 190

Thr Val Phe Ser Ala Thr Asp Ala Lys Arg Ser Ala Arg Asp Ser His
            195                 200                 205

Val Pro Ile Leu Ala Pro Leu Pro Ile Gly Phe Ala Val Phe Leu Val
210                 215                 220

His Leu Ala Thr Ile Pro Ile Thr Gly Thr Gly Ile Asn Pro Ala Arg
225                 230                 235                 240

Ser Leu Gly Ala Ala Ile Val Tyr Asn Arg Ser His Ala Trp Asn Asp
                245                 250                 255

His Trp Ile Phe Trp Val Gly Pro Phe Ile Gly Ala Ala Leu Ala Ala
            260                 265                 270

Ile Tyr His Val Val Ile Ile Arg Ala Leu Pro Phe Lys Ser Arg Asp
            275                 280                 285

<210> SEQ ID NO 8
<211> LENGTH: 296
<212> TYPE: PRT
<213> ORGANISM: Zea mays

<400> SEQUENCE: 8

Met Ala Gly Gly Thr Leu Gln Asp Arg Ser Glu Glu Glu Asp Val Arg
1               5                   10                  15

Val Gly Val Asp Arg Phe Pro Glu Arg Gln Pro Ile Gly Thr Ala Ala
            20                  25                  30

Asp Asp Leu Gly Arg Asp Tyr Ser Glu Pro Pro Ala Ala Pro Leu Phe
            35                  40                  45

Glu Ala Ser Glu Leu Ser Ser Trp Ser Phe Tyr Arg Ala Gly Ile Ala
        50                  55                  60

Glu Phe Val Ala Thr Phe Leu Phe Leu Tyr Val Thr Val Leu Thr Val
65                  70                  75                  80

Met Gly Val Ser Lys Ser Pro Ser Lys Cys Gly Thr Val Gly Ile Gln
                85                  90                  95

Gly Ile Ala Trp Ala Phe Gly Gly Met Ile Phe Ala Leu Val Tyr Cys
            100                 105                 110

Thr Ala Gly Val Ser Gly Gly His Ile Asn Pro Ala Val Thr Phe Gly
            115                 120                 125

```
Leu Leu Leu Ala Arg Lys Leu Ser Leu Thr Arg Ala Val Tyr Tyr Val
            130                 135                 140

Val Met Gln Cys Leu Gly Ala Val Cys Gly Ala Gly Val Val Lys Ala
145                 150                 155                 160

Phe Gly Ser Ala Leu Tyr Glu Ser Ala Gly Gly Ala Asn Ala Val
                    165                 170                 175

Ser Pro Gly Tyr Thr Lys Gly Asp Gly Leu Gly Ala Glu Val Val Gly
                180                 185                 190

Thr Phe Val Leu Val Tyr Thr Val Phe Ser Ala Thr Asp Ala Lys Arg
            195                 200                 205

Thr Ala Arg Asp Ser His Val Pro Ala Leu Ala Pro Leu Pro Ile Gly
            210                 215                 220

Phe Ala Val Phe Leu Val His Leu Ala Thr Ile Pro Ile Thr Gly Thr
225                 230                 235                 240

Gly Ile Asn Pro Ala Arg Ser Leu Gly Ala Ala Ile Ile Tyr Asp Asn
                    245                 250                 255

Pro His Gly Trp His Gly His Trp Ile Phe Trp Val Gly Pro Phe Ala
                260                 265                 270

Gly Ala Ala Leu Ala Ala Val Tyr His Gln Val Val Leu Arg Ala Ile
                275                 280                 285

Pro Phe Lys Ser Ser Ala His Tyr
                290                 295

<210> SEQ ID NO 9
<211> LENGTH: 286
<212> TYPE: PRT
<213> ORGANISM: Arabidopsis thaliana

<400> SEQUENCE: 9

Met Glu Gly Lys Glu Asp Val Arg Val Gly Ala Asn Lys Phe Pro
1               5                   10                  15

Glu Arg Gln Pro Ile Gly Thr Ser Ala Gln Ser Asp Lys Asp Tyr Lys
            20                  25                  30

Glu Pro Pro Pro Ala Pro Phe Phe Glu Pro Gly Glu Leu Ser Ser Trp
        35                  40                  45

Ser Phe Trp Arg Ala Gly Ile Ala Glu Phe Ile Ala Thr Phe Leu Phe
    50                  55                  60

Leu Tyr Ile Thr Val Leu Thr Val Met Gly Val Lys Arg Ser Pro Asn
65                  70                  75                  80

Met Cys Ala Ser Val Gly Ile Gln Gly Ile Ala Trp Ala Phe Gly Gly
                85                  90                  95

Met Ile Phe Ala Leu Val Tyr Cys Thr Ala Gly Ile Ser Gly Gly His
                100                 105                 110

Ile Asn Pro Ala Val Thr Phe Gly Leu Phe Leu Ala Arg Lys Leu Ser
            115                 120                 125

Leu Thr Arg Ala Leu Tyr Tyr Ile Val Met Gln Cys Leu Gly Ala Ile
            130                 135                 140

Cys Gly Ala Gly Val Val Lys Gly Phe Gln Pro Lys Gln Tyr Gln Ala
145                 150                 155                 160

Leu Gly Gly Gly Ala Asn Thr Val Ala His Gly Tyr Thr Lys Gly Ser
                    165                 170                 175

Gly Leu Gly Ala Glu Ile Ile Gly Thr Phe Val Leu Val Tyr Thr Val
                180                 185                 190

Phe Ser Ala Thr Asp Ala Lys Arg Asn Ala Arg Asp Ser His Val Pro
            195                 200                 205
```

```
Ile Leu Ala Pro Leu Pro Ile Gly Phe Ala Val Phe Leu Val His Leu
    210                 215                 220

Ala Thr Ile Pro Ile Thr Gly Thr Gly Ile Asn Pro Ala Arg Ser Leu
225                 230                 235                 240

Gly Ala Ala Ile Ile Tyr Asn Lys Asp His Ser Trp Asp Asp His Trp
                245                 250                 255

Val Phe Trp Val Gly Pro Phe Ile Gly Ala Ala Leu Ala Ala Leu Tyr
                260                 265                 270

His Val Val Ile Arg Ala Ile Pro Phe Lys Ser Arg Ser
                275                 280                 285
```

<210> SEQ ID NO 10
<211> LENGTH: 286
<212> TYPE: PRT
<213> ORGANISM: Arabidopsis thaliana

<400> SEQUENCE: 10

```
Met Glu Gly Lys Glu Glu Asp Val Arg Val Gly Ala Asn Lys Phe Pro
1               5                   10                  15

Glu Arg Gln Pro Ile Gly Thr Ser Ala Gln Ser Asp Lys Asp Tyr Lys
                20                  25                  30

Glu Pro Pro Pro Ala Pro Leu Phe Glu Pro Gly Glu Leu Ala Ser Trp
            35                  40                  45

Ser Phe Trp Arg Ala Gly Ile Ala Glu Phe Ile Ala Thr Phe Leu Phe
50                  55                  60

Leu Tyr Ile Thr Val Leu Thr Val Met Gly Val Lys Arg Ser Pro Asn
65                  70                  75                  80

Met Cys Ala Ser Val Gly Ile Gln Gly Ile Ala Trp Ala Phe Gly Gly
                85                  90                  95

Met Ile Phe Ala Leu Val Tyr Cys Thr Ala Gly Ile Ser Gly Gly His
                100                 105                 110

Ile Asn Pro Ala Val Thr Phe Gly Leu Phe Leu Ala Arg Lys Leu Ser
                115                 120                 125

Leu Thr Arg Ala Val Tyr Tyr Ile Val Met Gln Cys Leu Gly Ala Ile
130                 135                 140

Cys Gly Ala Gly Val Val Lys Gly Phe Gln Pro Lys Gln Tyr Gln Ala
145                 150                 155                 160

Leu Gly Gly Gly Ala Asn Thr Ile Ala His Gly Tyr Thr Lys Gly Ser
                165                 170                 175

Gly Leu Gly Ala Glu Ile Ile Gly Thr Phe Val Leu Val Tyr Thr Val
                180                 185                 190

Phe Ser Ala Thr Asp Ala Lys Arg Asn Ala Arg Asp Ser His Val Pro
                195                 200                 205

Ile Leu Ala Pro Leu Pro Ile Gly Phe Ala Val Phe Leu Val His Leu
    210                 215                 220

Ala Thr Ile Pro Ile Thr Gly Thr Gly Ile Asn Pro Ala Arg Ser Leu
225                 230                 235                 240

Gly Ala Ala Ile Ile Phe Asn Lys Asp Asn Ala Trp Asp Asp His Trp
                245                 250                 255

Val Phe Trp Val Gly Pro Phe Ile Gly Ala Ala Leu Ala Ala Leu Tyr
                260                 265                 270

His Val Ile Val Ile Arg Ala Ile Pro Phe Lys Ser Arg Ser
                275                 280                 285
```

<210> SEQ ID NO 11
<211> LENGTH: 286

```
<212> TYPE: PRT
<213> ORGANISM: Arabidopsis thaliana

<400> SEQUENCE: 11

Met Glu Gly Lys Glu Glu Asp Val Arg Val Gly Ala Asn Lys Phe Pro
1               5                   10                  15

Glu Arg Gln Pro Ile Gly Thr Ser Ala Gln Thr Asp Lys Asp Tyr Lys
            20                  25                  30

Glu Pro Pro Ala Pro Phe Phe Glu Pro Gly Glu Leu Ser Ser Trp
        35                  40                  45

Ser Phe Tyr Arg Ala Gly Ile Ala Glu Phe Ile Ala Thr Phe Leu Phe
    50                  55                  60

Leu Tyr Ile Thr Val Leu Thr Val Met Gly Val Lys Arg Ala Pro Asn
65                  70                  75                  80

Met Cys Ala Ser Val Gly Ile Gln Gly Ile Ala Trp Ala Phe Gly Gly
                85                  90                  95

Met Ile Phe Ala Leu Val Tyr Cys Thr Ala Gly Ile Ser Gly Gly His
            100                 105                 110

Ile Asn Pro Ala Val Thr Phe Gly Leu Phe Leu Ala Arg Lys Leu Ser
        115                 120                 125

Leu Thr Arg Ala Val Phe Tyr Ile Val Met Gln Cys Leu Gly Ala Ile
    130                 135                 140

Cys Gly Ala Gly Val Val Lys Gly Phe Gln Pro Asn Pro Tyr Gln Thr
145                 150                 155                 160

Leu Gly Gly Gly Ala Asn Thr Val Ala His Gly Tyr Thr Lys Gly Ser
                165                 170                 175

Gly Leu Gly Ala Glu Ile Ile Gly Thr Phe Val Leu Val Tyr Thr Val
            180                 185                 190

Phe Ser Ala Thr Asp Ala Lys Arg Ser Ala Arg Asp Ser His Val Pro
        195                 200                 205

Ile Leu Ala Pro Leu Pro Ile Gly Phe Ala Val Phe Leu Val His Leu
    210                 215                 220

Ala Thr Ile Pro Ile Thr Gly Thr Gly Ile Asn Pro Ala Arg Ser Leu
225                 230                 235                 240

Gly Ala Ala Ile Ile Tyr Asn Lys Asp His Ala Trp Asp Asp His Trp
                245                 250                 255

Ile Phe Trp Val Gly Pro Phe Ile Gly Ala Ala Leu Ala Ala Leu Tyr
            260                 265                 270

His Gln Leu Val Ile Arg Ala Ile Pro Phe Lys Ser Arg Ser
        275                 280                 285

<210> SEQ ID NO 12
<211> LENGTH: 287
<212> TYPE: PRT
<213> ORGANISM: Arabidopsis thaliana

<400> SEQUENCE: 12

Met Glu Gly Lys Glu Glu Asp Val Arg Val Gly Ala Asn Lys Phe Pro
1               5                   10                  15

Glu Arg Gln Pro Ile Gly Thr Ser Ala Gln Ser Thr Asp Lys Asp Tyr
            20                  25                  30

Lys Glu Pro Pro Ala Pro Leu Phe Glu Pro Gly Glu Leu Ser Ser
        35                  40                  45

Trp Ser Phe Tyr Arg Ala Gly Ile Ala Glu Phe Ile Ala Thr Phe Leu
    50                  55                  60

Phe Leu Tyr Ile Thr Val Leu Thr Val Met Gly Val Lys Arg Ala Pro
```

```
                65                  70                  75                  80
Asn Met Cys Ala Ser Val Gly Ile Gln Gly Ile Ala Trp Ala Phe Gly
                    85                  90                  95

Gly Met Ile Phe Ala Leu Val Tyr Cys Thr Ala Gly Ile Ser Gly Gly
                100                 105                 110

His Ile Asn Pro Ala Val Thr Phe Gly Leu Phe Leu Ala Arg Lys Leu
                115                 120                 125

Ser Leu Thr Arg Ala Val Phe Tyr Met Ile Met Gln Cys Leu Gly Ala
                130                 135                 140

Ile Cys Gly Ala Gly Val Val Lys Gly Phe Gln Pro Thr Pro Tyr Gln
145                 150                 155                 160

Thr Leu Gly Gly Gly Ala Asn Thr Val Ala His Gly Tyr Thr Lys Gly
                165                 170                 175

Ser Gly Leu Gly Ala Glu Ile Ile Gly Thr Phe Val Leu Val Tyr Thr
                180                 185                 190

Val Phe Ser Ala Thr Asp Ala Lys Arg Ser Ala Arg Asp Ser His Val
                195                 200                 205

Pro Ile Leu Ala Pro Leu Pro Ile Gly Phe Ala Val Phe Leu Val His
                210                 215                 220

Leu Ala Thr Ile Pro Ile Thr Gly Thr Gly Ile Asn Pro Ala Arg Ser
225                 230                 235                 240

Leu Gly Ala Ala Ile Ile Tyr Asn Lys Asp His Ser Trp Asp Asp His
                245                 250                 255

Trp Ile Phe Trp Val Gly Pro Phe Ile Gly Ala Ala Leu Ala Ala Leu
                260                 265                 270

Tyr His Gln Ile Val Ile Arg Ala Ile Pro Phe Lys Ser Lys Ser
                275                 280                 285

<210> SEQ ID NO 13
<211> LENGTH: 287
<212> TYPE: PRT
<213> ORGANISM: Arabidopsis thaliana

<400> SEQUENCE: 13

Met Glu Gly Lys Glu Asp Val Asn Val Gly Ala Asn Lys Phe Pro
1               5                   10                  15

Glu Arg Gln Pro Ile Gly Thr Ala Ala Gln Thr Glu Ser Lys Asp Tyr
                20                  25                  30

Lys Glu Pro Pro Ala Pro Phe Phe Glu Pro Gly Glu Leu Lys Ser
                35                  40                  45

Trp Ser Phe Tyr Arg Ala Gly Ile Ala Glu Phe Ile Ala Thr Phe Leu
50                  55                  60

Phe Leu Tyr Val Thr Val Leu Thr Val Met Gly Val Lys Arg Ala Pro
65                  70                  75                  80

Asn Met Cys Ala Ser Val Gly Ile Gln Gly Ile Ala Trp Ala Phe Gly
                85                  90                  95

Gly Met Ile Phe Ala Leu Val Tyr Cys Thr Ala Gly Ile Ser Gly Gly
                100                 105                 110

His Ile Asn Pro Ala Val Thr Phe Gly Leu Phe Leu Ala Arg Lys Leu
                115                 120                 125

Ser Leu Thr Arg Ala Leu Phe Tyr Ile Val Met Gln Cys Leu Gly Ala
                130                 135                 140

Ile Cys Gly Ala Gly Val Val Lys Gly Phe Gln Pro Gly Leu Tyr Gln
145                 150                 155                 160

Thr Asn Gly Gly Gly Ala Asn Val Val Ala His Gly Tyr Thr Lys Gly
```

```
              165                 170                 175
Ser Gly Leu Gly Ala Glu Ile Val Gly Thr Phe Val Leu Val Tyr Thr
            180                 185                 190

Val Phe Ser Ala Thr Asp Ala Lys Arg Ser Ala Arg Asp Ser His Val
            195                 200                 205

Pro Ile Leu Ala Pro Leu Pro Ile Gly Phe Ala Val Phe Leu Val His
            210                 215                 220

Leu Ala Thr Ile Pro Ile Thr Gly Thr Gly Ile Asn Pro Ala Arg Ser
225                 230                 235                 240

Leu Gly Ala Ala Ile Ile Tyr Asn Lys Asp His Ala Trp Asp Asp His
                245                 250                 255

Trp Ile Phe Trp Val Gly Pro Phe Ile Gly Ala Ala Leu Ala Ala Leu
            260                 265                 270

Tyr His Gln Ile Val Ile Arg Ala Ile Pro Phe Lys Ser Lys Thr
            275                 280                 285

<210> SEQ ID NO 14
<211> LENGTH: 288
<212> TYPE: PRT
<213> ORGANISM: Picea abies

<400> SEQUENCE: 14

Met Glu Gly Lys Glu Glu Asp Val Arg Leu Gly Ala Asn Lys Tyr Ser
1               5                   10                  15

Glu Arg Gln Pro Leu Gly Thr Ala Ala Gln Thr Arg Glu Lys Asp Tyr
            20                  25                  30

Lys Asp Ser Gly Pro Ala Pro Leu Phe Glu Pro Gly Glu Leu Ala Ser
            35                  40                  45

Trp Ser Phe Trp Arg Ala Gly Ile Ala Glu Phe Met Ala Thr Phe Leu
        50                  55                  60

Phe Leu Tyr Ile Thr Ile Leu Thr Val Met Gly Val Lys Arg Ser Asp
65                  70                  75                  80

Asp Val Cys Thr Gly Ser Val Gly Ile Gln Gly Ile Ala Trp Ala Phe
                85                  90                  95

Gly Gly Met Ile Phe Cys Leu Val Tyr Cys Thr Ala Gly Ile Ser Gly
            100                 105                 110

Gly His Ile Asn Pro Ala Val Thr Phe Gly Leu Phe Leu Ala Arg Lys
            115                 120                 125

Leu Ser Leu Pro Arg Ala Val Phe Tyr Met Ile Cys Gln Cys Leu Gly
130                 135                 140

Ala Ile Cys Gly Ala Gly Val Val Lys Gly Phe Met Glu Ser Glu Tyr
145                 150                 155                 160

Glu Met Asp Gly Gly Ala Asn Ser Val Ala His Gly Tyr Thr Lys
                165                 170                 175

Gly Asp Gly Leu Gly Ala Glu Ile Val Gly Thr Phe Val Leu Val Tyr
            180                 185                 190

Thr Val Phe Ser Ala Thr Asp Ala Lys Arg Ser Ala Arg Asp Ser His
            195                 200                 205

Val Pro Met Leu Ala Pro Leu Pro Ile Gly Phe Ala Val Phe Leu Val
            210                 215                 220

His Leu Ala Thr Ile Pro Ile Thr Gly Thr Gly Ile Asn Pro Ala Arg
225                 230                 235                 240

Ser Leu Gly Ala Ala Ile Ile Tyr Asn Lys Ser His Ala Trp Asp Asp
                245                 250                 255

His Trp Ile Phe Trp Val Gly Pro Phe Leu Gly Ala Gly Leu Ala Ala
```

```
                         260                 265                 270
        Phe Tyr His Gln Met Ile Ile Arg Ala Ile Pro Phe Lys Thr Arg Ser
                         275                 280                 285

<210> SEQ ID NO 15
<211> LENGTH: 286
<212> TYPE: PRT
<213> ORGANISM: Physcomitrella patens

<400> SEQUENCE: 15

Met Ala Asp Arg Gly Asp Val Ala Val Gly Ala Ser Arg His Glu
1               5                   10                  15

Arg Asn Pro Leu Gly Thr Ser Ala Gln Thr Arg Glu Lys Asp Tyr Ile
                20                  25                  30

Glu Pro Ala Ser Ser Pro Phe Ile Asp Pro Val Glu Leu Gly Arg Trp
            35                  40                  45

Ser Phe Trp Arg Ala Gly Ile Ala Glu Phe Phe Ala Ser Phe Leu Phe
        50                  55                  60

Leu Tyr Ile Thr Val Gln Thr Val Met Gly His Asn Arg Gly Asp Ala
65                  70                  75                  80

Cys Ala Gly Val Gly Ile Gln Gly Ile Ala Trp Ala Phe Gly Gly Met
                85                  90                  95

Ile Phe Thr Leu Val Tyr Cys Thr Ala Gly Ile Ser Gly Gly His Ile
                100                 105                 110

Asn Pro Ala Val Thr Phe Gly Leu Phe Leu Ala Arg Lys Val Thr Phe
            115                 120                 125

Pro Arg Thr Val Leu Tyr Ile Val Cys Gln Cys Leu Gly Ala Ile Cys
130                 135                 140

Gly Ala Gly Ala Val Lys Gly Phe Gln Pro Asp Phe Tyr Gln Ser Val
145                 150                 155                 160

Gly Gly Gly Ala Asn Thr Val Ala His Gly Tyr Thr Lys Gly Asp Gly
                165                 170                 175

Leu Gly Ala Glu Ile Val Gly Thr Phe Val Leu Val Tyr Thr Val Phe
            180                 185                 190

Ser Ala Thr Asp Ala Lys Arg Asn Ala Arg Asp Ser His Val Pro Leu
        195                 200                 205

Leu Ala Pro Leu Pro Ile Gly Phe Ala Val Phe Leu Val His Leu Ala
    210                 215                 220

Thr Ile Pro Ile Thr Gly Thr Ser Ile Asn Pro Ala Arg Ser Leu Gly
225                 230                 235                 240

Ala Ala Val Ile Trp Asn Arg Asp Gln Ala Trp Asn Asp His Trp Ile
                245                 250                 255

Phe Trp Val Gly Pro Ile Leu Gly Ala Thr Leu Ala Ala Met Tyr His
                260                 265                 270

Thr Leu Val Ile Arg Ala Ile Pro Phe Ser Ala Asn Arg Ala
            275                 280                 285

<210> SEQ ID NO 16
<211> LENGTH: 290
<212> TYPE: PRT
<213> ORGANISM: Zea mays

<400> SEQUENCE: 16

Met Gly Lys Asp Asp Val Ile Glu Ser Gly Ala Gly Gly Gly Glu Phe
1               5                   10                  15

Ala Ala Lys Asp Tyr Thr Asp Pro Pro Pro Ala Pro Leu Ile Asp Ala
                20                  25                  30
```

Ala Glu Leu Gly Ser Trp Ser Leu Tyr Arg Ala Val Ile Ala Glu Phe
         35                  40                  45

Ile Ala Thr Leu Leu Phe Leu Tyr Ile Thr Val Ala Thr Val Ile Gly
     50                  55                  60

Tyr Lys His Gln Thr Asp Ala Ser Ala Ser Gly Ala Asp Ala Ala Cys
65                  70                  75                  80

Gly Gly Val Gly Val Leu Gly Ile Ala Trp Ala Phe Gly Gly Met Ile
                 85                  90                  95

Phe Val Leu Val Tyr Cys Thr Ala Gly Ile Ser Gly Gly His Ile Asn
             100                 105                 110

Pro Ala Val Thr Phe Gly Leu Phe Leu Ala Arg Lys Val Ser Leu Val
             115                 120                 125

Arg Ala Leu Leu Tyr Ile Val Ala Gln Cys Leu Gly Ala Ile Cys Gly
    130                 135                 140

Val Gly Leu Val Lys Ala Phe Gln Ser Ala Tyr Phe Asp Arg Tyr Gly
145                 150                 155                 160

Gly Gly Ala Asn Ser Leu Ala Ser Gly Tyr Ser Arg Gly Thr Gly Leu
                165                 170                 175

Gly Ala Glu Ile Ile Gly Thr Phe Val Leu Val Tyr Thr Val Phe Ser
            180                 185                 190

Ala Thr Asp Pro Lys Arg Asn Ala Arg Asp Ser His Val Pro Val Leu
        195                 200                 205

Ala Pro Leu Pro Ile Gly Phe Ala Val Phe Met Val His Leu Ala Thr
    210                 215                 220

Ile Pro Val Thr Gly Thr Gly Ile Asn Pro Ala Arg Ser Leu Gly Ala
225                 230                 235                 240

Ala Val Ile Tyr Asn Lys Asp Lys Pro Trp Asp His Trp Ile Phe
                245                 250                 255

Trp Val Gly Pro Leu Val Gly Ala Ala Ile Ala Ala Phe Tyr His Gln
                260                 265                 270

Tyr Ile Leu Arg Ala Gly Ala Ile Lys Ala Leu Gly Ser Phe Arg Ser
        275                 280                 285

Asn Ala
    290

<210> SEQ ID NO 17
<211> LENGTH: 292
<212> TYPE: PRT
<213> ORGANISM: Zea mays

<400> SEQUENCE: 17

Met Gly Lys Asp Asp Val Val Gln Ser Gly Ala Gly Gly Gly Glu Phe
1               5                   10                  15

Ala Ala Lys Asp Tyr Thr Asp Pro Pro Ala Pro Leu Val Asp Ala
            20                  25                  30

Ala Glu Leu Gly Ser Trp Ser Leu Tyr Arg Ala Val Ile Ala Glu Phe
         35                  40                  45

Ile Ala Thr Leu Leu Phe Leu Tyr Val Thr Val Ala Thr Val Ile Gly
     50                  55                  60

Tyr Lys His Gln Thr Asp Ala Ser Ala Ser Gly Ala Gly Ala Asp Ala
65                  70                  75                  80

Ala Cys Gly Gly Val Gly Val Leu Gly Ile Ala Trp Ala Phe Gly Gly
                 85                  90                  95

Met Ile Phe Val Leu Val Tyr Cys Thr Ala Gly Ile Ser Gly Gly His
             100                 105                 110

```
Ile Asn Pro Ala Val Thr Phe Gly Leu Phe Leu Ala Arg Lys Val Ser
            115                 120                 125

Leu Val Arg Ala Leu Leu Tyr Met Val Ala Gln Cys Leu Gly Ala Val
        130                 135                 140

Cys Gly Val Gly Leu Val Lys Ala Phe Gln Ser Ala Tyr Phe Asp Arg
145                 150                 155                 160

Tyr Gly Gly Gly Ala Asn Ser Leu Ala Ser Gly Tyr Ser Arg Gly Ala
                165                 170                 175

Gly Leu Gly Ala Glu Ile Val Gly Thr Phe Val Leu Val Tyr Thr Val
            180                 185                 190

Phe Ser Ala Thr Asp Pro Lys Arg Asn Ala Arg Asp Ser His Val Pro
        195                 200                 205

Val Leu Ala Pro Leu Pro Ile Gly Phe Ala Val Phe Met Val His Leu
    210                 215                 220

Ala Thr Ile Pro Val Thr Gly Thr Gly Ile Asn Pro Ala Arg Ser Leu
225                 230                 235                 240

Gly Ala Ala Val Val Tyr Asn Lys Asp Lys Pro Trp Asp Asp His Trp
                245                 250                 255

Ile Phe Trp Val Gly Pro Leu Leu Gly Ala Ala Ile Ala Ala Phe Tyr
            260                 265                 270

His Gln Tyr Ile Leu Arg Ala Gly Ala Ile Lys Ala Leu Gly Ser Phe
        275                 280                 285

Arg Ser Asn Ala
    290

<210> SEQ ID NO 18
<211> LENGTH: 289
<212> TYPE: PRT
<213> ORGANISM: Zea mays

<400> SEQUENCE: 18

Met Ala Lys Gln Asp Ile Glu Ala Ser Gly Pro Glu Ala Gly Glu Phe
1               5                   10                  15

Ser Ala Lys Asp Tyr Thr Asp Pro Pro Ala Pro Leu Ile Asp Ala
            20                  25                  30

Asp Glu Leu Thr Lys Trp Ser Leu Tyr Arg Ala Val Ile Ala Glu Phe
        35                  40                  45

Ile Ala Thr Leu Leu Phe Leu Tyr Ile Thr Val Ala Thr Val Ile Gly
    50                  55                  60

Tyr Lys His Gln Thr Asp Ala Ala Ala Ser Gly Pro Asp Ala Ala Cys
65                  70                  75                  80

Gly Gly Val Gly Ile Leu Gly Ile Ala Trp Ala Phe Gly Gly Met Ile
                85                  90                  95

Phe Ile Leu Val Tyr Cys Thr Ala Gly Ile Ser Gly Gly His Ile Asn
            100                 105                 110

Pro Ala Val Thr Phe Gly Leu Phe Leu Ala Arg Lys Val Ser Leu Val
        115                 120                 125

Arg Ala Leu Leu Tyr Ile Ala Gln Cys Leu Gly Ala Ile Cys Gly
    130                 135                 140

Val Gly Leu Val Lys Gly Phe Gln Ser Ala Tyr Tyr Val Arg Tyr Gly
145                 150                 155                 160

Gly Gly Ala Asn Glu Leu Ser Asp Gly Tyr Ser Lys Gly Thr Gly Leu
                165                 170                 175

Ala Ala Glu Ile Ile Gly Thr Phe Val Leu Val Tyr Thr Val Phe Ser
            180                 185                 190
```

```
Ala Thr Asp Pro Lys Arg Ser Ala Arg Asp Ser His Val Pro Val Leu
            195                 200                 205

Ala Pro Leu Pro Ile Gly Phe Ala Val Phe Met Val His Leu Ala Thr
    210                 215                 220

Ile Pro Ile Thr Gly Thr Gly Ile Asn Pro Ala Arg Ser Leu Gly Ala
225                 230                 235                 240

Ala Val Ile Tyr Asn Lys Asp Lys Ala Trp Asp Asp Gln Trp Ile Phe
                245                 250                 255

Trp Val Gly Pro Leu Ile Gly Ala Ala Ile Ala Ala Tyr His Gln
                260                 265                 270

Tyr Val Leu Arg Ala Ser Ala Thr Lys Leu Gly Ser Tyr Arg Ser Asn
    275                 280                 285

Ala
```

<210> SEQ ID NO 19
<211> LENGTH: 288
<212> TYPE: PRT
<213> ORGANISM: Zea mays

<400> SEQUENCE: 19

```
Met Ala Lys Asp Ile Glu Ala Ser Gly Pro Glu Ala Gly Glu Phe Ser
1               5                   10                  15

Ala Lys Asp Tyr Thr Asp Pro Pro Ala Pro Leu Ile Asp Ala Glu
            20                  25                  30

Glu Leu Thr Gln Trp Ser Leu Tyr Arg Ala Val Ile Ala Glu Phe Ile
                35                  40                  45

Ala Thr Leu Leu Phe Leu Tyr Ile Thr Val Ala Thr Val Ile Gly Tyr
    50                  55                  60

Lys His Gln Thr Asp Ala Ser Ala Ser Gly Pro Asp Ala Ala Cys Gly
65                  70                  75                  80

Gly Val Gly Ile Leu Gly Ile Ala Trp Ala Phe Gly Gly Met Ile Phe
                85                  90                  95

Ile Leu Val Tyr Cys Thr Ala Gly Ile Ser Gly Gly His Ile Asn Pro
            100                 105                 110

Ala Val Thr Phe Gly Leu Phe Leu Ala Arg Lys Val Ser Leu Val Arg
        115                 120                 125

Ala Leu Leu Tyr Ile Ile Ala Gln Cys Leu Gly Ala Ile Cys Gly Val
    130                 135                 140

Gly Leu Val Lys Gly Phe Gln Ser Ala Tyr Tyr Val Arg Tyr Gly Gly
145                 150                 155                 160

Gly Ala Asn Glu Leu Ser Asp Gly Tyr Ser Lys Gly Thr Gly Leu Ala
                165                 170                 175

Ala Glu Ile Ile Gly Thr Phe Val Leu Val Tyr Thr Val Phe Ser Ala
            180                 185                 190

Thr Asp Pro Lys Arg Ser Ala Arg Asp Ser His Val Pro Val Leu Ala
        195                 200                 205

Pro Leu Pro Ile Gly Phe Ala Val Phe Met Val His Leu Ala Thr Ile
    210                 215                 220

Pro Ile Thr Gly Thr Gly Ile Asn Pro Ala Arg Ser Leu Gly Ala Ala
225                 230                 235                 240

Val Ile Tyr Asn Lys Asp Lys Ala Trp Asp Asp Gln Trp Ile Phe Trp
                245                 250                 255

Val Gly Pro Leu Ile Gly Ala Ala Ile Ala Ala Tyr His Gln Tyr
            260                 265                 270
```

```
Val Leu Arg Ala Ser Ala Thr Lys Leu Gly Ser Tyr Arg Ser Asn Ala
        275                 280                 285

<210> SEQ ID NO 20
<211> LENGTH: 285
<212> TYPE: PRT
<213> ORGANISM: Zea mays

<400> SEQUENCE: 20

Met Ala Lys Asp Ile Glu Ala Ala Ala His Glu Gly Lys Asp Tyr
1               5                   10                  15

Ser Asp Pro Pro Ala Pro Leu Val Asp Ala Glu Glu Leu Thr Lys
            20                  25                  30

Trp Ser Leu Tyr Arg Ala Val Ile Ala Glu Phe Val Ala Thr Leu Leu
        35                  40                  45

Phe Leu Tyr Ile Thr Val Ala Thr Val Ile Gly Tyr Lys His Gln Thr
    50                  55                  60

Asp Ala Ala Ser Gly Pro Asp Ala Ala Cys Gly Gly Val Gly Val
65                  70                  75                  80

Leu Gly Ile Ala Trp Ala Phe Gly Gly Met Ile Phe Ile Leu Val Tyr
                85                  90                  95

Cys Thr Ala Gly Val Ser Gly Gly His Ile Asn Pro Ala Val Thr Phe
                100                 105                 110

Gly Leu Phe Leu Ala Arg Lys Val Ser Leu Val Arg Ala Leu Leu Tyr
            115                 120                 125

Ile Val Ala Gln Cys Leu Gly Ala Ile Cys Gly Val Gly Leu Val Lys
    130                 135                 140

Gly Phe Gln Ser Ala Phe Tyr Val Arg Tyr Gly Gly Gly Ala Asn Glu
145                 150                 155                 160

Leu Ser Ala Gly Tyr Ser Lys Gly Thr Gly Leu Ala Ala Glu Ile Ile
                165                 170                 175

Gly Thr Phe Val Leu Val Tyr Thr Val Phe Ser Ala Thr Asp Pro Lys
            180                 185                 190

Arg Asn Ala Arg Asp Ser His Val Pro Val Leu Ala Pro Leu Pro Ile
    195                 200                 205

Gly Phe Ala Val Phe Met Val His Leu Ala Thr Ile Pro Ile Thr Gly
210                 215                 220

Thr Gly Ile Asn Pro Ala Arg Ser Leu Gly Ala Ala Val Ile Tyr Asn
225                 230                 235                 240

Asn Asp Lys Ala Trp Asp Asp His Trp Ile Phe Trp Val Gly Pro Phe
                245                 250                 255

Ile Gly Ala Ala Ile Ala Ala Tyr His Gln Tyr Val Leu Arg Ala
            260                 265                 270

Ser Ala Ala Lys Leu Gly Ser Ser Ala Ser Phe Ser Arg
    275                 280                 285

<210> SEQ ID NO 21
<211> LENGTH: 288
<212> TYPE: PRT
<213> ORGANISM: Zea mays

<400> SEQUENCE: 21

Met Gly Lys Glu Val Asp Val Ser Thr Leu Gly Ala Gly Gly Val Arg
1               5                   10                  15

Asp Arg Asp Tyr Ala Asp Pro Pro Ala Pro Leu Ile Asp Ile Asp
            20                  25                  30

Glu Leu Gly Lys Trp Ser Leu Tyr Arg Ala Val Ile Ala Glu Phe Val
```

```
                35                  40                  45
Ala Thr Leu Leu Phe Leu Tyr Ile Thr Val Ala Thr Val Ile Gly Tyr
 50                  55                  60
Lys His Gln Thr Asp Ala Ser Ala Ser Gly Pro Asp Ala Ala Cys Ser
65                  70                  75                  80
Gly Val Gly Ile Leu Gly Ile Ala Trp Ala Phe Gly Gly Met Ile Phe
                85                  90                  95
Ile Leu Val Tyr Cys Thr Ala Gly Ile Ser Gly Gly His Ile Asn Pro
            100                 105                 110
Ala Val Thr Phe Gly Leu Phe Leu Ala Arg Lys Val Ser Leu Val Arg
        115                 120                 125
Ala Leu Leu Tyr Met Ala Ala Gln Ser Leu Gly Ala Ile Cys Gly Val
    130                 135                 140
Ala Leu Val Lys Gly Phe Gln Ser Gly Phe Tyr Ala Arg Tyr Gly Gly
145                 150                 155                 160
Gly Ala Asn Glu Val Ser Ala Gly Tyr Ser Thr Gly Thr Gly Leu Ala
                165                 170                 175
Ala Glu Ile Ile Gly Thr Phe Val Leu Val Tyr Thr Val Phe Ser Ala
            180                 185                 190
Thr Asp Pro Lys Arg Asn Ala Arg Asp Ser His Val Pro Val Leu Ala
        195                 200                 205
Pro Leu Pro Ile Gly Phe Ala Val Phe Met Val His Leu Ala Thr Ile
    210                 215                 220
Pro Ile Thr Gly Thr Gly Ile Asn Pro Ala Arg Ser Leu Gly Ala Ala
225                 230                 235                 240
Val Val Tyr Asn Asn Ser Lys Ala Trp Ser Asp Gln Trp Ile Phe Trp
                245                 250                 255
Val Gly Pro Phe Ile Gly Ala Ala Ile Ala Ala Leu Tyr His Gln Ile
            260                 265                 270
Val Leu Arg Ala Ser Ala Arg Gly Tyr Gly Ser Phe Arg Ser Asn Ala
        275                 280                 285

<210> SEQ ID NO 22
<211> LENGTH: 287
<212> TYPE: PRT
<213> ORGANISM: Zea mays

<400> SEQUENCE: 22

Met Ala Lys Asp Val Glu Gln Val Thr Glu Gln Gly Glu Tyr Ser Ala
1               5                  10                  15
Lys Asp Tyr His Asp Pro Pro Ala Pro Leu Ile Asp Pro Asp Glu
            20                  25                  30
Leu Thr Lys Trp Ser Leu Tyr Arg Ala Ala Ile Ala Glu Phe Ile Ala
        35                  40                  45
Thr Leu Leu Phe Leu Tyr Ile Thr Val Leu Thr Ile Ile Gly Tyr Lys
    50                  55                  60
Arg Gln Ser Asp Thr Lys Ile Pro Gly Asn Thr Glu Cys Asp Gly Val
65                  70                  75                  80
Gly Ile Leu Gly Ile Ala Trp Ala Phe Gly Gly Met Ile Phe Ile Leu
                85                  90                  95
Val Tyr Cys Thr Ala Gly Ile Ser Gly Gly His Ile Asn Pro Ala Val
            100                 105                 110
Thr Phe Gly Leu Phe Leu Gly Arg Lys Val Ser Leu Val Arg Ala Leu
        115                 120                 125
Leu Tyr Met Ile Ala Gln Cys Ala Gly Ala Ile Cys Gly Ala Gly Leu
```

```
            130                 135                 140
Ala Lys Gly Phe Gln Lys Ser Phe Tyr Asn Arg Tyr Gly Gly Val
145                 150                 155                 160

Asn Thr Val Ser Asp Gly Tyr Asn Lys Gly Thr Ala Leu Gly Ala Glu
                165                 170                 175

Ile Ile Gly Thr Phe Val Leu Val Tyr Thr Val Phe Ser Ala Thr Asp
                180                 185                 190

Pro Lys Arg Asn Ala Arg Asp Ser His Val Pro Val Leu Ala Pro Leu
                195                 200                 205

Pro Ile Gly Phe Ala Val Phe Met Val His Leu Ala Thr Ile Pro Val
210                 215                 220

Thr Gly Thr Gly Ile Asn Pro Ala Arg Ser Phe Gly Pro Ala Val Ile
225                 230                 235                 240

Phe Asn Asn Asp Lys Ala Trp Asp Asp Gln Trp Ile Tyr Trp Val Gly
                245                 250                 255

Pro Phe Val Gly Ala Ala Val Ala Ala Ile Tyr His Gln Tyr Ile Leu
                260                 265                 270

Arg Gly Ser Ala Ile Lys Ala Leu Gly Ser Phe Arg Ser Asn Ala
                275                 280                 285

<210> SEQ ID NO 23
<211> LENGTH: 287
<212> TYPE: PRT
<213> ORGANISM: Arabidopsis thaliana

<400> SEQUENCE: 23

Met Ala Lys Asp Val Glu Ala Val Pro Gly Glu Gly Phe Gln Thr Arg
1               5                   10                  15

Asp Tyr Gln Asp Pro Pro Ala Pro Phe Ile Asp Gly Ala Glu Leu
                20                  25                  30

Lys Lys Trp Ser Phe Tyr Arg Ala Val Ile Ala Glu Phe Val Ala Thr
                35                  40                  45

Leu Leu Phe Leu Tyr Ile Thr Val Leu Thr Val Ile Gly Tyr Lys Ile
                50                  55                  60

Gln Ser Asp Thr Asp Ala Gly Gly Val Asp Cys Gly Gly Val Gly Ile
65                  70                  75                  80

Leu Gly Ile Ala Trp Ala Phe Gly Gly Met Ile Phe Ile Leu Val Tyr
                85                  90                  95

Cys Thr Ala Gly Ile Ser Gly Gly His Ile Asn Pro Ala Val Thr Phe
                100                 105                 110

Gly Leu Phe Leu Ala Arg Lys Val Ser Leu Pro Arg Ala Leu Leu Tyr
                115                 120                 125

Ile Ile Ala Gln Cys Leu Gly Ala Ile Cys Gly Val Gly Phe Val Lys
                130                 135                 140

Ala Phe Gln Ser Ser Tyr Tyr Thr Arg Tyr Gly Gly Gly Ala Asn Ser
145                 150                 155                 160

Leu Ala Asp Gly Tyr Ser Thr Gly Thr Gly Leu Ala Ala Glu Ile Ile
                165                 170                 175

Gly Thr Phe Val Leu Val Tyr Thr Val Phe Ser Ala Thr Asp Pro Lys
                180                 185                 190

Arg Ser Ala Arg Asp Ser His Val Pro Val Leu Ala Pro Leu Pro Ile
                195                 200                 205

Gly Phe Ala Val Phe Met Val His Leu Ala Thr Ile Pro Ile Thr Gly
210                 215                 220

Thr Gly Ile Asn Pro Ala Arg Ser Phe Gly Ala Ala Val Ile Tyr Asn
```

-continued

```
            225                 230                 235                 240
Lys Ser Lys Pro Trp Asp Asp His Trp Ile Phe Trp Val Gly Pro Phe
                    245                 250                 255

Ile Gly Ala Ala Ile Ala Ala Phe Tyr His Gln Phe Val Leu Arg Ala
            260                 265                 270

Ser Gly Ser Lys Ser Leu Gly Ser Phe Arg Ser Ala Ala Asn Val
        275                 280                 285

<210> SEQ ID NO 24
<211> LENGTH: 285
<212> TYPE: PRT
<213> ORGANISM: Arabidopsis thaliana

<400> SEQUENCE: 24

Met Ala Lys Asp Val Glu Gly Pro Glu Gly Phe Gln Thr Arg Asp Tyr
1               5                   10                  15

Glu Asp Pro Pro Thr Pro Phe Phe Asp Ala Asp Glu Leu Thr Lys
            20                  25                  30

Trp Ser Leu Tyr Arg Ala Val Ile Ala Glu Phe Val Ala Thr Leu Leu
        35                  40                  45

Phe Leu Tyr Ile Thr Val Leu Thr Val Ile Gly Tyr Lys Ile Gln Ser
    50                  55                  60

Asp Thr Lys Ala Gly Gly Val Asp Cys Gly Gly Val Gly Ile Leu Gly
65                  70                  75                  80

Ile Ala Trp Ala Phe Gly Gly Met Ile Phe Ile Leu Val Tyr Cys Thr
                85                  90                  95

Ala Gly Ile Ser Gly Gly His Ile Asn Pro Ala Val Thr Phe Gly Leu
            100                 105                 110

Phe Leu Ala Arg Lys Val Ser Leu Ile Arg Ala Val Leu Tyr Met Val
        115                 120                 125

Ala Gln Cys Leu Gly Ala Ile Cys Gly Val Gly Phe Val Lys Ala Phe
    130                 135                 140

Gln Ser Ser Tyr Tyr Asp Arg Tyr Gly Gly Gly Ala Asn Ser Leu Ala
145                 150                 155                 160

Asp Gly Tyr Asn Thr Gly Thr Gly Leu Ala Ala Glu Ile Ile Gly Thr
                165                 170                 175

Phe Val Leu Val Tyr Thr Val Phe Ser Ala Thr Asp Pro Lys Arg Asn
            180                 185                 190

Ala Arg Asp Ser His Val Pro Val Leu Ala Pro Leu Pro Ile Gly Phe
        195                 200                 205

Ala Val Phe Met Val His Leu Ala Thr Ile Pro Ile Thr Gly Thr Gly
    210                 215                 220

Ile Asn Pro Ala Arg Ser Phe Gly Ala Ala Val Ile Tyr Asn Lys Ser
225                 230                 235                 240

Lys Pro Trp Asp His Trp Ile Phe Trp Val Gly Pro Phe Ile Gly
                245                 250                 255

Ala Ala Ile Ala Ala Phe Tyr His Gln Phe Val Leu Arg Ala Ser Gly
            260                 265                 270

Ser Lys Ser Leu Gly Ser Phe Arg Ser Ala Ala Asn Val
        275                 280                 285

<210> SEQ ID NO 25
<211> LENGTH: 285
<212> TYPE: PRT
<213> ORGANISM: Arabidopsis thaliana

<400> SEQUENCE: 25
```

```
Met Ala Lys Asp Val Glu Gly Pro Asp Gly Phe Gln Thr Arg Asp Tyr
1               5                   10                  15

Glu Asp Pro Pro Thr Pro Phe Phe Asp Ala Glu Glu Leu Thr Lys
            20                  25                  30

Trp Ser Leu Tyr Arg Ala Val Ile Ala Glu Phe Val Ala Thr Leu Leu
            35                  40                  45

Phe Leu Tyr Val Thr Val Leu Thr Val Ile Gly Tyr Lys Ile Gln Ser
        50                  55                  60

Asp Thr Lys Ala Gly Val Asp Cys Gly Val Gly Ile Leu Gly
65                  70                  75                  80

Ile Ala Trp Ala Phe Gly Gly Met Ile Phe Ile Leu Val Tyr Cys Thr
                85                  90                  95

Ala Gly Ile Ser Gly Gly His Ile Asn Pro Ala Val Thr Phe Gly Leu
            100                 105                 110

Phe Leu Ala Arg Lys Val Ser Leu Ile Arg Ala Val Leu Tyr Met Val
            115                 120                 125

Ala Gln Cys Leu Gly Ala Ile Cys Gly Val Gly Phe Val Lys Ala Phe
        130                 135                 140

Gln Ser Ser His Tyr Val Asn Tyr Gly Gly Gly Ala Asn Phe Leu Ala
145                 150                 155                 160

Asp Gly Tyr Asn Thr Gly Thr Gly Leu Ala Ala Glu Ile Ile Gly Thr
                165                 170                 175

Phe Val Leu Val Tyr Thr Val Phe Ser Ala Thr Asp Pro Lys Arg Asn
            180                 185                 190

Ala Arg Asp Ser His Val Pro Val Leu Ala Pro Leu Pro Ile Gly Phe
            195                 200                 205

Ala Val Phe Met Val His Leu Ala Thr Ile Pro Ile Thr Gly Thr Gly
        210                 215                 220

Ile Asn Pro Ala Arg Ser Phe Gly Ala Ala Val Ile Phe Asn Lys Ser
225                 230                 235                 240

Lys Pro Trp Asp Asp His Trp Ile Phe Trp Val Gly Pro Phe Ile Gly
                245                 250                 255

Ala Thr Ile Ala Ala Phe Tyr His Gln Phe Val Leu Arg Ala Ser Gly
            260                 265                 270

Ser Lys Ser Leu Gly Ser Phe Arg Ser Ala Ala Asn Val
        275                 280                 285

<210> SEQ ID NO 26
<211> LENGTH: 291
<212> TYPE: PRT
<213> ORGANISM: Arabidopsis thaliana

<400> SEQUENCE: 26

Met Ala Lys Asp Leu Asp Val Asn Glu Ser Gly Pro Pro Ala Ala Arg
1               5                   10                  15

Asp Tyr Lys Asp Pro Pro Ala Pro Phe Phe Asp Met Glu Glu Leu
            20                  25                  30

Arg Lys Trp Pro Leu Tyr Arg Ala Val Ile Ala Glu Phe Val Ala Thr
            35                  40                  45

Leu Leu Phe Leu Tyr Val Ser Ile Leu Thr Val Ile Gly Tyr Lys Ala
        50                  55                  60

Gln Thr Asp Ala Thr Ala Gly Gly Val Asp Cys Gly Gly Val Gly Ile
65                  70                  75                  80

Leu Gly Ile Ala Trp Ala Phe Gly Gly Met Ile Phe Val Leu Val Tyr
                85                  90                  95
```

```
Cys Thr Ala Gly Ile Ser Gly Gly His Ile Asn Pro Ala Val Thr Val
            100                 105                 110
Gly Leu Phe Leu Ala Arg Lys Val Ser Leu Val Arg Thr Val Leu Tyr
            115                 120                 125
Ile Val Ala Gln Cys Leu Gly Ala Ile Cys Gly Cys Gly Phe Val Lys
        130                 135                 140
Ala Phe Gln Ser Ser Tyr Tyr Thr Arg Tyr Gly Gly Gly Ala Asn Glu
145                 150                 155                 160
Leu Ala Asp Gly Tyr Asn Lys Gly Thr Gly Leu Gly Ala Glu Ile Ile
                165                 170                 175
Gly Thr Phe Val Leu Val Tyr Thr Val Phe Ser Ala Thr Asp Pro Lys
            180                 185                 190
Arg Asn Ala Arg Asp Ser His Val Pro Val Leu Ala Pro Leu Pro Ile
        195                 200                 205
Gly Phe Ala Val Phe Met Val His Leu Ala Thr Ile Pro Ile Thr Gly
    210                 215                 220
Thr Gly Ile Asn Pro Ala Arg Ser Phe Gly Ala Ala Val Ile Tyr Asn
225                 230                 235                 240
Asn Glu Lys Ala Trp Asp Asp Gln Trp Ile Phe Trp Val Gly Pro Met
                245                 250                 255
Ile Gly Ala Ala Ala Ala Phe Tyr His Gln Phe Ile Leu Arg Ala
            260                 265                 270
Ala Ala Ile Lys Ala Leu Gly Ser Phe Gly Ser Phe Ser Phe Arg
        275                 280                 285
Ser Phe Ala
    290

<210> SEQ ID NO 27
<211> LENGTH: 286
<212> TYPE: PRT
<213> ORGANISM: Arabidopsis thaliana

<400> SEQUENCE: 27

Met Thr Lys Glu Val Val Gly Asp Lys Arg Ser Phe Ser Gly Lys Asp
1               5                   10                  15
Tyr Gln Asp Pro Pro Glu Pro Leu Phe Asp Ala Thr Glu Leu Gly
            20                  25                  30
Lys Trp Ser Phe Tyr Arg Ala Leu Ile Ala Glu Phe Ile Ala Thr Leu
        35                  40                  45
Leu Phe Leu Tyr Val Thr Ile Met Thr Val Ile Gly Tyr Lys Ser Gln
    50                  55                  60
Thr Asp Pro Ala Leu Asn Pro Asp Gln Cys Thr Gly Val Gly Val Leu
65                  70                  75                  80
Gly Ile Ala Trp Ala Phe Gly Gly Met Ile Phe Ile Leu Val Tyr Cys
                85                  90                  95
Thr Ala Gly Ile Ser Gly Gly His Ile Asn Pro Ala Val Thr Phe Gly
            100                 105                 110
Leu Leu Leu Ala Arg Lys Val Thr Leu Val Arg Ala Val Met Tyr Met
            115                 120                 125
Val Ala Gln Cys Leu Gly Ala Ile Cys Gly Val Ala Leu Val Lys Ala
        130                 135                 140
Phe Gln Ser Ala Tyr Phe Thr Arg Tyr Gly Gly Gly Ala Asn Gly Leu
145                 150                 155                 160
Ser Asp Gly Tyr Ser Ile Gly Thr Gly Val Ala Ala Glu Ile Ile Gly
                165                 170                 175
```

```
Thr Phe Val Leu Val Tyr Thr Val Phe Ser Ala Thr Asp Pro Lys Arg
            180                 185                 190

Ser Ala Arg Asp Ser His Val Pro Val Leu Ala Pro Leu Pro Ile Gly
        195                 200                 205

Phe Ala Val Phe Ile Val His Leu Ala Thr Ile Pro Ile Thr Gly Thr
210                 215                 220

Gly Ile Asn Pro Ala Arg Ser Leu Gly Ala Ala Ile Ile Tyr Asn Lys
225                 230                 235                 240

Asp Lys Ala Trp Asp His His Trp Ile Phe Trp Val Gly Pro Phe Ala
                245                 250                 255

Gly Ala Ala Ile Ala Ala Phe Tyr His Gln Phe Val Leu Arg Ala Gly
            260                 265                 270

Ala Ile Lys Ala Leu Gly Ser Phe Arg Ser Gln Pro His Val
        275                 280                 285

<210> SEQ ID NO 28
<211> LENGTH: 289
<212> TYPE: PRT
<213> ORGANISM: Arabidopsis thaliana

<400> SEQUENCE: 28

Met Thr Lys Asp Glu Leu Thr Glu Glu Ser Leu Ser Gly Lys Asp
1               5                   10                  15

Tyr Leu Asp Pro Pro Val Lys Thr Phe Glu Val Arg Glu Leu Lys
            20                  25                  30

Lys Trp Ser Phe Tyr Arg Ala Val Ile Ala Glu Phe Ile Ala Thr Leu
        35                  40                  45

Leu Phe Leu Tyr Val Thr Val Leu Thr Val Ile Gly Phe Lys Ser Gln
    50                  55                  60

Thr Asp Ile Asn Ala Gly Gly Gly Ala Cys Ala Ser Val Gly Leu Leu
65                  70                  75                  80

Gly Ile Ser Trp Ala Phe Gly Gly Met Ile Phe Ile Leu Val Tyr Cys
                85                  90                  95

Thr Ala Gly Ile Ser Gly Gly His Ile Asn Pro Ala Val Thr Phe Gly
            100                 105                 110

Leu Phe Leu Ala Ser Lys Val Ser Leu Val Arg Ala Val Ser Tyr Met
        115                 120                 125

Val Ala Gln Cys Leu Gly Ala Thr Cys Gly Val Gly Leu Val Lys Val
    130                 135                 140

Phe Gln Ser Thr Tyr Tyr Asn Arg Tyr Gly Gly Gly Ala Asn Met Leu
145                 150                 155                 160

Ser Asp Gly Tyr Asn Val Gly Val Gly Val Gly Ala Glu Ile Ile Gly
                165                 170                 175

Thr Phe Val Leu Val Tyr Thr Val Phe Ser Ala Thr Asp Pro Lys Arg
            180                 185                 190

Asn Ala Arg Asp Ser His Ile Pro Val Leu Ala Pro Leu Pro Ile Gly
        195                 200                 205

Phe Ser Val Phe Met Val His Leu Ala Thr Ile Pro Ile Thr Gly Thr
210                 215                 220

Gly Ile Asn Pro Ala Arg Ser Phe Gly Ala Ala Val Ile Tyr Asn Asn
225                 230                 235                 240

Gln Lys Ala Trp Asp Asp Gln Trp Ile Phe Trp Val Gly Pro Phe Val
                245                 250                 255

Gly Ala Ala Ile Ala Ala Phe Tyr His Gln Phe Val Leu Arg Ala Gly
            260                 265                 270
```

Ala Met Lys Ala Tyr Gly Ser Val Arg Ser Gln Leu His Glu Leu His
            275                 280                 285
Ala

<210> SEQ ID NO 29
<211> LENGTH: 280
<212> TYPE: PRT
<213> ORGANISM: Arabidopsis thaliana

<400> SEQUENCE: 29

Met Ser Lys Glu Val Ser Glu Glu Gly Lys Thr His His Gly Lys Asp
1               5                   10                  15

Tyr Val Asp Pro Pro Ala Pro Leu Leu Asp Met Gly Glu Leu Lys
            20                  25                  30

Ser Trp Ser Phe Tyr Arg Ala Leu Ile Ala Glu Phe Ile Ala Thr Leu
            35                  40                  45

Leu Phe Leu Tyr Val Thr Val Ala Thr Val Ile Gly Lys Lys Gln
        50                  55                  60

Thr Gly Pro Cys Asp Gly Val Gly Leu Leu Gly Ile Ala Trp Ala Phe
65                  70                  75                  80

Gly Gly Met Ile Phe Val Leu Val Tyr Cys Thr Ala Gly Ile Ser Gly
                85                  90                  95

Gly His Ile Asn Pro Ala Val Thr Phe Gly Leu Phe Leu Ala Arg Lys
            100                 105                 110

Val Ser Leu Val Arg Ala Leu Gly Tyr Met Ile Ala Gln Cys Leu Gly
        115                 120                 125

Ala Ile Cys Gly Val Gly Phe Val Lys Ala Phe Met Lys Thr Pro Tyr
130                 135                 140

Asn Thr Leu Gly Gly Gly Ala Asn Thr Val Ala Asp Gly Tyr Ser Lys
145                 150                 155                 160

Gly Thr Ala Leu Gly Ala Glu Ile Ile Gly Thr Phe Val Leu Val Tyr
                165                 170                 175

Thr Val Phe Ser Ala Thr Asp Pro Lys Arg Ser Ala Arg Asp Ser His
            180                 185                 190

Ile Pro Val Leu Ala Pro Leu Pro Ile Gly Phe Ala Val Phe Met Val
        195                 200                 205

His Leu Ala Thr Ile Pro Ile Thr Gly Thr Gly Ile Asn Pro Ala Arg
210                 215                 220

Ser Phe Gly Ala Ala Val Ile Tyr Asn Asn Glu Lys Ala Trp Asp Asp
225                 230                 235                 240

Gln Trp Ile Phe Trp Val Gly Pro Phe Leu Gly Ala Leu Ala Ala Ala
                245                 250                 255

Ala Tyr His Gln Tyr Ile Leu Arg Ala Ser Ala Ile Lys Ala Leu Gly
            260                 265                 270

Ser Phe Arg Ser Asn Ala Thr Asn
        275                 280

<210> SEQ ID NO 30
<211> LENGTH: 278
<212> TYPE: PRT
<213> ORGANISM: Arabidopsis thaliana

<400> SEQUENCE: 30

Met Ser Lys Glu Val Ser Glu Glu Gly Arg His Gly Lys Asp Tyr Val
1               5                   10                  15

Asp Pro Pro Pro Ala Pro Leu Leu Asp Met Ala Glu Leu Lys Leu Trp

```
              20                  25                  30
Ser Phe Tyr Arg Ala Ile Ile Ala Glu Phe Ile Ala Thr Leu Leu Phe
            35                  40                  45

Leu Tyr Val Thr Val Ala Thr Val Ile Gly His Lys Asn Gln Thr Gly
 50                  55                  60

Pro Cys Gly Gly Val Gly Leu Leu Gly Ile Ala Trp Ala Phe Gly Gly
 65                  70                  75                  80

Met Ile Phe Val Leu Val Tyr Cys Thr Ala Gly Ile Ser Gly Gly His
                 85                  90                  95

Ile Asn Pro Ala Val Thr Phe Gly Leu Phe Leu Ala Arg Lys Val Ser
                100                 105                 110

Leu Pro Arg Ala Val Ala Tyr Met Val Ala Gln Cys Leu Gly Ala Ile
                115                 120                 125

Cys Gly Val Gly Leu Val Lys Ala Phe Met Met Thr Pro Tyr Lys Arg
                130                 135                 140

Leu Gly Gly Gly Ala Asn Thr Val Ala Asp Gly Tyr Ser Thr Gly Thr
145                 150                 155                 160

Ala Leu Gly Ala Glu Ile Ile Gly Thr Phe Val Leu Val Tyr Thr Val
                165                 170                 175

Phe Ser Ala Thr Asp Pro Lys Arg Ser Ala Arg Asp Ser His Val Pro
                180                 185                 190

Val Leu Ala Pro Leu Pro Ile Gly Phe Ala Val Phe Met Val His Leu
                195                 200                 205

Ala Thr Ile Pro Ile Thr Gly Thr Gly Ile Asn Pro Ala Arg Ser Phe
                210                 215                 220

Gly Ala Ala Val Ile Tyr Asn Asn Glu Lys Ala Trp Asp Asp His Trp
225                 230                 235                 240

Ile Phe Trp Val Gly Pro Phe Val Gly Ala Leu Ala Ala Ala Ala Tyr
                245                 250                 255

His Gln Tyr Ile Leu Arg Ala Ala Ala Ile Lys Ala Leu Ala Ser Phe
                260                 265                 270

Arg Ser Asn Pro Thr Asn
            275

<210> SEQ ID NO 31
<211> LENGTH: 309
<212> TYPE: PRT
<213> ORGANISM: Picea abies

<400> SEQUENCE: 31

Met Thr Lys Glu Glu Arg Arg Glu Ser Glu Gln Gln Gly Phe Pro Pro
 1               5                  10                  15

Lys Asp Tyr Thr Asp Pro Pro Ala Ala Leu Ile Glu Thr Ser Glu
                 20                  25                  30

Phe Lys Leu Trp Ser Phe Tyr Arg Ala Leu Ile Ala Glu Phe Val Ala
            35                  40                  45

Thr Leu Leu Phe Leu Tyr Ile Thr Ile Ala Thr Val Ile Gly His Ser
 50                  55                  60

Arg Thr Ser Thr Asn Cys Gly Ser Val Gly Val Leu Gly Ile Ala Trp
 65                  70                  75                  80

Ser Phe Gly Gly Met Ile Phe Val Leu Val Tyr Cys Thr Ala Gly Ile
                 85                  90                  95

Ser Gly Gly His Ile Asn Pro Ala Val Thr Phe Gly Leu Phe Leu Ala
                100                 105                 110

Arg Lys Val Ser Leu Pro Arg Ala Ile Leu Tyr Met Ile Ala Gln Cys
```

```
                    115                 120                 125
Leu Gly Ala Ile Cys Gly Thr Gly Leu Ala Ile Cys Gly Thr Gly Leu
        130                 135                 140
Val Lys Ser Phe Gln Lys Ser Phe Tyr Asp Arg Tyr Gly Gly Gly Ala
145                 150                 155                 160
Asn Tyr Val His His Gly Tyr Thr Lys Gly Val Gly Leu Ala Ala Glu
                165                 170                 175
Ile Ile Gly Thr Phe Val Leu Val Tyr Thr Val Phe Ser Ala Thr Asp
            180                 185                 190
Pro Lys Arg Ser Ala Arg Asp Ser His Val Pro Val Leu Ala Pro Leu
        195                 200                 205
Pro Ile Gly Phe Ala Val Phe Met Val His Leu Ala Thr Ile Pro Ile
    210                 215                 220
Thr Gly Thr Gly Ile Asn Pro Ala Arg Ser Phe Gly Ala Ala Val Ile
225                 230                 235                 240
Tyr Gly His Lys Gln Ser Trp Asp Asp His Trp Ile Phe Trp Val Gly
                245                 250                 255
Pro Phe Ala Gly Ala Ala Leu Ala Ala Ala Tyr His Gln Tyr Ile Leu
            260                 265                 270
Arg Ala Ala Ile Lys Ala Leu Gly Ser Phe Arg Ser Asn Gly Asn
        275                 280                 285
Val Glu Leu Glu Leu Val Ala Arg Arg Ser Cys Leu Cys Leu Lys
    290                 295                 300
Tyr Val Gly Leu Gln
305

<210> SEQ ID NO 32
<211> LENGTH: 279
<212> TYPE: PRT
<213> ORGANISM: Physcomitrella patens

<400> SEQUENCE: 32

Met Ala Lys Asp Val Gly Val Glu Pro Gly Phe Pro Ser Lys Asp Tyr
1               5                   10                  15
Thr Asp Pro Pro Ala Pro Leu Ile Asp Ala Ser Glu Phe Gly Gln
                20                  25                  30
Trp Ser Phe Tyr Arg Ala Val Ile Ala Glu Phe Val Ala Thr Leu Leu
            35                  40                  45
Phe Leu Tyr Ile Thr Ile Ala Thr Val Ile Gly Ala Val Arg Asn Ala
        50                  55                  60
Gly Cys Asp Gly Val Gly Leu Leu Gly Ile Ala Trp Ala Phe Gly Gly
65                  70                  75                  80
Met Ile Phe Val Leu Val Tyr Cys Thr Ala Gly Ile Ser Gly Gly His
                85                  90                  95
Ile Asn Pro Ala Val Thr Phe Gly Leu Leu Leu Ala Arg Lys Ile Ser
                100                 105                 110
Leu Pro Arg Ala Leu Ala Tyr Met Ile Ala Gln Cys Leu Gly Ala Ile
            115                 120                 125
Cys Gly Ala Gly Leu Val Lys Gly Phe Gln Thr Ala Phe Tyr Met Arg
        130                 135                 140
Tyr Gly Gly Gly Ala Asn Ser Val Ala Gly Tyr Ser Ile Gly Thr
145                 150                 155                 160
Gly Leu Ala Ala Glu Ile Ile Gly Thr Phe Val Leu Val Tyr Thr Val
                165                 170                 175
Phe Ser Ala Thr Asp Pro Lys Arg Asn Ala Arg Asp Ser His Val Pro
```

```
                            180                 185                 190
Val Leu Ala Pro Leu Pro Ile Gly Phe Ala Val Phe Met Val His Leu
                195                 200                 205
Ala Thr Ile Pro Ile Thr Gly Thr Gly Ile Asn Pro Ala Arg Ser Phe
        210                 215                 220
Gly Ala Ala Val Ile Tyr Asn Arg Ser Lys Pro Trp Asp Asp His Trp
225                 230                 235                 240
Ile Phe Trp Val Gly Pro Phe Val Gly Ala Ala Leu Ala Ala Ala Tyr
                245                 250                 255
His Gln Tyr Val Leu Arg Ala Gly Pro Phe Lys Gln Leu Gly Ser Phe
                260                 265                 270
Arg Ser Ala Pro Ser Arg Val
            275

<210> SEQ ID NO 33
<211> LENGTH: 281
<212> TYPE: PRT
<213> ORGANISM: Spinacia oleracea

<400> SEQUENCE: 33

Met Ser Lys Glu Val Ser Glu Glu Ala Gln Ala His Gln His Gly Lys
1               5                   10                  15
Asp Tyr Val Asp Pro Pro Ala Pro Phe Phe Asp Leu Gly Glu Leu
            20                  25                  30
Lys Leu Trp Ser Phe Trp Arg Ala Ala Ile Ala Glu Phe Ile Ala Thr
        35                  40                  45
Leu Leu Phe Leu Tyr Ile Thr Val Ala Thr Val Ile Gly His Ser Lys
50                  55                  60
Glu Thr Val Val Cys Gly Ser Val Gly Leu Leu Gly Ile Ala Trp Ala
65                  70                  75                  80
Phe Gly Gly Met Ile Phe Val Leu Val Tyr Cys Thr Ala Gly Ile Ser
                85                  90                  95
Gly Gly His Ile Asn Pro Ala Val Thr Phe Gly Leu Phe Leu Ala Arg
            100                 105                 110
Lys Val Ser Leu Leu Arg Ala Leu Val Tyr Met Ile Ala Gln Cys Leu
        115                 120                 125
Gly Ala Ile Cys Gly Val Gly Leu Val Lys Ala Phe Met Lys Gly Pro
130                 135                 140
Tyr Asn Gln Phe Gly Gly Gly Ala Asn Ser Val Ala Leu Gly Tyr Asn
145                 150                 155                 160
Lys Gly Thr Ala Leu Gly Ala Glu Ile Ile Gly Thr Phe Val Leu Val
                165                 170                 175
Tyr Thr Val Phe Ser Ala Thr Asp Pro Lys Arg Ser Ala Arg Asp Ser
            180                 185                 190
His Val Pro Ile Leu Ala Pro Leu Pro Ile Gly Phe Ala Val Phe Met
        195                 200                 205
Val His Leu Ala Thr Ile Pro Ile Thr Gly Thr Gly Ile Asn Pro Ala
210                 215                 220
Arg Ser Phe Gly Ala Ala Val Ile Phe Asn Ser Asn Lys Val Trp Asp
225                 230                 235                 240
Asp Gln Trp Ile Phe Trp Val Gly Pro Phe Ile Gly Ala Ala Val Ala
                245                 250                 255
Ala Ala Tyr His Gln Tyr Val Leu Arg Ala Ala Ile Lys Ala Leu
            260                 265                 270
Gly Ser Phe Arg Ser Asn Pro Thr Asn
```

-continued

```
                275                 280

<210> SEQ ID NO 34
<211> LENGTH: 263
<212> TYPE: PRT
<213> ORGANISM: Homo sapiens

<400> SEQUENCE: 34

Met Trp Glu Leu Arg Ser Ala Ser Phe Trp Arg Ala Ile Phe Ala Glu
1               5                   10                  15

Phe Phe Ala Thr Leu Phe Tyr Val Phe Phe Gly Leu Gly Ser Ser Leu
            20                  25                  30

Arg Trp Ala Pro Gly Pro Leu His Val Leu Gln Val Ala Met Ala Phe
        35                  40                  45

Gly Leu Ala Leu Ala Thr Leu Val Gln Ser Val Gly His Ile Ser Gly
    50                  55                  60

Ala His Val Asn Pro Ala Val Thr Phe Ala Phe Leu Val Gly Ser Gln
65                  70                  75                  80

Met Ser Leu Leu Arg Ala Phe Cys Tyr Met Ala Ala Gln Leu Leu Gly
                85                  90                  95

Ala Val Ala Gly Ala Ala Val Leu Tyr Ser Val Thr Pro Pro Ala Val
            100                 105                 110

Arg Gly Asn Leu Ala Leu Asn Thr Leu His Pro Ala Val Ser Val Gly
        115                 120                 125

Gln Ala Thr Thr Val Glu Ile Phe Leu Thr Leu Gln Phe Val Leu Cys
    130                 135                 140

Ile Phe Ala Thr Tyr Asp Glu Arg Arg Asn Gly Gln Leu Gly Ser Val
145                 150                 155                 160

Ala Leu Ala Val Gly Phe Ser Leu Ala Leu Gly His Leu Phe Gly Met
                165                 170                 175

Tyr Tyr Thr Gly Ala Gly Met Asn Pro Ala Arg Ser Phe Ala Pro Ala
            180                 185                 190

Ile Leu Thr Gly Asn Phe Thr Asn His Trp Val Tyr Trp Val Gly Pro
        195                 200                 205

Ile Ile Gly Gly Gly Leu Gly Ser Leu Leu Tyr Asp Phe Leu Leu Phe
    210                 215                 220

Pro Arg Leu Lys Ser Ile Ser Glu Arg Leu Ser Val Leu Lys Gly Ala
225                 230                 235                 240

Lys Pro Asp Val Ser Asn Gly Gln Pro Glu Val Thr Gly Glu Pro Val
                245                 250                 255

Glu Leu Asn Thr Gln Ala Leu
            260

<210> SEQ ID NO 35
<211> LENGTH: 263
<212> TYPE: PRT
<213> ORGANISM: Bos taurus

<400> SEQUENCE: 35

Met Trp Glu Leu Arg Ser Ala Ser Phe Trp Arg Ala Ile Cys Ala Glu
1               5                   10                  15

Phe Phe Ala Ser Leu Phe Tyr Val Phe Phe Gly Leu Gly Ala Ser Leu
            20                  25                  30

Arg Trp Ala Pro Gly Pro Leu His Val Leu Gln Val Ala Leu Ala Phe
        35                  40                  45

Gly Leu Ala Leu Ala Thr Leu Val Gln Ala Val Gly His Ile Ser Gly
    50                  55                  60
```

```
Ala His Val Asn Pro Ala Val Thr Phe Ala Phe Leu Val Gly Ser Gln
 65                  70                  75                  80

Met Ser Leu Leu Arg Ala Ile Cys Tyr Met Val Ala Gln Leu Leu Gly
                 85                  90                  95

Ala Val Ala Gly Ala Ala Val Leu Tyr Ser Val Thr Pro Pro Ala Val
            100                 105                 110

Arg Gly Asn Leu Ala Leu Asn Thr Leu His Pro Gly Val Ser Val Gly
        115                 120                 125

Gln Ala Thr Ile Val Glu Ile Phe Leu Thr Leu Gln Phe Val Leu Cys
130                 135                 140

Ile Phe Ala Thr Tyr Asp Glu Arg Arg Asn Gly Arg Leu Gly Ser Val
145                 150                 155                 160

Ala Leu Ala Val Gly Phe Ser Leu Thr Leu Gly His Leu Phe Gly Met
                165                 170                 175

Tyr Tyr Thr Gly Ala Gly Met Asn Pro Ala Arg Ser Phe Ala Pro Ala
            180                 185                 190

Ile Leu Thr Arg Asn Phe Thr Asn His Trp Val Tyr Trp Val Gly Pro
        195                 200                 205

Val Ile Gly Ala Gly Leu Gly Ser Leu Leu Tyr Asp Phe Leu Leu Phe
210                 215                 220

Pro Arg Leu Lys Ser Val Ser Glu Arg Leu Ser Ile Leu Lys Gly Ser
225                 230                 235                 240

Arg Pro Ser Glu Ser Asn Gly Gln Pro Glu Val Thr Gly Glu Pro Val
                245                 250                 255

Glu Leu Lys Thr Gln Ala Leu
            260

<210> SEQ ID NO 36
<211> LENGTH: 262
<212> TYPE: PRT
<213> ORGANISM: Gallus gallus

<400> SEQUENCE: 36

Met Arg Glu Leu Arg Ser Ser Ser Phe Trp Arg Ala Ile Leu Ala Glu
1               5                   10                  15

Phe Leu Gly Ser Leu Leu Tyr Thr Leu Leu Gly Leu Gly Ala Ser Leu
            20                  25                  30

Arg Trp Ala Pro Gly Pro His Gly Val Leu Gly Ser Ala Leu Ala Phe
        35                  40                  45

Gly Leu Ala Gln Ala Thr Leu Val Gln Ala Leu Gly His Val Ser Gly
50                  55                  60

Gly His Ile Asn Pro Ala Ile Thr Leu Ala Phe Leu Leu Ala Ser Gln
 65                  70                  75                  80

Leu Ser Leu Pro Arg Ala Leu Gly Tyr Leu Leu Ala Gln Leu Leu Gly
                 85                  90                  95

Ala Leu Ala Gly Ala Gly Val Leu Tyr Gly Val Thr Pro Ala Ala Val
            100                 105                 110

Arg Gly Thr Leu Gly Leu Ser Ala Leu His Pro Ser Val Gly Pro Gly
        115                 120                 125

Gln Gly Thr Val Val Glu Leu Leu Leu Thr Ala Gln Phe Ile Leu Cys
130                 135                 140

Val Phe Ala Ser Phe Asp Asp Arg His Asp Gly Arg Pro Gly Ser Ala
145                 150                 155                 160

Ala Leu Pro Val Gly Phe Ser Leu Ala Leu Gly His Leu Phe Gly Ile
                165                 170                 175
```

```
Pro Phe Thr Gly Ala Gly Met Asn Pro Ala Arg Ser Phe Ala Pro Ala
            180                 185                 190

Val Ile Thr Arg Asn Phe Thr Asn His Trp Val Phe Trp Ala Gly Pro
        195                 200                 205

Leu Leu Gly Ala Ala Leu Ala Leu Leu Tyr Glu Leu Ala Leu Cys
    210                 215                 220

Pro Arg Ala Arg Ser Met Ala Glu Arg Leu Ala Val Leu Arg Gly Glu
225                 230                 235                 240

Pro Pro Ala Ala Ala Pro Pro Glu Pro Pro Ala Glu Pro Leu Glu
                245                 250                 255

Leu Lys Thr Gln Gly Leu
            260

<210> SEQ ID NO 37
<211> LENGTH: 262
<212> TYPE: PRT
<213> ORGANISM: Xenopus laevis

<400> SEQUENCE: 37

Trp Glu Phe Arg Ser Phe Ser Phe Trp Arg Ala Val Phe Ala Glu Phe
1               5                   10                  15

Phe Gly Thr Met Phe Tyr Val Phe Gly Leu Gly Ala Ser Leu Lys
            20                  25                  30

Trp Ala Ala Gly Pro Ala Asn Val Leu Val Ile Ala Leu Ala Phe Gly
        35                  40                  45

Leu Val Leu Ala Thr Met Val Gln Ser Ile Gly His Val Ser Gly Ala
50                  55                  60

His Ile Asn Pro Ala Val Thr Phe Ala Phe Leu Ile Gly Ser Gln Met
65                  70                  75                  80

Ser Leu Phe Arg Ala Ile Phe Tyr Ile Ala Ala Gln Leu Leu Gly Ala
                85                  90                  95

Val Ala Gly Ala Ala Val Leu Tyr Gly Val Thr Pro Ala Ala Ile Arg
            100                 105                 110

Gly Asn Leu Ala Leu Asn Thr Leu His Pro Gly Val Ser Leu Gly Gln
        115                 120                 125

Ala Thr Thr Val Glu Ile Phe Leu Thr Leu Gln Phe Val Leu Cys Ile
    130                 135                 140

Phe Ala Thr Tyr Asp Glu Arg Arg Asn Gly Arg Leu Gly Ser Val Ser
145                 150                 155                 160

Leu Ala Ile Gly Phe Ser Leu Thr Leu Gly His Leu Phe Gly Leu Tyr
                165                 170                 175

Tyr Thr Gly Ala Ser Met Asn Pro Ala Arg Ser Phe Ala Pro Ala Val
            180                 185                 190

Leu Thr Arg Asn Phe Thr Asn His Trp Val Tyr Trp Val Gly Pro Ile
        195                 200                 205

Ile Gly Gly Ala Leu Gly Gly Leu Val Tyr Asp Phe Ile Leu Phe Pro
    210                 215                 220

Arg Met Arg Gly Leu Ser Glu Arg Leu Ser Ile Leu Lys Gly Ala Arg
225                 230                 235                 240

Pro Ala Glu Pro Glu Gly Gln Gln Glu Ala Thr Gly Glu Pro Ile Glu
                245                 250                 255

Leu Lys Thr Gln Ser Leu
            260

<210> SEQ ID NO 38
```

<211> LENGTH: 271
<212> TYPE: PRT
<213> ORGANISM: Bos taurus

<400> SEQUENCE: 38

```
Met Ala Ser Glu Phe Lys Lys Lys Leu Phe Trp Arg Ala Val Val Ala
1               5                   10                  15

Glu Phe Leu Ala Met Ile Leu Phe Ile Phe Ile Ser Ile Gly Ser Ala
                20                  25                  30

Leu Gly Phe His Tyr Pro Ile Lys Ser Asn Gln Thr Thr Gly Ala Val
            35                  40                  45

Gln Asp Asn Val Lys Val Ser Leu Ala Phe Gly Leu Ser Ile Ala Thr
        50                  55                  60

Leu Ala Gln Ser Val Gly His Ile Ser Gly Ala His Leu Asn Pro Ala
65                  70                  75                  80

Val Thr Leu Gly Leu Leu Leu Ser Cys Gln Ile Ser Val Leu Arg Ala
                85                  90                  95

Ile Met Tyr Ile Ile Ala Gln Cys Val Gly Ala Ile Val Ala Thr Ala
                100                 105                 110

Ile Leu Ser Gly Ile Thr Ser Ser Leu Pro Asp Asn Ser Leu Gly Leu
            115                 120                 125

Asn Ala Leu Ala Pro Gly Val Asn Ser Gly Gln Gly Leu Gly Ile Glu
        130                 135                 140

Ile Ile Gly Thr Leu Gln Leu Val Leu Cys Val Leu Ala Thr Thr Asp
145                 150                 155                 160

Arg Arg Arg Arg Asp Leu Gly Gly Ser Gly Pro Leu Ala Ile Gly Phe
                165                 170                 175

Ser Val Ala Leu Gly His Leu Leu Ala Ile Asp Tyr Thr Gly Cys Gly
                180                 185                 190

Ile Asn Pro Ala Arg Ser Phe Gly Ser Ser Val Ile Thr His Asn Phe
            195                 200                 205

Gln Asp His Trp Ile Phe Trp Val Gly Pro Phe Ile Gly Ala Ala Leu
        210                 215                 220

Ala Val Leu Ile Tyr Asp Phe Ile Leu Ala Pro Arg Ser Ser Asp Leu
225                 230                 235                 240

Thr Asp Arg Val Lys Val Trp Thr Ser Gly Gln Val Glu Glu Tyr Asp
                245                 250                 255

Leu Asp Ala Asp Asp Ile Asn Ser Arg Val Glu Met Lys Pro Lys
                260                 265                 270
```

<210> SEQ ID NO 39
<211> LENGTH: 269
<212> TYPE: PRT
<213> ORGANISM: Homo sapiens

<400> SEQUENCE: 39

```
Met Ala Ser Glu Phe Lys Lys Lys Leu Phe Trp Arg Ala Val Val Ala
1               5                   10                  15

Glu Phe Leu Ala Thr Thr Leu Phe Val Phe Ile Ser Ile Gly Ser Ala
                20                  25                  30

Leu Gly Phe Lys Tyr Pro Val Gly Asn Asn Gln Thr Thr Val Gln Asp
            35                  40                  45

Asn Val Lys Val Ser Leu Ala Phe Gly Leu Ser Ile Ala Thr Leu Ala
        50                  55                  60

Gln Ser Val Gly His Ile Ser Gly Ala His Leu Asn Pro Ala Val Thr
65                  70                  75                  80
```

```
Leu Gly Leu Leu Leu Ser Cys Gln Ile Ser Ile Phe Arg Ala Leu Met
                85                  90                  95

Tyr Ile Ile Ala Gln Cys Val Gly Ala Ile Val Ala Thr Ala Ile Leu
            100                 105                 110

Ser Gly Ile Thr Ser Ser Leu Thr Gly Asn Ser Leu Gly Arg Asn Asp
        115                 120                 125

Leu Ala Asp Gly Val Asn Ser Gly Gln Gly Leu Gly Ile Glu Ile Ile
    130                 135                 140

Gly Thr Leu Gln Leu Val Leu Cys Val Leu Ala Thr Thr Asp Arg Arg
145                 150                 155                 160

Arg Arg Asp Leu Gly Gly Ser Ala Pro Leu Ala Ile Gly Leu Ser Val
                165                 170                 175

Ala Leu Gly His Leu Leu Ala Ile Asp Tyr Thr Gly Cys Gly Ile Asn
            180                 185                 190

Pro Ala Arg Ser Phe Gly Ser Ala Val Ile Thr His Asn Phe Ser Asn
        195                 200                 205

His Trp Ile Phe Trp Val Gly Pro Phe Ile Gly Gly Ala Leu Ala Val
    210                 215                 220

Leu Ile Tyr Asp Phe Ile Leu Ala Pro Arg Ser Ser Asp Leu Thr Asp
225                 230                 235                 240

Arg Val Lys Val Trp Thr Ser Gly Gln Val Glu Glu Tyr Asp Leu Asp
                245                 250                 255

Ala Asp Asp Ile Asn Ser Arg Val Glu Met Lys Pro Lys
            260                 265

<210> SEQ ID NO 40
<211> LENGTH: 271
<212> TYPE: PRT
<213> ORGANISM: Homo sapiens

<400> SEQUENCE: 40

Met Trp Glu Leu Arg Ser Ile Ala Phe Ser Arg Ala Val Phe Ala Glu
1               5                   10                  15

Phe Leu Ala Thr Leu Leu Phe Val Phe Phe Gly Leu Gly Ser Ala Leu
            20                  25                  30

Asn Trp Pro Gln Ala Leu Pro Ser Val Leu Gln Ile Ala Met Ala Phe
        35                  40                  45

Gly Leu Gly Ile Gly Thr Leu Val Gln Ala Leu Gly His Ile Ser Gly
    50                  55                  60

Ala His Ile Asn Pro Ala Val Thr Val Ala Cys Leu Val Gly Cys His
65                  70                  75                  80

Val Ser Val Leu Arg Ala Ala Phe Tyr Val Ala Ala Gln Leu Leu Gly
                85                  90                  95

Ala Val Ala Gly Ala Ala Leu Leu His Glu Ile Thr Pro Ala Asp Ile
            100                 105                 110

Arg Gly Asp Leu Ala Val Asn Ala Leu Ser Asn Ser Thr Thr Ala Gly
        115                 120                 125

Gln Ala Val Thr Val Glu Leu Phe Leu Thr Leu Gln Leu Val Leu Cys
    130                 135                 140

Ile Phe Ala Ser Thr Asp Glu Arg Arg Gly Glu Asn Pro Gly Thr Pro
145                 150                 155                 160

Ala Leu Ser Ile Gly Phe Ser Val Ala Leu Gly His Leu Leu Gly Ile
                165                 170                 175

His Tyr Thr Gly Cys Ser Met Asn Pro Ala Arg Ser Leu Ala Pro Ala
            180                 185                 190
```

```
Val Val Thr Gly Lys Phe Asp Asp His Trp Val Phe Trp Ile Gly Pro
            195                 200                 205

Leu Val Gly Ala Ile Leu Gly Ser Leu Leu Tyr Asn Tyr Val Leu Phe
        210                 215                 220

Pro Pro Ala Lys Ser Leu Ser Glu Arg Leu Ala Val Leu Lys Gly Leu
225                 230                 235                 240

Glu Pro Asp Thr Asp Trp Glu Glu Arg Glu Val Arg Arg Gln Ser
                245                 250                 255

Val Glu Leu His Ser Pro Gln Ser Leu Pro Arg Gly Thr Lys Ala
            260                 265                 270

<210> SEQ ID NO 41
<211> LENGTH: 323
<212> TYPE: PRT
<213> ORGANISM: Homo sapiens

<400> SEQUENCE: 41

Met Ser Asp Arg Pro Thr Ala Arg Arg Trp Gly Lys Cys Gly Pro Leu
1               5                   10                  15

Cys Thr Arg Glu Asn Ile Met Val Ala Phe Lys Gly Val Trp Thr Gln
            20                  25                  30

Ala Phe Trp Lys Ala Val Thr Ala Glu Phe Leu Ala Met Leu Ile Phe
        35                  40                  45

Val Leu Leu Ser Leu Gly Ser Thr Ile Asn Trp Gly Gly Thr Glu Lys
    50                  55                  60

Pro Leu Pro Val Asp Met Val Leu Ile Ser Leu Cys Phe Gly Leu Ser
65                  70                  75                  80

Ile Ala Thr Met Val Gln Cys Phe Gly His Ile Ser Gly Gly His Ile
                85                  90                  95

Asn Pro Ala Val Thr Val Ala Met Val Cys Thr Arg Lys Ile Ser Ile
            100                 105                 110

Ala Lys Ser Val Phe Tyr Ile Ala Ala Gln Cys Leu Gly Ala Ile Ile
        115                 120                 125

Gly Ala Gly Ile Leu Tyr Leu Val Thr Pro Pro Ser Val Val Gly Gly
    130                 135                 140

Leu Gly Val Thr Met Val His Gly Asn Leu Thr Ala Gly His Gly Leu
145                 150                 155                 160

Leu Val Glu Leu Ile Ile Thr Phe Gln Leu Val Phe Thr Ile Phe Ala
                165                 170                 175

Ser Cys Asp Ser Lys Arg Thr Asp Val Thr Gly Ser Ile Ala Leu Ala
            180                 185                 190

Ile Gly Phe Ser Val Ala Ile Gly His Leu Phe Ala Ile Asn Tyr Thr
        195                 200                 205

Gly Ala Ser Met Asn Pro Ala Arg Ser Phe Gly Pro Ala Val Ile Met
    210                 215                 220

Gly Asn Trp Glu Asn His Trp Ile Tyr Trp Val Gly Pro Ile Ile Gly
225                 230                 235                 240

Ala Val Leu Ala Gly Gly Leu Tyr Glu Tyr Val Phe Cys Pro Asp Val
                245                 250                 255

Glu Phe Lys Arg Arg Phe Lys Glu Ala Phe Ser Lys Ala Ala Gln Gln
            260                 265                 270

Thr Lys Gly Ser Tyr Met Glu Val Glu Asp Asn Arg Ser Gln Val Glu
        275                 280                 285

Thr Asp Asp Leu Ile Leu Lys Pro Gly Val Val His Val Ile Asp Val
    290                 295                 300
```

```
Asp Arg Gly Glu Glu Lys Lys Gly Lys Asp Gln Ser Gly Glu Val Leu
305                 310                 315                 320

Ser Ser Val

<210> SEQ ID NO 42
<211> LENGTH: 265
<212> TYPE: PRT
<213> ORGANISM: Homo sapiens

<400> SEQUENCE: 42

Met Lys Lys Glu Val Cys Ser Val Ala Phe Leu Lys Ala Val Phe Ala
1               5                   10                  15

Glu Phe Leu Ala Thr Leu Ile Phe Val Phe Phe Gly Leu Gly Ser Ala
            20                  25                  30

Leu Lys Trp Pro Ser Ala Leu Pro Thr Ile Leu Gln Ile Ala Leu Ala
        35                  40                  45

Phe Gly Leu Ala Ile Gly Thr Leu Ala Gln Ala Leu Gly Pro Val Ser
    50                  55                  60

Gly Gly His Ile Asn Pro Ala Ile Thr Leu Ala Leu Leu Val Gly Asn
65                  70                  75                  80

Gln Ile Ser Leu Leu Arg Ala Phe Phe Tyr Val Ala Ala Gln Leu Val
                85                  90                  95

Gly Ala Ile Ala Gly Ala Gly Ile Leu Tyr Gly Val Ala Pro Leu Asn
            100                 105                 110

Ala Arg Gly Asn Leu Ala Val Asn Ala Leu Asn Asn Asn Thr Thr Gln
        115                 120                 125

Gly Gln Ala Met Val Val Glu Leu Ile Leu Thr Phe Gln Leu Ala Leu
    130                 135                 140

Cys Ile Phe Ala Ser Thr Asp Ser Arg Arg Thr Ser Pro Val Gly Ser
145                 150                 155                 160

Pro Ala Leu Ser Ile Gly Leu Ser Val Thr Leu Gly His Leu Val Gly
                165                 170                 175

Ile Tyr Phe Thr Gly Cys Ser Met Asn Pro Ala Arg Ser Phe Gly Pro
            180                 185                 190

Ala Val Val Met Asn Arg Phe Ser Pro Ala His Trp Val Phe Trp Val
        195                 200                 205

Gly Pro Ile Val Gly Ala Val Leu Ala Ala Ile Leu Tyr Phe Tyr Leu
    210                 215                 220

Leu Phe Pro Asn Ser Leu Ser Leu Ser Glu Arg Val Ala Ile Ile Lys
225                 230                 235                 240

Gly Thr Tyr Glu Pro Asp Glu Asp Trp Glu Glu Gln Arg Glu Glu Arg
                245                 250                 255

Lys Lys Thr Met Glu Leu Thr Thr Arg
            260                 265

<210> SEQ ID NO 43
<211> LENGTH: 282
<212> TYPE: PRT
<213> ORGANISM: Homo sapiens

<400> SEQUENCE: 43

Met Asp Ala Glu Val Pro Gly Gly Arg Gly Trp Ala Ser Met Leu Ala
1               5                   10                  15

Cys Arg Leu Trp Lys Ala Ile Ser Arg Ala Leu Phe Ala Glu Phe Leu
            20                  25                  30

Ala Thr Gly Leu Tyr Val Phe Phe Gly Val Gly Ser Val Met Arg Trp
        35                  40                  45
```

Pro Thr Ala Leu Pro Ser Val Leu Gln Ile Ala Ile Thr Phe Asn Leu
    50                  55                  60

Val Thr Ala Met Ala Val Gln Val Thr Trp Lys Thr Ser Gly Ala His
65                  70                  75                  80

Ala Asn Pro Ala Val Thr Leu Ala Phe Leu Val Gly Ser His Ile Ser
                85                  90                  95

Leu Pro Arg Ala Val Ala Tyr Val Ala Gln Leu Val Gly Ala Thr
            100                 105                 110

Val Gly Ala Ala Leu Leu Tyr Gly Val Met Pro Gly Asp Ile Arg Glu
        115                 120                 125

Thr Leu Gly Ile Asn Val Val Arg Asn Ser Val Ser Thr Gly Gln Ala
    130                 135                 140

Val Ala Val Glu Leu Leu Leu Thr Leu Gln Leu Val Leu Cys Val Phe
145                 150                 155                 160

Ala Ser Thr Asp Ser Arg Gln Thr Ser Gly Ser Pro Ala Thr Met Ile
                165                 170                 175

Gly Ile Ser Trp Ala Leu Gly His Leu Ile Gly Ile Leu Phe Thr Gly
            180                 185                 190

Cys Ser Met Asn Pro Ala Arg Ser Phe Gly Pro Ala Ile Ile Ile Gly
        195                 200                 205

Lys Phe Thr Val His Trp Val Phe Trp Val Gly Pro Leu Met Gly Ala
210                 215                 220

Leu Leu Ala Ser Leu Ile Tyr Asn Phe Val Leu Phe Pro Asp Thr Lys
225                 230                 235                 240

Thr Leu Ala Gln Arg Leu Ala Ile Leu Thr Gly Thr Val Glu Val Gly
                245                 250                 255

Thr Gly Ala Arg Ala Gly Ala Glu Pro Leu Lys Lys Glu Ser Gln Pro
            260                 265                 270

Gly Ser Gly Ala Val Glu Met Glu Ser Val
        275                 280

<210> SEQ ID NO 44
<211> LENGTH: 255
<212> TYPE: PRT
<213> ORGANISM: Homo sapiens

<400> SEQUENCE: 44

Met Cys Glu Pro Glu Phe Gly Asn Asp Lys Ala Arg Glu Pro Ser Val
1               5                   10                  15

Gly Gly Arg Trp Arg Val Ser Trp Tyr Glu Arg Phe Val Gln Pro Cys
            20                  25                  30

Leu Val Glu Leu Leu Gly Ser Ala Leu Phe Ile Phe Ile Gly Cys Leu
        35                  40                  45

Ser Val Ile Glu Asn Gly Thr Asp Thr Gly Leu Leu Gln Pro Ala Leu
    50                  55                  60

Ala His Gly Leu Ala Leu Gly Leu Val Ile Ala Thr Leu Gly Asn Ile
65                  70                  75                  80

Ser Gly Gly His Phe Asn Pro Ala Val Ser Leu Ala Ala Met Leu Ile
                85                  90                  95

Gly Gly Leu Asn Leu Val Met Leu Leu Pro Tyr Trp Val Ser Gln Leu
            100                 105                 110

Leu Gly Gly Met Leu Gly Ala Ala Leu Ala Lys Ala Val Ser Pro Glu
        115                 120                 125

Glu Arg Phe Trp Asn Ala Ser Gly Ala Ala Phe Val Thr Val Gln Glu
    130                 135                 140

```
Gln Gly Gln Val Ala Gly Ala Leu Val Ala Glu Ile Ile Leu Thr Thr
145                 150                 155                 160

Leu Leu Ala Leu Ala Val Cys Met Gly Ala Ile Asn Glu Lys Thr Lys
                165                 170                 175

Gly Pro Leu Ala Pro Phe Ser Ile Gly Phe Ala Val Thr Val Asp Ile
            180                 185                 190

Leu Ala Gly Gly Pro Val Ser Gly Gly Cys Met Asn Pro Ala Arg Ala
        195                 200                 205

Phe Gly Pro Ala Val Val Ala Asn His Trp Asn Phe His Trp Ile Tyr
    210                 215                 220

Trp Leu Gly Pro Leu Leu Ala Gly Leu Leu Val Gly Leu Leu Ile Arg
225                 230                 235                 240

Cys Phe Ile Gly Asp Gly Lys Thr Arg Leu Ile Leu Lys Ala Arg
                245                 250                 255

<210> SEQ ID NO 45
<211> LENGTH: 231
<212> TYPE: PRT
<213> ORGANISM: Escherichia coli

<400> SEQUENCE: 45

Met Phe Arg Lys Leu Ala Ala Glu Cys Phe Gly Thr Phe Trp Leu Val
1               5                   10                  15

Phe Gly Gly Cys Gly Ser Ala Val Leu Ala Ala Gly Phe Pro Glu Leu
            20                  25                  30

Gly Ile Gly Phe Ala Gly Val Ala Leu Ala Phe Gly Leu Thr Val Leu
        35                  40                  45

Thr Met Ala Phe Ala Val Gly His Ile Ser Gly Gly His Phe Asn Pro
50                  55                  60

Ala Val Thr Ile Gly Leu Trp Ala Gly Gly Arg Phe Pro Ala Lys Glu
65                  70                  75                  80

Val Val Gly Tyr Val Ile Ala Gln Val Val Gly Gly Ile Val Ala Ala
                85                  90                  95

Ala Leu Leu Tyr Leu Ile Ala Ser Gly Lys Thr Gly Phe Asp Ala Ala
            100                 105                 110

Ala Ser Gly Phe Ala Ser Asn Gly Tyr Gly Glu His Ser Pro Gly Gly
        115                 120                 125

Tyr Ser Met Leu Ser Ala Leu Val Val Glu Leu Val Leu Ser Ala Gly
130                 135                 140

Phe Leu Leu Val Ile His Gly Ala Thr Asp Lys Phe Ala Pro Ala Gly
145                 150                 155                 160

Phe Ala Pro Ile Ala Ile Gly Leu Ala Leu Thr Leu Ile His Leu Ile
                165                 170                 175

Ser Ile Pro Val Thr Asn Thr Ser Val Asn Pro Ala Arg Ser Thr Ala
            180                 185                 190

Val Ala Ile Phe Gln Gly Gly Trp Ala Leu Glu Gln Leu Trp Phe Phe
        195                 200                 205

Trp Val Val Pro Ile Val Gly Gly Ile Ile Gly Gly Leu Ile Tyr Arg
210                 215                 220

Thr Leu Leu Glu Lys Arg Asp
225                 230

<210> SEQ ID NO 46
<211> LENGTH: 271
<212> TYPE: PRT
<213> ORGANISM: Homo sapiens
```

<400> SEQUENCE: 46

```
Met Ser Pro Leu Leu Gly Leu Arg Ser Glu Leu Gln Asp Thr Cys Thr
1               5                   10                  15

Ser Leu Gly Leu Met Leu Ser Val Val Leu Leu Met Gly Leu Ala Arg
            20                  25                  30

Val Val Ala Arg Gln Gln Leu His Arg Pro Val Ala His Ala Phe Val
        35                  40                  45

Leu Glu Phe Leu Ala Thr Phe Gln Leu Cys Cys Cys Thr His Glu Leu
    50                  55                  60

Gln Leu Leu Ser Glu Gln His Pro Ala His Pro Thr Trp Thr Leu Thr
65                  70                  75                  80

Leu Val Tyr Phe Phe Ser Leu Val His Gly Leu Thr Leu Val Gly Thr
                85                  90                  95

Ser Ser Asn Pro Cys Gly Val Met Met Gln Met Met Leu Gly Gly Met
            100                 105                 110

Ser Pro Glu Thr Gly Ala Val Arg Leu Leu Ala Gln Leu Val Ser Ala
        115                 120                 125

Leu Cys Ser Arg Tyr Cys Thr Ser Ala Leu Trp Ser Leu Gly Leu Thr
130                 135                 140

Gln Tyr His Val Ser Glu Arg Ser Phe Ala Cys Lys Asn Pro Ile Arg
145                 150                 155                 160

Val Asp Leu Leu Lys Ala Val Ile Thr Glu Ala Val Cys Ser Phe Leu
                165                 170                 175

Phe His Ser Ala Leu Leu His Phe Gln Glu Val Arg Thr Lys Leu Arg
            180                 185                 190

Ile His Leu Leu Ala Ala Leu Ile Thr Phe Leu Val Tyr Ala Gly Gly
        195                 200                 205

Ser Leu Thr Gly Ala Val Phe Asn Pro Ala Leu Ala Leu Ser Leu His
    210                 215                 220

Phe Met Cys Phe Asp Glu Ala Phe Pro Gln Phe Phe Ile Val Tyr Trp
225                 230                 235                 240

Leu Ala Pro Ser Leu Gly Ile Leu Leu Met Ile Leu Met Phe Ser Phe
                245                 250                 255

Phe Leu Pro Trp Leu His Asn Asn His Thr Ile Asn Lys Lys Glu
            260                 265                 270
```

<210> SEQ ID NO 47
<211> LENGTH: 295
<212> TYPE: PRT
<213> ORGANISM: Homo sapiens

<400> SEQUENCE: 47

```
Met Ala Gly Leu Asn Val Ser Leu Ser Phe Phe Phe Ala Thr Phe Ala
1               5                   10                  15

Leu Cys Glu Ala Ala Arg Arg Ala Ser Lys Ala Leu Leu Pro Val Gly
            20                  25                  30

Ala Tyr Glu Val Phe Ala Arg Glu Ala Met Arg Thr Leu Val Glu Leu
        35                  40                  45

Gly Pro Trp Ala Gly Asp Phe Gly Pro Asp Leu Leu Leu Thr Leu Leu
    50                  55                  60

Phe Leu Leu Phe Leu Ala His Gly Val Thr Leu Asp Gly Ala Ser Ala
65                  70                  75                  80

Asn Pro Thr Val Ser Leu Gln Glu Phe Leu Met Ala Glu Gln Ser Leu
                85                  90                  95
```

```
Pro Gly Thr Leu Leu Lys Leu Ala Ala Gln Gly Leu Gly Met Gln Ala
            100                 105                 110

Ala Cys Thr Leu Met Arg Leu Cys Trp Ala Trp Glu Leu Ser Asp Leu
        115                 120                 125

His Leu Leu Gln Ser Leu Met Ala Gln Ser Cys Ser Ser Ala Leu Arg
    130                 135                 140

Thr Ser Val Pro His Gly Ala Leu Val Glu Ala Ala Cys Ala Phe Cys
145                 150                 155                 160

Phe His Leu Thr Leu Leu His Leu Arg His Ser Pro Pro Ala Tyr Ser
                165                 170                 175

Gly Pro Ala Val Ala Leu Leu Val Thr Val Thr Ala Tyr Thr Ala Gly
            180                 185                 190

Pro Phe Thr Ser Ala Phe Phe Asn Pro Ala Leu Ala Ala Ser Val Thr
        195                 200                 205

Phe Ala Cys Ser Gly His Thr Leu Leu Glu Tyr Val Gln Val Tyr Trp
    210                 215                 220

Leu Gly Pro Leu Thr Gly Met Val Leu Ala Val Leu Leu His Gln Gly
225                 230                 235                 240

Arg Leu Pro His Leu Phe Gln Arg Asn Leu Phe Tyr Gly Gln Lys Asn
                245                 250                 255

Lys Tyr Arg Ala Pro Arg Gly Lys Pro Ala Pro Ala Ser Gly Asp Thr
            260                 265                 270

Gln Thr Pro Ala Lys Gly Ser Ser Val Arg Glu Pro Gly Arg Ser Gly
        275                 280                 285

Val Glu Gly Pro His Ser Ser
    290                 295

<210> SEQ ID NO 48
<211> LENGTH: 281
<212> TYPE: PRT
<213> ORGANISM: Escherichia coli

<400> SEQUENCE: 48

Met Ser Gln Thr Ser Thr Leu Lys Gly Gln Cys Ile Ala Glu Phe Leu
1               5                   10                  15

Gly Thr Gly Leu Leu Ile Phe Phe Gly Val Gly Cys Val Ala Ala Leu
            20                  25                  30

Lys Val Ala Gly Ala Ser Phe Gly Gln Trp Glu Ile Ser Val Ile Trp
        35                  40                  45

Gly Leu Gly Val Ala Met Ala Ile Tyr Leu Thr Ala Gly Val Ser Gly
    50                  55                  60

Ala His Leu Asn Pro Ala Val Thr Ile Ala Leu Trp Leu Phe Ala Cys
65                  70                  75                  80

Phe Asp Lys Arg Lys Val Ile Pro Phe Ile Val Ser Gln Val Ala Gly
                85                  90                  95

Ala Phe Cys Ala Ala Ala Leu Val Tyr Gly Leu Tyr Tyr Asn Leu Phe
            100                 105                 110

Phe Asp Phe Glu Gln Thr His His Ile Val Arg Gly Ser Ile Glu Ser
        115                 120                 125

Val Asp Leu Ala Gly Thr Phe Ser Thr Tyr Pro Asn Pro His Ile Asn
    130                 135                 140

Phe Val Gln Ala Phe Ala Val Glu Met Val Ile Thr Ala Ile Leu Ile
145                 150                 155                 160

Gly Leu Ile Leu Ala Leu Thr Asp Asp Gly Asn Gly Val Pro Arg Gly
                165                 170                 175
```

```
Pro Leu Ala Pro Leu Leu Ile Gly Leu Leu Ile Ala Val Ile Gly Ala
            180                 185                 190

Ser Met Gly Pro Leu Thr Gly Phe Ala Met Asn Pro Ala Arg Asp Phe
        195                 200                 205

Gly Pro Lys Val Phe Ala Trp Leu Ala Gly Trp Gly Asn Val Ala Phe
    210                 215                 220

Thr Gly Gly Arg Asp Ile Pro Tyr Phe Leu Val Pro Leu Phe Ser Pro
225                 230                 235                 240

Ile Val Gly Ala Ile Val Gly Ala Phe Ala Tyr Arg Lys Leu Ile Gly
                245                 250                 255

Arg His Leu Pro Cys Asp Ile Cys Val Val Glu Glu Lys Glu Thr Thr
                260                 265                 270

Thr Pro Ser Glu Gln Lys Ala Ser Leu
        275                 280
```

<210> SEQ ID NO 49
<211> LENGTH: 292
<212> TYPE: PRT
<213> ORGANISM: Homo sapiens

<400> SEQUENCE: 49

```
Met Gly Arg Gln Lys Glu Leu Val Ser Arg Cys Gly Glu Met Leu His
1               5                   10                  15

Ile Arg Tyr Arg Leu Leu Arg Gln Ala Leu Ala Glu Cys Leu Gly Thr
                20                  25                  30

Leu Ile Leu Val Met Phe Gly Cys Gly Ser Val Ala Gln Val Val Leu
            35                  40                  45

Ser Arg Gly Thr His Gly Gly Phe Leu Thr Ile Asn Leu Ala Phe Gly
    50                  55                  60

Phe Ala Val Thr Leu Gly Ile Leu Ile Ala Gly Gln Val Ser Gly Ala
65                  70                  75                  80

His Leu Asn Pro Ala Val Thr Phe Ala Met Cys Phe Leu Ala Arg Glu
                85                  90                  95

Pro Trp Ile Lys Leu Pro Ile Tyr Thr Leu Ala Gln Thr Leu Gly Ala
                100                 105                 110

Phe Leu Gly Ala Gly Ile Val Phe Gly Leu Tyr Tyr Asp Ala Ile Trp
            115                 120                 125

His Phe Ala Asp Asn Gln Leu Phe Val Ser Gly Pro Asn Gly Thr Ala
    130                 135                 140

Gly Ile Phe Ala Thr Tyr Pro Ser Gly His Leu Asp Met Ile Asn Gly
145                 150                 155                 160

Phe Phe Asp Gln Phe Ile Gly Thr Ala Ser Leu Ile Val Cys Val Leu
                165                 170                 175

Ala Ile Val Asp Pro Tyr Asn Asn Pro Val Pro Arg Gly Leu Glu Ala
                180                 185                 190

Phe Thr Val Gly Leu Val Val Leu Val Ile Gly Thr Ser Met Gly Phe
            195                 200                 205

Asn Ser Gly Tyr Ala Val Asn Pro Ala Arg Asp Phe Gly Pro Arg Leu
    210                 215                 220

Phe Thr Ala Leu Ala Gly Trp Gly Ser Ala Val Phe Thr Thr Gly Gln
225                 230                 235                 240

His Trp Trp Trp Val Pro Ile Val Ser Pro Leu Leu Gly Ser Ile Ala
                245                 250                 255

Gly Val Phe Val Tyr Gln Leu Met Ile Gly Cys His Leu Glu Gln Pro
                260                 265                 270
```

```
Pro Pro Ser Asn Glu Glu Asn Val Lys Leu Ala His Val Lys His
        275                 280                 285
Lys Glu Gln Ile
    290

<210> SEQ ID NO 50
<211> LENGTH: 342
<212> TYPE: PRT
<213> ORGANISM: Homo sapiens

<400> SEQUENCE: 50

Met Val Gln Ala Ser Gly His Arg Arg Ser Thr Arg Gly Ser Lys Met
1               5                   10                  15
Val Ser Trp Ser Val Ile Ala Lys Ile Gln Glu Ile Leu Gln Arg Lys
            20                  25                  30
Met Val Arg Glu Phe Leu Ala Glu Phe Met Ser Thr Tyr Val Met Met
        35                  40                  45
Val Phe Gly Leu Gly Ser Val Ala His Met Val Leu Asn Lys Lys Tyr
    50                  55                  60
Gly Ser Tyr Leu Gly Val Asn Leu Gly Phe Gly Phe Gly Val Thr Met
65                  70                  75                  80
Gly Val His Val Ala Gly Arg Ile Ser Gly Ala His Met Asn Ala Ala
                85                  90                  95
Val Thr Phe Ala Asn Cys Ala Leu Gly Arg Val Pro Trp Arg Lys Phe
            100                 105                 110
Pro Val Tyr Val Leu Gly Gln Phe Leu Gly Ser Phe Leu Ala Ala Ala
        115                 120                 125
Thr Ile Tyr Ser Leu Phe Tyr Thr Ala Ile Leu His Phe Ser Gly Gly
    130                 135                 140
Gln Leu Met Val Thr Gly Pro Val Ala Thr Ala Gly Ile Phe Ala Thr
145                 150                 155                 160
Tyr Leu Pro Asp His Met Thr Leu Trp Arg Gly Phe Leu Asn Glu Ala
                165                 170                 175
Trp Leu Thr Gly Met Leu Gln Leu Cys Leu Phe Ala Ile Thr Asp Gln
            180                 185                 190
Glu Asn Asn Pro Ala Leu Pro Gly Thr Glu Ala Leu Val Ile Gly Ile
        195                 200                 205
Leu Val Val Ile Ile Gly Val Ser Leu Gly Met Asn Thr Gly Tyr Ala
    210                 215                 220
Ile Asn Pro Ser Arg Asp Leu Pro Pro Arg Ile Phe Thr Phe Ile Ala
225                 230                 235                 240
Gly Trp Gly Lys Gln Val Phe Ser Asn Gly Glu Asn Trp Trp Trp Val
                245                 250                 255
Pro Val Val Ala Pro Leu Leu Gly Ala Tyr Leu Gly Gly Ile Ile Tyr
            260                 265                 270
Leu Val Phe Ile Gly Ser Thr Ile Pro Arg Glu Pro Leu Lys Leu Glu
        275                 280                 285
Asp Ser Val Ala Tyr Glu Asp His Gly Ile Thr Val Leu Pro Lys Met
    290                 295                 300
Gly Ser His Glu Pro Thr Ile Ser Pro Leu Thr Pro Val Ser Val Ser
305                 310                 315                 320
Pro Ala Asn Arg Ser Ser Val His Pro Ala Pro Leu His Glu Ser
                325                 330                 335
Met Ala Leu Glu His Phe
            340
```

-continued

<210> SEQ ID NO 51
<211> LENGTH: 295
<212> TYPE: PRT
<213> ORGANISM: Homo sapiens

<400> SEQUENCE: 51

Met Gln Pro Glu Gly Ala Glu Lys Gly Lys Ser Phe Lys Gln Arg Leu
1               5                   10                  15

Val Leu Lys Ser Ser Leu Ala Lys Glu Thr Leu Ser Glu Phe Leu Gly
            20                  25                  30

Thr Phe Ile Leu Ile Val Leu Gly Cys Gly Cys Val Ala Gln Ala Ile
        35                  40                  45

Leu Ser Arg Gly Arg Phe Gly Gly Val Ile Thr Ile Asn Val Gly Phe
    50                  55                  60

Ser Met Ala Val Ala Met Ala Ile Tyr Val Ala Gly Gly Val Ser Gly
65                  70                  75                  80

Gly His Ile Asn Pro Ala Val Ser Leu Ala Met Cys Leu Phe Gly Arg
                85                  90                  95

Met Lys Trp Phe Lys Leu Pro Phe Tyr Val Gly Ala Gln Phe Leu Gly
            100                 105                 110

Ala Phe Val Gly Ala Ala Thr Val Phe Gly Ile Tyr Tyr Asp Gly Leu
        115                 120                 125

Met Ser Phe Ala Gly Gly Lys Leu Leu Ile Val Gly Glu Asn Ala Thr
    130                 135                 140

Ala His Ile Phe Ala Thr Tyr Pro Ala Pro Tyr Leu Ser Leu Ala Asn
145                 150                 155                 160

Ala Phe Ala Asp Gln Val Val Ala Thr Met Ile Leu Leu Ile Ile Val
                165                 170                 175

Phe Ala Ile Phe Asp Ser Arg Asn Leu Gly Ala Pro Arg Gly Leu Glu
            180                 185                 190

Pro Ile Ala Ile Gly Leu Leu Ile Ile Val Ile Ala Ser Ser Leu Gly
        195                 200                 205

Leu Asn Ser Gly Cys Ala Met Asn Pro Ala Arg Asp Leu Ser Pro Arg
    210                 215                 220

Leu Phe Thr Ala Leu Ala Gly Trp Gly Phe Glu Val Phe Arg Ala Gly
225                 230                 235                 240

Asn Asn Phe Trp Trp Ile Pro Val Val Gly Pro Leu Val Gly Ala Val
                245                 250                 255

Ile Gly Gly Leu Ile Tyr Val Leu Val Ile Glu Ile His His Pro Glu
            260                 265                 270

Pro Asp Ser Val Phe Lys Ala Glu Gln Ser Glu Asp Lys Pro Glu Lys
        275                 280                 285

Tyr Glu Leu Ser Val Ile Met
    290                 295

<210> SEQ ID NO 52
<211> LENGTH: 301
<212> TYPE: PRT
<213> ORGANISM: Homo sapiens

<400> SEQUENCE: 52

Met Val Phe Thr Gln Ala Pro Ala Glu Ile Met Gly His Leu Arg Ile
1               5                   10                  15

Arg Ser Leu Leu Ala Arg Gln Cys Leu Ala Glu Phe Leu Gly Val Phe
            20                  25                  30

Val Leu Met Leu Leu Thr Gln Gly Ala Val Ala Gln Ala Val Thr Ser

```
                   35                  40                  45
Gly Glu Thr Lys Gly Asn Phe Phe Thr Met Phe Leu Ala Gly Ser Leu
 50                  55                  60

Ala Val Thr Ile Ala Ile Tyr Val Gly Gly Asn Val Ser Gly Ala His
 65                  70                  75                  80

Leu Asn Pro Ala Phe Ser Leu Ala Met Cys Ile Val Gly Arg Leu Pro
                 85                  90                  95

Trp Val Lys Leu Pro Ile Tyr Ile Leu Val Gln Leu Leu Ser Ala Phe
                100                 105                 110

Cys Ala Ser Gly Ala Thr Tyr Val Leu Tyr His Asp Ala Leu Gln Asn
                115                 120                 125

Tyr Thr Gly Gly Asn Leu Thr Val Thr Gly Pro Lys Glu Thr Ala Ser
130                 135                 140

Ile Phe Ala Thr Tyr Pro Ala Pro Tyr Leu Ser Leu Asn Asn Gly Phe
145                 150                 155                 160

Leu Asp Gln Val Leu Gly Thr Gly Met Leu Ile Val Gly Leu Leu Ala
                165                 170                 175

Ile Leu Asp Arg Arg Asn Lys Gly Val Pro Ala Gly Leu Glu Pro Val
                180                 185                 190

Val Val Gly Met Leu Ile Leu Ala Leu Gly Leu Ser Met Gly Ala Asn
                195                 200                 205

Cys Gly Ile Pro Leu Asn Pro Ala Arg Asp Leu Gly Pro Arg Leu Phe
210                 215                 220

Thr Tyr Val Ala Gly Trp Gly Pro Glu Val Phe Ser Ala Gly Asn Gly
225                 230                 235                 240

Trp Trp Trp Val Pro Val Val Ala Pro Leu Val Gly Ala Thr Val Gly
                245                 250                 255

Thr Ala Thr Tyr Gln Leu Leu Val Ala Leu His His Pro Glu Gly Pro
                260                 265                 270

Glu Pro Ala Gln Asp Leu Val Ser Ala Gln His Lys Ala Ser Glu Leu
                275                 280                 285

Glu Thr Pro Ala Ser Ala Gln Met Leu Glu Cys Lys Leu
                290                 295                 300

<210> SEQ ID NO 53
<211> LENGTH: 251
<212> TYPE: PRT
<213> ORGANISM: Arabidopsis thaliana

<400> SEQUENCE: 53

Met Pro Ile Arg Asn Ile Ala Ile Gly Arg Pro Asp Glu Ala Thr Arg
 1               5                  10                  15

Pro Asp Ala Leu Lys Ala Ala Leu Ala Glu Phe Ile Ser Thr Leu Ile
                20                  25                  30

Phe Val Val Ala Gly Ser Gly Ser Gly Met Ala Phe Asn Lys Leu Thr
                35                  40                  45

Glu Asn Gly Ala Thr Thr Pro Ser Gly Leu Val Ala Ala Val Ala
 50                  55                  60

His Ala Phe Gly Leu Phe Val Ala Val Ser Val Gly Ala Asn Ile Ser
 65                  70                  75                  80

Gly Gly His Val Asn Pro Ala Val Thr Phe Gly Ala Phe Ile Gly Gly
                85                  90                  95

Asn Ile Thr Leu Leu Arg Gly Ile Leu Tyr Trp Ile Ala Gln Leu Leu
                100                 105                 110

Gly Ser Val Val Ala Cys Leu Ile Leu Lys Phe Ala Thr Gly Gly Leu
```

```
            115                 120                 125
Ala Val Pro Ala Phe Gly Leu Ser Ala Gly Val Gly Val Leu Asn Ala
        130                 135                 140

Phe Val Phe Glu Ile Val Met Thr Phe Gly Leu Val Tyr Thr Val Tyr
145                 150                 155                 160

Ala Thr Ala Ile Asp Pro Lys Asn Gly Ser Leu Gly Thr Ile Ala Pro
                165                 170                 175

Ile Ala Ile Gly Phe Ile Val Gly Ala Asn Ile Leu Ala Gly Gly Ala
                180                 185                 190

Phe Ser Gly Ala Ser Met Asn Pro Ala Val Ala Phe Gly Pro Ala Val
                195                 200                 205

Val Ser Trp Thr Trp Thr Asn His Trp Val Tyr Trp Ala Gly Pro Leu
        210                 215                 220

Val Gly Gly Gly Ile Ala Gly Leu Ile Tyr Glu Val Phe Phe Ile Asn
225                 230                 235                 240

Thr Thr His Glu Gln Leu Pro Thr Thr Asp Tyr
                245                 250

<210> SEQ ID NO 54
<211> LENGTH: 253
<212> TYPE: PRT
<213> ORGANISM: Arabidopsis thaliana

<400> SEQUENCE: 54

Met Pro Thr Arg Asn Ile Ala Ile Gly Gly Val Gln Glu Glu Val Tyr
1               5                   10                  15

His Pro Asn Ala Leu Arg Ala Ala Leu Ala Glu Phe Ile Ser Thr Leu
                20                  25                  30

Ile Phe Val Phe Ala Gly Ser Gly Ser Gly Ile Ala Phe Asn Lys Ile
            35                  40                  45

Thr Asp Asn Gly Ala Thr Thr Pro Ser Gly Leu Val Ala Ala Ala Leu
    50                  55                  60

Ala His Ala Phe Gly Leu Phe Val Ala Val Ser Val Gly Ala Asn Ile
65                  70                  75                  80

Ser Gly Gly His Val Asn Pro Ala Val Thr Phe Gly Val Leu Leu Gly
                85                  90                  95

Gly Asn Ile Thr Leu Leu Arg Gly Ile Leu Tyr Trp Ile Ala Gln Leu
            100                 105                 110

Leu Gly Ser Val Ala Ala Cys Phe Leu Leu Ser Phe Ala Thr Gly Gly
        115                 120                 125

Glu Pro Ile Pro Ala Phe Gly Leu Ser Ala Gly Val Gly Ser Leu Asn
    130                 135                 140

Ala Leu Val Phe Glu Ile Val Met Thr Phe Gly Leu Val Tyr Thr Val
145                 150                 155                 160

Tyr Ala Thr Ala Val Asp Pro Lys Asn Gly Ser Leu Gly Thr Ile Ala
                165                 170                 175

Pro Ile Ala Ile Gly Phe Ile Val Gly Ala Asn Ile Leu Ala Gly Gly
            180                 185                 190

Ala Phe Ser Gly Ala Ser Met Asn Pro Ala Val Ala Phe Gly Pro Ala
        195                 200                 205

Val Val Ser Trp Thr Trp Thr Asn His Trp Val Tyr Trp Ala Gly Pro
    210                 215                 220

Leu Ile Gly Gly Gly Leu Ala Gly Ile Ile Tyr Asp Phe Val Phe Ile
225                 230                 235                 240

Asp Glu Asn Ala His Glu Gln Leu Pro Thr Thr Asp Tyr
```

-continued

<210> SEQ ID NO 55
<211> LENGTH: 252
<212> TYPE: PRT
<213> ORGANISM: Arabidopsis thaliana

<400> SEQUENCE: 55

Met Pro Ile Asn Arg Ile Ala Ile Gly Thr Pro Gly Glu Ala Ser Arg
1               5                   10                  15

Pro Asp Ala Ile Arg Ala Ala Phe Ala Glu Phe Phe Ser Met Val Ile
                20                  25                  30

Phe Val Phe Ala Gly Gln Gly Ser Gly Met Ala Tyr Gly Lys Leu Thr
            35                  40                  45

Gly Asp Gly Pro Ala Thr Pro Ala Gly Leu Val Ala Ala Ser Leu Ser
        50                  55                  60

His Ala Phe Ala Leu Phe Val Ala Val Ser Val Gly Ala Asn Val Ser
65                  70                  75                  80

Gly Gly His Val Asn Pro Ala Val Thr Phe Gly Ala Phe Ile Gly Gly
                85                  90                  95

Asn Ile Thr Leu Leu Arg Ala Ile Leu Tyr Trp Ile Ala Gln Leu Leu
            100                 105                 110

Gly Ala Val Val Ala Cys Leu Leu Leu Lys Val Ser Thr Gly Gly Met
        115                 120                 125

Glu Thr Ala Ala Phe Ser Leu Ser Tyr Gly Val Thr Pro Trp Asn Ala
    130                 135                 140

Val Val Phe Glu Ile Val Met Thr Phe Gly Leu Val Tyr Thr Val Tyr
145                 150                 155                 160

Ala Thr Ala Val Asp Pro Lys Lys Gly Asp Ile Gly Ile Ile Ala Pro
                165                 170                 175

Leu Ala Ile Gly Leu Ile Val Gly Ala Asn Ile Leu Val Gly Gly Ala
            180                 185                 190

Phe Asp Gly Ala Ser Met Asn Pro Ala Val Ser Phe Gly Pro Ala Val
        195                 200                 205

Val Ser Trp Ile Trp Thr Asn His Trp Val Tyr Trp Val Gly Pro Phe
    210                 215                 220

Ile Gly Ala Ala Ile Ala Ala Ile Val Tyr Asp Thr Ile Phe Ile Gly
225                 230                 235                 240

Ser Asn Gly His Glu Pro Leu Pro Ser Asn Asp Phe
                245                 250

<210> SEQ ID NO 56
<211> LENGTH: 250
<212> TYPE: PRT
<213> ORGANISM: Zea mays

<400> SEQUENCE: 56

Met Pro Ile Asn Arg Ile Ala Leu Gly Ser His Gln Glu Val Tyr His
1               5                   10                  15

Pro Gly Ala Leu Lys Ala Ala Phe Ala Glu Phe Ile Ser Thr Leu Ile
                20                  25                  30

Phe Val Phe Ala Gly Gln Gly Ser Gly Met Ala Phe Ser Lys Leu Thr
            35                  40                  45

Gly Gly Gly Pro Thr Thr Pro Ala Gly Leu Ile Ala Ala Val Ala
        50                  55                  60

His Ala Phe Ala Leu Phe Val Ala Val Ser Val Gly Ala Asn Ile Ser
65                  70                  75                  80

```
Gly Gly His Val Asn Pro Ala Val Thr Phe Gly Ala Phe Val Gly Gly
                85                  90                  95

Asn Ile Thr Leu Phe Arg Gly Leu Leu Tyr Trp Val Ala Gln Leu Leu
            100                 105                 110

Gly Ser Thr Val Ala Cys Phe Leu Leu Arg Phe Ser Thr Gly Gly Gln
        115                 120                 125

Ala Thr Gly Thr Phe Gly Leu Thr Gly Val Ser Val Trp Glu Ala Leu
    130                 135                 140

Val Leu Glu Ile Val Met Thr Phe Gly Leu Val Tyr Thr Val Tyr Ala
145                 150                 155                 160

Thr Ala Val Asp Pro Lys Lys Gly Ser Leu Gly Thr Ile Ala Pro Ile
                165                 170                 175

Ala Ile Gly Phe Ile Val Gly Ala Asn Ile Leu Val Gly Gly Ala Phe
            180                 185                 190

Asp Gly Ala Ser Met Asn Pro Ala Val Ser Phe Gly Pro Ala Leu Val
        195                 200                 205

Ser Trp Glu Trp Gly Tyr Gln Trp Val Tyr Trp Val Gly Pro Leu Ile
    210                 215                 220

Gly Gly Gly Leu Ala Gly Val Ile Tyr Glu Leu Phe Ile Ser His
225                 230                 235                 240

Thr His Glu Gln Leu Pro Ser Thr Asp Tyr
                245                 250

<210> SEQ ID NO 57
<211> LENGTH: 254
<212> TYPE: PRT
<213> ORGANISM: Zea mays

<400> SEQUENCE: 57

Met Pro Val Ser Arg Ile Ala Val Gly Ala Pro Gly Glu Leu Ser His
1               5                   10                  15

Pro Asp Thr Ala Lys Ala Ala Val Ala Glu Phe Ile Ser Thr Leu Ile
                20                  25                  30

Phe Val Phe Ala Gly Ser Gly Ser Gly Met Ala Phe Ser Lys Leu Thr
            35                  40                  45

Asp Gly Gly Ala Ala Thr Pro Ala Gly Leu Ile Ala Ala Ser Leu Ala
        50                  55                  60

His Ala Leu Ala Leu Phe Val Ala Val Ser Val Gly Ala Asn Ile Ser
65                  70                  75                  80

Gly Gly His Val Asn Pro Ala Val Thr Phe Gly Ala Phe Val Gly Gly
                85                  90                  95

Asn Ile Ser Leu Leu Lys Ala Leu Val Tyr Trp Val Ala Gln Leu Leu
            100                 105                 110

Gly Ser Val Val Ala Cys Leu Leu Leu Lys Ile Ala Thr Gly Gly Ala
        115                 120                 125

Ala Leu Gly Ala Phe Ser Leu Ser Ala Gly Val Gly Ala Met Asn Ala
    130                 135                 140

Val Val Leu Glu Met Val Met Thr Phe Gly Leu Val Tyr Thr Val Tyr
145                 150                 155                 160

Ala Thr Ala Val Asp Pro Lys Lys Gly Asp Leu Gly Val Ile Ala Pro
                165                 170                 175

Ile Ala Ile Gly Phe Ile Val Gly Ala Asn Ile Leu Ala Gly Gly Ala
            180                 185                 190

Phe Asp Gly Ala Ser Met Asn Pro Ala Val Ser Phe Gly Pro Ala Val
        195                 200                 205
```

Val Thr Gly Val Trp Glu Asn His Trp Val Tyr Trp Val Gly Pro Leu
    210                 215                 220

Ala Gly Ala Ala Ile Ala Ala Leu Val Tyr Asp Ile Ile Phe Ile Gly
225                 230                 235                 240

Gln Arg Pro His Gln Gln Leu Pro Thr Thr Ala Ala Asp Tyr
                245                 250

<210> SEQ ID NO 58
<211> LENGTH: 250
<212> TYPE: PRT
<213> ORGANISM: Arabidopsis thaliana

<400> SEQUENCE: 58

Met Ala Gly Val Ala Phe Gly Ser Phe Asp Asp Ser Phe Ser Leu Ala
1               5                   10                  15

Ser Leu Arg Ala Tyr Leu Ala Glu Phe Ile Ser Thr Leu Leu Phe Val
                20                  25                  30

Phe Ala Gly Val Gly Ser Ala Ile Ala Tyr Ala Lys Leu Thr Ser Asp
            35                  40                  45

Ala Ala Leu Asp Thr Pro Gly Leu Val Ala Ile Ala Val Cys His Gly
        50                  55                  60

Phe Ala Leu Phe Val Ala Val Ala Ile Gly Ala Asn Ile Ser Gly Gly
65                  70                  75                  80

His Val Asn Pro Ala Val Thr Phe Gly Leu Ala Val Gly Gly Gln Ile
                85                  90                  95

Thr Val Ile Thr Gly Val Phe Tyr Trp Ile Ala Gln Leu Leu Gly Ser
            100                 105                 110

Thr Ala Ala Cys Phe Leu Leu Lys Tyr Val Thr Gly Gly Leu Ala Val
        115                 120                 125

Pro Thr His Ser Val Ala Ala Gly Leu Gly Ser Ile Glu Gly Val Val
    130                 135                 140

Met Glu Ile Ile Ile Thr Phe Ala Leu Val Tyr Thr Val Tyr Ala Thr
145                 150                 155                 160

Ala Ala Asp Pro Lys Lys Gly Ser Leu Gly Thr Ile Ala Pro Leu Ala
                165                 170                 175

Ile Gly Leu Ile Val Gly Ala Asn Ile Leu Ala Ala Gly Pro Phe Ser
            180                 185                 190

Gly Gly Ser Met Asn Pro Ala Arg Ser Phe Gly Pro Ala Val Ala Ala
        195                 200                 205

Gly Asp Phe Ser Gly His Trp Val Tyr Trp Val Gly Pro Leu Ile Gly
    210                 215                 220

Gly Gly Leu Ala Gly Leu Ile Tyr Gly Asn Val Phe Met Gly Ser Ser
225                 230                 235                 240

Glu His Val Pro Leu Ala Ser Ala Asp Phe
                245                 250

<210> SEQ ID NO 59
<211> LENGTH: 250
<212> TYPE: PRT
<213> ORGANISM: Arabidopsis thaliana

<400> SEQUENCE: 59

Met Val Lys Ile Glu Ile Gly Ser Val Gly Asp Ser Phe Ser Val Ala
1               5                   10                  15

Ser Leu Lys Ala Tyr Leu Ser Glu Phe Ile Ala Thr Leu Leu Phe Val
                20                  25                  30

```
Phe Ala Gly Val Gly Ser Ala Leu Ala Phe Ala Lys Leu Thr Ser Asp
            35                  40                  45

Ala Ala Leu Asp Pro Ala Gly Leu Val Ala Val Ala Val Ala His Ala
        50                  55                  60

Phe Ala Leu Phe Val Gly Val Ser Ile Ala Ala Asn Ile Ser Gly Gly
 65                  70                  75                  80

His Leu Asn Pro Ala Val Thr Leu Gly Leu Ala Val Gly Gly Asn Ile
                85                  90                  95

Thr Val Ile Thr Gly Phe Phe Tyr Trp Ile Ala Gln Cys Leu Gly Ser
            100                 105                 110

Ile Val Ala Cys Leu Leu Leu Val Phe Val Thr Asn Gly Glu Ser Val
        115                 120                 125

Pro Thr His Gly Val Ala Ala Gly Leu Gly Ala Ile Glu Gly Val Val
    130                 135                 140

Met Glu Ile Val Val Thr Phe Ala Leu Val Tyr Thr Val Tyr Ala Thr
145                 150                 155                 160

Ala Ala Asp Pro Lys Lys Gly Ser Leu Gly Thr Ile Ala Pro Ile Ala
                165                 170                 175

Ile Gly Phe Ile Val Gly Ala Asn Ile Leu Ala Ala Gly Pro Phe Ser
            180                 185                 190

Gly Gly Ser Met Asn Pro Ala Arg Ser Phe Gly Pro Ala Val Val Ser
        195                 200                 205

Gly Asp Phe Ser Gln Ile Trp Ile Tyr Trp Val Gly Pro Leu Val Gly
    210                 215                 220

Gly Ala Leu Ala Gly Leu Ile Tyr Gly Asp Val Phe Ile Gly Ser Tyr
225                 230                 235                 240

Ala Pro Ala Pro Thr Thr Glu Ser Tyr Pro
                245                 250

<210> SEQ ID NO 60
<211> LENGTH: 250
<212> TYPE: PRT
<213> ORGANISM: Arabidopsis thaliana

<400> SEQUENCE: 60

Met Val Lys Ile Glu Val Gly Ser Val Gly Asp Ser Phe Ser Val Ser
1               5                   10                  15

Ser Leu Lys Ala Tyr Leu Ser Glu Phe Ile Ala Thr Leu Leu Phe Val
            20                  25                  30

Phe Ala Gly Val Gly Ser Ala Val Ala Phe Ala Lys Leu Thr Ser Asp
        35                  40                  45

Gly Ala Leu Asp Pro Ala Gly Leu Val Ala Ile Ala Ile Ala His Ala
    50                  55                  60

Phe Ala Leu Phe Val Gly Val Ser Ile Ala Ala Asn Ile Ser Gly Gly
 65                 70                  75                  80

His Leu Asn Pro Ala Val Thr Leu Gly Leu Ala Ile Gly Gly Asn Ile
                85                  90                  95

Thr Leu Ile Thr Gly Phe Phe Tyr Trp Ile Ala Gln Cys Leu Gly Ser
            100                 105                 110

Ile Val Ala Cys Leu Leu Leu Val Phe Val Thr Asn Gly Lys Ser Val
        115                 120                 125

Pro Thr His Gly Val Ser Ala Gly Leu Gly Ala Val Glu Gly Val Val
    130                 135                 140

Met Glu Ile Val Val Thr Phe Ala Leu Val Tyr Thr Val Tyr Ala Thr
145                 150                 155                 160
```

```
Ala Ala Asp Pro Lys Lys Gly Ser Leu Gly Thr Ile Ala Pro Ile Ala
            165                 170                 175

Ile Gly Phe Ile Val Gly Ala Asn Ile Leu Ala Ala Gly Pro Phe Ser
            180                 185                 190

Gly Gly Ser Met Asn Pro Ala Arg Ser Phe Gly Pro Ala Val Val Ser
            195                 200                 205

Gly Asp Leu Ser Gln Ile Trp Ile Tyr Trp Val Gly Pro Leu Val Gly
        210                 215                 220

Gly Ala Leu Ala Gly Leu Ile Tyr Gly Asp Val Phe Ile Gly Ser Tyr
225                 230                 235                 240

Glu Ala Val Glu Thr Arg Glu Ile Arg Val
            245                 250

<210> SEQ ID NO 61
<211> LENGTH: 249
<212> TYPE: PRT
<213> ORGANISM: Zea mays

<400> SEQUENCE: 61

Met Val Lys Leu Ala Phe Gly Ser Val Gly Asp Ser Phe Ser Ala Thr
1               5                   10                  15

Ser Ile Lys Ala Tyr Val Ala Glu Phe Ile Ala Thr Leu Leu Phe Val
            20                  25                  30

Phe Ala Gly Val Gly Ser Ala Ile Ala Tyr Gly Gln Leu Thr Asn Gly
        35                  40                  45

Gly Ala Leu Asp Pro Ala Gly Leu Val Ala Ile Ala Ile Ala His Ala
    50                  55                  60

Leu Ala Leu Phe Val Gly Val Ser Val Ala Ala Asn Ile Ser Gly Gly
65                  70                  75                  80

His Leu Asn Pro Ala Val Thr Phe Gly Leu Ala Val Gly Gly His Ile
            85                  90                  95

Thr Ile Leu Thr Gly Val Phe Tyr Trp Val Ala Gln Leu Leu Gly Ala
            100                 105                 110

Thr Val Ala Cys Leu Leu Leu Gly Phe Val Thr His Gly Lys Ala Ile
            115                 120                 125

Pro Thr His Ala Val Ala Gly Ile Ser Glu Leu Glu Gly Val Val Phe
    130                 135                 140

Glu Val Val Ile Thr Phe Ala Leu Val Tyr Thr Val Tyr Ala Thr Ala
145                 150                 155                 160

Ala Asp Pro Lys Lys Gly Ser Leu Gly Thr Ile Ala Pro Ile Ala Ile
            165                 170                 175

Gly Phe Ile Val Gly Ala Asn Ile Leu Ala Ala Gly Pro Phe Ser Gly
            180                 185                 190

Gly Ser Met Asn Pro Ala Arg Ser Phe Gly Pro Ala Val Ala Ala Gly
            195                 200                 205

Asp Phe Ala Gly Asn Trp Val Tyr Trp Val Gly Pro Leu Val Gly Gly
        210                 215                 220

Gly Leu Ala Gly Leu Val Tyr Gly Asp Val Phe Ile Gly Gly Ser Tyr
225                 230                 235                 240

Gln Gln Val Ala Asp Gln Asp Tyr Ala
            245

<210> SEQ ID NO 62
<211> LENGTH: 250
<212> TYPE: PRT
<213> ORGANISM: Zea mays
```

<400> SEQUENCE: 62

```
Met Val Lys Leu Ala Phe Gly Ser Val Gly Asp Ser Phe Ser Val Thr
1               5                   10                  15

Ser Ile Lys Ala Tyr Val Ala Glu Phe Ile Ala Thr Leu Leu Phe Val
            20                  25                  30

Phe Ala Gly Val Gly Ser Ala Ile Ala Phe Gly Gln Leu Thr Asn Gly
        35                  40                  45

Gly Ala Leu Asp Pro Ala Gly Leu Val Ala Ile Ala Val Ala His Ala
    50                  55                  60

Leu Ala Leu Phe Val Gly Val Ser Val Ala Ala Asn Thr Ser Gly Gly
65                  70                  75                  80

His Leu Asn Pro Ala Val Thr Phe Gly Leu Ala Val Gly Gly His Ile
                85                  90                  95

Thr Val Leu Thr Gly Leu Phe Tyr Trp Val Ala Gln Leu Leu Gly Ala
            100                 105                 110

Ser Val Ala Cys Leu Leu Leu Arg Phe Val Thr His Gly Lys Ala Ile
        115                 120                 125

Pro Thr His Gly Val Ser Gly Gly Thr Thr Glu Leu Glu Gly Val Val
    130                 135                 140

Phe Glu Ile Val Ile Thr Phe Ala Leu Val Tyr Thr Val Tyr Ala Thr
145                 150                 155                 160

Ala Ala Asp Pro Lys Lys Gly Ser Leu Gly Thr Ile Ala Pro Ile Ala
                165                 170                 175

Ile Gly Phe Ile Val Gly Ala Asn Ile Leu Ala Ala Gly Pro Phe Ser
            180                 185                 190

Gly Gly Ser Met Asn Pro Ala Arg Ser Phe Gly Pro Ala Val Ala Ala
        195                 200                 205

Ala Asp Phe Ala Gly Asn Trp Val Tyr Trp Val Gly Pro Leu Ile Gly
    210                 215                 220

Gly Gly Leu Ala Gly Leu Val Tyr Gly Asp Val Phe Ile Gly Gly Ser
225                 230                 235                 240

Tyr Gln Gln Val Ala Asp Gln Asp Tyr Ala
                245                 250
```

<210> SEQ ID NO 63
<211> LENGTH: 248
<212> TYPE: PRT
<213> ORGANISM: Zea mays

<400> SEQUENCE: 63

```
Met Val Lys Leu Ala Phe Gly Ser Phe Arg Asp Ser Leu Ser Ala Ala
1               5                   10                  15

Ser Leu Lys Ala Tyr Val Ala Glu Phe Ile Ala Thr Leu Leu Phe Val
            20                  25                  30

Phe Ala Gly Val Gly Ser Ala Ile Ala Tyr Ser Gln Leu Thr Lys Gly
        35                  40                  45

Gly Ala Leu Asp Pro Ala Gly Leu Val Ala Ile Ala Ile Ala His Ala
    50                  55                  60

Phe Ala Leu Phe Val Gly Val Ser Met Ala Ala Asn Ile Ser Gly Gly
65                  70                  75                  80

His Leu Asn Pro Ala Val Thr Phe Gly Leu Ala Val Gly Gly His Ile
                85                  90                  95

Thr Ile Leu Thr Gly Ile Leu Tyr Trp Val Ala Gln Leu Leu Gly Ala
            100                 105                 110

Ser Val Ala Cys Phe Leu Leu Gln Tyr Val Thr His Gly Gln Ala Ile
```

```
            115                 120                 125
Pro Thr His Gly Val Ser Gly Ile Ser Glu Ile Glu Gly Val Val Met
            130                 135                 140
Glu Ile Val Ile Thr Phe Ala Leu Val Tyr Thr Val Tyr Ala Thr Ala
145                 150                 155                 160
Ala Asp Pro Lys Lys Gly Ser Leu Gly Thr Ile Ala Pro Met Ala Ile
                165                 170                 175
Gly Phe Ile Val Gly Ala Asn Ile Leu Ala Ala Gly Pro Phe Ser Gly
                180                 185                 190
Gly Ser Met Asn Pro Ala Arg Ser Phe Gly Pro Ala Val Ala Ala Gly
                195                 200                 205
Asn Phe Ala Gly Asn Trp Val Tyr Trp Val Gly Pro Leu Val Gly Gly
                210                 215                 220
Gly Leu Ala Gly Leu Val Tyr Gly Asp Val Phe Ile Ala Ser Tyr Gln
225                 230                 235                 240
Pro Val Gly Gln Gln Glu Tyr Pro
                245

<210> SEQ ID NO 64
<211> LENGTH: 268
<212> TYPE: PRT
<213> ORGANISM: Arabidopsis thaliana

<400> SEQUENCE: 64

Met Ala Thr Ser Ala Arg Arg Ala Tyr Gly Phe Gly Arg Ala Asp Glu
1               5                   10                  15
Ala Thr His Pro Asp Ser Ile Arg Ala Thr Leu Ala Glu Phe Leu Ser
                20                  25                  30
Thr Phe Val Phe Val Phe Ala Ala Glu Gly Ser Ile Leu Ser Leu Asp
                35                  40                  45
Lys Leu Tyr Trp Glu His Ala Ala His Ala Gly Thr Asn Thr Pro Gly
50                  55                  60
Gly Leu Ile Leu Val Ala Leu Ala His Ala Phe Ala Leu Phe Ala Ala
65                  70                  75                  80
Val Ser Ala Ala Ile Asn Val Ser Gly Gly His Val Asn Pro Ala Val
                85                  90                  95
Thr Phe Gly Ala Leu Val Gly Gly Arg Val Thr Ala Ile Arg Ala Ile
                100                 105                 110
Tyr Tyr Trp Ile Ala Gln Leu Leu Gly Ala Ile Leu Ala Cys Leu Leu
                115                 120                 125
Leu Arg Leu Thr Thr Asn Gly Met Arg Pro Val Gly Phe Arg Leu Ala
                130                 135                 140
Ser Gly Val Gly Ala Val Asn Gly Leu Val Leu Glu Ile Ile Leu Thr
145                 150                 155                 160
Phe Gly Leu Val Tyr Val Tyr Ser Thr Leu Ile Asp Pro Lys Arg
                165                 170                 175
Gly Ser Leu Gly Ile Ile Ala Pro Leu Ala Ile Gly Leu Ile Val Gly
                180                 185                 190
Ala Asn Ile Leu Val Gly Gly Pro Phe Ser Gly Ala Ser Met Asn Pro
                195                 200                 205
Ala Arg Ala Phe Gly Pro Ala Leu Val Gly Trp Arg Trp His Asp His
                210                 215                 220
Trp Ile Tyr Trp Val Gly Pro Phe Ile Gly Ser Ala Leu Ala Ala Leu
225                 230                 235                 240
Ile Tyr Glu Tyr Met Val Ile Pro Thr Glu Pro Pro Thr His His Ala
```

```
                245                 250                 255
His Gly Val His Gln Pro Leu Ala Pro Glu Asp Tyr
            260                 265

<210> SEQ ID NO 65
<211> LENGTH: 267
<212> TYPE: PRT
<213> ORGANISM: Arabidopsis thaliana

<400> SEQUENCE: 65

Met Ala Thr Ser Ala Arg Arg Ala Tyr Gly Phe Gly Arg Ala Asp Glu
1               5                   10                  15

Ala Thr His Pro Asp Ser Ile Arg Ala Thr Leu Ala Glu Phe Leu Ser
            20                  25                  30

Thr Phe Val Phe Val Phe Ala Gly Glu Gly Ser Ile Leu Ala Leu Asp
        35                  40                  45

Lys Leu Tyr Trp Asp Thr Ala Ala His Thr Gly Thr Asn Thr Pro Gly
    50                  55                  60

Gly Leu Val Leu Val Ala Leu Ala His Ala Leu Ala Leu Phe Ala Ala
65                  70                  75                  80

Val Ser Ala Ala Ile Asn Val Ser Gly Gly His Val Asn Pro Ala Val
                85                  90                  95

Thr Phe Ala Ala Leu Ile Gly Gly Arg Ile Ser Val Ile Arg Ala Ile
            100                 105                 110

Tyr Tyr Trp Val Ala Gln Leu Ile Gly Ala Ile Leu Ala Cys Leu Leu
        115                 120                 125

Leu Arg Leu Ala Thr Asn Gly Leu Arg Pro Val Gly Phe His Val Ala
    130                 135                 140

Ser Gly Val Ser Glu Leu His Gly Leu Leu Met Glu Ile Ile Leu Thr
145                 150                 155                 160

Phe Ala Leu Val Tyr Val Val Tyr Ser Thr Ala Ile Asp Pro Lys Arg
                165                 170                 175

Gly Ser Ile Gly Ile Ile Ala Pro Leu Ala Ile Gly Leu Ile Val Gly
            180                 185                 190

Ala Asn Ile Leu Val Gly Gly Pro Phe Asp Gly Ala Ser Met Asn Pro
        195                 200                 205

Ala Arg Ala Phe Gly Pro Ala Leu Val Gly Trp Arg Trp Ser Asn His
    210                 215                 220

Trp Ile Tyr Trp Val Gly Pro Phe Ile Gly Gly Ala Leu Ala Ala Leu
225                 230                 235                 240

Ile Tyr Glu Tyr Met Ile Ile Pro Ser Val Asn Glu Pro Pro His His
                245                 250                 255

Ser Thr His Gln Pro Leu Ala Pro Glu Asp Tyr
            260                 265

<210> SEQ ID NO 66
<211> LENGTH: 262
<212> TYPE: PRT
<213> ORGANISM: Zea mays

<400> SEQUENCE: 66

Met Ser Thr Gly Val Arg Pro Gly Arg Arg Phe Thr Val Gly Arg Ser
1               5                   10                  15

Glu Asp Ala Thr His Pro Asp Thr Ile Arg Ala Ala Ile Ser Glu Phe
            20                  25                  30

Ile Ala Thr Ala Ile Phe Val Phe Ala Ala Glu Gly Ser Val Leu Ser
        35                  40                  45
```

```
Leu Gly Lys Met Tyr His Asp Met Ser Thr Ala Gly Leu Val Ala
        50                  55                  60

Val Ala Leu Ala His Ala Leu Ala Leu Ala Val Ala Val Ala Val Ala
 65                  70                  75                  80

Val Asn Ile Ser Gly Gly His Val Asn Pro Ala Val Thr Phe Gly Ala
                 85                  90                  95

Leu Val Gly Gly Arg Val Ser Leu Val Arg Ala Val Leu Tyr Trp Val
            100                 105                 110

Ala Gln Leu Leu Gly Ala Val Ala Ala Thr Leu Leu Arg Leu Ala
        115                 120                 125

Thr Gly Gly Met Arg Pro Pro Gly Phe Ala Leu Ala Ser Gly Val Gly
130                 135                 140

Asp Trp His Ala Val Leu Leu Glu Ala Val Met Thr Phe Gly Leu Met
145                 150                 155                 160

Tyr Ala Tyr Tyr Ala Thr Val Ile Asp Pro Lys Arg Gly His Val Gly
                165                 170                 175

Thr Ile Ala Pro Leu Ala Val Gly Phe Leu Gly Ala Asn Val Leu
                180                 185                 190

Ala Gly Gly Pro Phe Asp Gly Ala Gly Met Asn Pro Ala Arg Val Phe
        195                 200                 205

Gly Pro Ala Leu Val Gly Trp Arg Trp Arg His His Trp Val Tyr Trp
210                 215                 220

Leu Gly Pro Phe Leu Gly Ala Gly Leu Ala Gly Leu Val Tyr Glu Tyr
225                 230                 235                 240

Leu Val Ile Pro Ser Ala Asp Ala Ala Val Pro His Ala His Gln Pro
                245                 250                 255

Leu Ala Pro Glu Asp Tyr
                260

<210> SEQ ID NO 67
<211> LENGTH: 266
<212> TYPE: PRT
<213> ORGANISM: Zea mays

<400> SEQUENCE: 67

Met Ser Thr Ala Thr Gly Val Arg Ala Gly Arg Arg Phe Thr Val Gly
1               5                   10                  15

Arg Ser Glu Asp Ala Thr His Pro Asp Thr Ile Arg Ala Ala Ile Ser
                20                  25                  30

Glu Phe Ile Ala Thr Ala Ile Phe Val Phe Ala Ala Glu Gly Ser Val
            35                  40                  45

Leu Ser Leu Gly Lys Met Tyr His Asp His Ser Thr Ile Ser Thr Ala
        50                  55                  60

Gly Gly Leu Val Ala Val Ala Leu Ala His Ala Leu Gly Leu Ala Val
 65                  70                  75                  80

Ala Val Ala Val Ala Val Asn Val Ser Gly Gly His Val Asn Pro Ala
                 85                  90                  95

Val Thr Phe Gly Ala Leu Val Gly Gly Arg Val Ser Leu Val Arg Ala
            100                 105                 110

Val Leu Tyr Trp Ala Ala Gln Leu Leu Gly Ala Val Ala Ala Thr Leu
        115                 120                 125

Leu Leu Arg Leu Ala Thr Gly Gly Ala Arg Pro Pro Gly Phe Ala Leu
130                 135                 140

Ala Ser Gly Val Gly Asp Gly His Ala Val Leu Leu Glu Ala Val Met
145                 150                 155                 160
```

```
Thr Phe Gly Phe Val Tyr Ala Tyr Ala Thr Val Val Asp Pro Lys
                165                 170                 175

Arg Gly His Leu Gly Thr Ile Ala Pro Leu Ala Val Gly Phe Leu Leu
            180                 185                 190

Gly Ala Asn Val Leu Ala Gly Gly Pro Phe Asp Gly Ala Gly Met Asn
            195                 200                 205

Pro Ala Arg Val Phe Gly Pro Ala Leu Val Gly Trp Arg Trp Arg His
210                 215                 220

His Trp Val Tyr Trp Leu Gly Pro Phe Leu Gly Ala Gly Leu Ala Gly
225                 230                 235                 240

Leu Val Tyr Glu Tyr Leu Leu Ile Pro Pro Ala Asp Ala Val Pro His
                245                 250                 255

Thr His Gln Pro Leu Ala Pro Glu Asp Tyr
            260                 265

<210> SEQ ID NO 68
<211> LENGTH: 249
<212> TYPE: PRT
<213> ORGANISM: Arabidopsis thaliana

<400> SEQUENCE: 68

Met Lys Lys Ile Glu Leu Gly His His Ser Glu Ala Ala Lys Pro Asp
1               5                   10                  15

Cys Ile Lys Ala Leu Ile Val Glu Phe Ile Thr Thr Phe Leu Phe Val
            20                  25                  30

Phe Ala Gly Val Gly Ser Ala Met Ala Thr Asp Ser Leu Val Gly Asn
        35                  40                  45

Thr Leu Val Gly Leu Phe Ala Val Ala Val Ala His Ala Phe Val Val
    50                  55                  60

Ala Val Met Ile Ser Ala Gly His Ile Ser Gly Gly His Leu Asn Pro
65                  70                  75                  80

Ala Val Thr Leu Gly Leu Leu Leu Gly Gly His Ile Ser Val Phe Arg
                85                  90                  95

Ala Phe Leu Tyr Trp Ile Asp Gln Leu Leu Ala Ser Ser Ala Ala Cys
            100                 105                 110

Phe Leu Leu Ser Tyr Leu Thr Gly Gly Met Gly Thr Pro Val His Thr
        115                 120                 125

Leu Ala Ser Gly Val Ser Tyr Thr Gln Gly Ile Ile Trp Glu Ile Ile
    130                 135                 140

Leu Thr Phe Ser Leu Leu Phe Thr Val Tyr Ala Thr Ile Val Asp Pro
145                 150                 155                 160

Lys Lys Gly Ser Leu Asp Gly Phe Gly Pro Leu Leu Thr Gly Phe Val
                165                 170                 175

Val Gly Ala Asn Ile Leu Ala Gly Gly Ala Phe Ser Gly Ala Ser Met
            180                 185                 190

Asn Pro Ala Arg Ser Phe Gly Pro Ala Leu Val Ser Gly Asn Trp Thr
        195                 200                 205

Asp His Trp Val Tyr Trp Val Gly Pro Leu Ile Gly Gly Gly Leu Ala
    210                 215                 220

Gly Phe Ile Tyr Glu Asn Val Leu Ile Asp Arg Pro His Val Pro Val
225                 230                 235                 240

Ala Asp Asp Glu Gln Pro Leu Leu Asn
                245

<210> SEQ ID NO 69
```

```
<211> LENGTH: 255
<212> TYPE: PRT
<213> ORGANISM: Zea mays

<400> SEQUENCE: 69

Met Ala Lys Leu Met Asn Lys Leu Val Asp Ser Phe Glu His Asp Glu
1               5                   10                  15

Ile Pro Asp Val Gly Cys Val Arg Ala Val Leu Ala Glu Leu Val Leu
                20                  25                  30

Thr Phe Leu Phe Val Phe Thr Gly Val Ser Ala Ala Met Ala Ala Gly
            35                  40                  45

Ser Asp Gly Lys Pro Gly Asp Ala Met Pro Met Ala Thr Leu Ala Ala
    50                  55                  60

Val Ala Ile Ala His Ala Leu Ala Ala Gly Val Leu Val Thr Ala Gly
65                  70                  75                  80

Phe His Val Ser Gly Gly His Leu Asn Pro Ala Val Thr Val Gly Leu
                85                  90                  95

Met Val Arg Gly His Ile Thr Lys Leu Arg Ala Val Leu Tyr Val Ala
                100                 105                 110

Ala Gln Leu Leu Ala Ser Ser Ala Ala Cys Val Leu Leu Arg Phe Leu
            115                 120                 125

Ser Gly Gly Met Val Thr Pro Val His Ala Leu Gly Arg Gly Ile Ser
130                 135                 140

Pro Met Gln Gly Leu Val Met Glu Val Ile Leu Thr Phe Ser Leu Leu
145                 150                 155                 160

Phe Val Thr Tyr Ala Met Ile Leu Asp Pro Arg Ser Gln Val Arg Ala
                165                 170                 175

Ile Gly Pro Leu Leu Thr Gly Leu Ile Val Gly Ala Asn Ser Leu Ala
            180                 185                 190

Gly Gly Asn Phe Thr Gly Ala Ser Met Asn Pro Ala Arg Ser Phe Gly
        195                 200                 205

Pro Ala Leu Ala Thr Gly Asp Trp Thr Asn His Trp Val Tyr Trp Ile
210                 215                 220

Gly Pro Leu Leu Gly Pro Leu Ala Gly Phe Val Tyr Glu Ser Leu
225                 230                 235                 240

Phe Leu Val Gln Lys Met His Glu Pro Leu Leu Asn Gly Glu Val
                245                 250                 255

<210> SEQ ID NO 70
<211> LENGTH: 257
<212> TYPE: PRT
<213> ORGANISM: Zea mays

<400> SEQUENCE: 70

Met Ala Lys Leu Val Asn Lys Leu Val Asp Ser Phe Asp His Asp Glu
1               5                   10                  15

Ala Pro Ala Pro Asp Val Gly Cys Val Arg Ala Val Leu Ala Glu Leu
                20                  25                  30

Val Leu Thr Phe Leu Phe Val Phe Thr Gly Val Ser Ala Ser Met Ala
            35                  40                  45

Ala Gly Ala Gly Gly Lys Pro Gly Glu Ala Met Pro Met Ala Thr Leu
    50                  55                  60

Ala Ala Val Ala Ile Ala His Ala Leu Ala Ala Gly Val Leu Val Thr
65                  70                  75                  80

Ala Gly Phe His Val Ser Gly Gly His Leu Asn Pro Ala Val Thr Val
                85                  90                  95
```

```
Gly Ile Leu Val Arg Gly His Ile Thr Lys Leu Arg Ala Leu Leu Tyr
            100                 105                 110

Val Ala Ala Gln Leu Leu Ala Ser Ser Leu Ala Cys Ile Leu Leu Arg
        115                 120                 125

Tyr Leu Ser Gly Gly Met Val Thr Pro Val His Ala Leu Gly Ala Gly
    130                 135                 140

Ile Arg Pro Met Gln Gly Leu Val Met Glu Val Ile Leu Thr Phe Ser
145                 150                 155                 160

Leu Leu Phe Val Thr Tyr Ala Met Ile Leu Asp Pro Arg Ser Gln Val
                165                 170                 175

Arg Thr Ile Gly Pro Leu Leu Thr Gly Leu Ile Val Gly Ala Asn Ser
                180                 185                 190

Leu Ala Gly Gly Asn Phe Thr Gly Ala Ser Met Asn Pro Ala Arg Ser
            195                 200                 205

Phe Gly Pro Ala Met Ala Thr Gly Val Trp Thr Asn His Trp Val Tyr
    210                 215                 220

Trp Ile Gly Pro Leu Leu Gly Gly Ser Leu Ala Gly Phe Val Tyr Glu
225                 230                 235                 240

Ser Leu Phe Met Val Asn Lys Thr His Glu Pro Leu Leu Asn Gly Asp
                245                 250                 255

Ile

<210> SEQ ID NO 71
<211> LENGTH: 249
<212> TYPE: PRT
<213> ORGANISM: Zea mays

<400> SEQUENCE: 71

Met Gly Lys Leu Thr Leu Gly His Arg Gly Glu Ala Ser Glu Pro Asp
1               5                   10                  15

Phe Phe Arg Gly Val Leu Gly Glu Leu Val Leu Thr Phe Leu Phe Val
            20                  25                  30

Phe Ile Gly Val Gly Ala Ala Met Thr Asp Gly Ala Thr Thr Lys Gly
        35                  40                  45

Ser Thr Ala Gly Gly Asp Leu Thr Ala Val Ala Leu Gly Gln Ala Leu
    50                  55                  60

Val Val Ala Val Ile Ala Thr Ala Gly Phe His Ile Ser Gly Gly His
65                  70                  75                  80

Val Asn Pro Ala Val Thr Leu Ser Leu Ala Val Gly Gly His Val Thr
                85                  90                  95

Leu Phe Arg Ser Ser Leu Tyr Ile Ala Ala Gln Met Leu Ala Ser Ser
            100                 105                 110

Ala Ala Cys Phe Leu Leu Arg Trp Leu Thr Gly Gly Leu Ala Thr Pro
        115                 120                 125

Val His Ala Leu Ala Glu Gly Val Gly Pro Leu Gln Gly Val Val Ala
    130                 135                 140

Glu Ala Val Phe Thr Phe Ser Leu Leu Phe Val Ile Tyr Ala Thr Ile
145                 150                 155                 160

Leu Asp Pro Arg Lys Leu Leu Pro Gly Ala Gly Pro Leu Leu Thr Gly
                165                 170                 175

Leu Leu Val Gly Ala Asn Ser Val Ala Gly Ala Ala Leu Ser Gly Ala
                180                 185                 190

Ser Met Asn Pro Ala Arg Ser Phe Gly Pro Ala Val Ala Ser Gly Val
            195                 200                 205

Trp Thr His His Trp Val Tyr Trp Val Gly Pro Leu Ala Gly Gly Pro
```

-continued

```
                210                 215                 220
Leu Ala Val Leu Val Tyr Glu Cys Cys Phe Met Ala Ala Pro Thr
225                 230                 235                 240

His Asp Leu Leu Pro Gln Gln Asp Pro
                245

<210> SEQ ID NO 72
<211> LENGTH: 252
<212> TYPE: PRT
<213> ORGANISM: Zea mays

<400> SEQUENCE: 72

Met Ala Lys Phe Ala Leu Gly His His Arg Glu Ala Ser Asp Ala Gly
1               5                   10                  15

Cys Val Arg Ala Val Leu Ala Glu Leu Ile Leu Thr Phe Leu Phe Val
                20                  25                  30

Phe Ala Gly Val Gly Ser Ala Met Ala Thr Gly Lys Leu Ala Gly Gly
            35                  40                  45

Gly Gly Asp Thr Val Val Gly Leu Thr Ala Val Ala Leu Ala His Thr
        50                  55                  60

Leu Val Val Ala Val Met Val Ser Ala Gly Leu His Val Ser Gly Gly
65                  70                  75                  80

His Ile Asn Pro Ala Val Thr Leu Gly Leu Ala Ala Thr Gly Arg Ile
                85                  90                  95

Thr Leu Phe Arg Ser Ala Leu Tyr Val Ala Ala Gln Leu Leu Gly Ser
                100                 105                 110

Thr Leu Ala Cys Leu Leu Leu Ala Phe Leu Ala Val Ala Asp Ser Gly
            115                 120                 125

Val Pro Val His Ala Leu Gly Ala Gly Val Gly Ala Leu Arg Gly Val
        130                 135                 140

Leu Met Glu Ala Val Leu Thr Phe Ser Leu Leu Phe Ala Val Tyr Ala
145                 150                 155                 160

Thr Val Val Asp Pro Arg Arg Ala Val Gly Gly Met Gly Pro Leu Leu
                165                 170                 175

Val Gly Leu Val Val Gly Ala Asn Val Leu Ala Gly Gly Pro Phe Ser
            180                 185                 190

Gly Ala Ser Met Asn Pro Ala Arg Ser Phe Gly Pro Ala Leu Val Ala
        195                 200                 205

Gly Val Trp Ala Asp His Trp Val Tyr Trp Val Gly Pro Leu Ile Gly
    210                 215                 220

Gly Pro Leu Ala Gly Leu Val Tyr Asp Gly Leu Phe Met Ala Gln Gly
225                 230                 235                 240

Gly His Glu Pro Leu Pro Arg Asp Asp Thr Asp Phe
                245                 250

<210> SEQ ID NO 73
<211> LENGTH: 256
<212> TYPE: PRT
<213> ORGANISM: Arabidopsis thaliana

<400> SEQUENCE: 73

Met Arg Arg Met Ile Pro Thr Ser Phe Ser Ser Lys Phe Gln Gly Val
1               5                   10                  15

Leu Ser Met Asn Ala Leu Arg Cys Tyr Val Ser Glu Phe Ile Ser Thr
                20                  25                  30

Phe Phe Phe Val Leu Ala Ala Val Gly Ser Val Met Ser Ser Arg Lys
            35                  40                  45
```

-continued

```
Leu Met Ala Gly Asp Val Ser Gly Pro Phe Gly Val Leu Ile Pro Ala
         50                  55                  60

Ile Ala Asn Ala Leu Ala Leu Ser Ser Ser Val Tyr Ile Ser Trp Asn
 65                  70                  75                  80

Val Ser Gly Gly His Val Asn Pro Ala Val Thr Phe Ala Met Ala Val
                 85                  90                  95

Ala Gly Arg Ile Ser Val Pro Thr Ala Met Phe Tyr Trp Thr Ser Gln
            100                 105                 110

Met Ile Ala Ser Val Met Ala Cys Leu Val Leu Lys Val Thr Val Met
            115                 120                 125

Glu Gln His Val Pro Ile Tyr Lys Ile Ala Gly Glu Met Thr Gly Phe
            130                 135                 140

Gly Ala Ser Val Leu Glu Gly Val Leu Ala Phe Val Leu Val Tyr Thr
145                 150                 155                 160

Val Phe Thr Ala Ser Asp Pro Arg Arg Gly Leu Pro Leu Ala Val Gly
                165                 170                 175

Pro Ile Phe Ile Gly Phe Val Ala Gly Ala Asn Val Leu Ala Ala Gly
                180                 185                 190

Pro Phe Ser Gly Gly Ser Met Asn Pro Ala Cys Ala Phe Gly Ser Ala
                195                 200                 205

Met Val Tyr Gly Ser Phe Lys Asn Gln Ala Val Tyr Trp Val Gly Pro
            210                 215                 220

Leu Leu Gly Gly Ala Thr Ala Ala Leu Val Tyr Asp Asn Val Val Val
225                 230                 235                 240

Pro Val Glu Asp Asp Arg Gly Ser Ser Thr Gly Asp Ala Ile Gly Val
                245                 250                 255

<210> SEQ ID NO 74
<211> LENGTH: 296
<212> TYPE: PRT
<213> ORGANISM: Arabidopsis thaliana

<400> SEQUENCE: 74

Met Ala Asp Ile Ser Gly Asn Gly Tyr Gly Asn Ala Arg Glu Glu Val
 1               5                  10                  15

Val Met Val Asn Leu Lys Asp Glu Val Glu His Gln Gln Glu Met Glu
                20                  25                  30

Asp Ile His Asn Pro Arg Pro Leu Lys Lys Gln Asp Ser Leu Leu Ser
             35                  40                  45

Val Ser Val Pro Phe Leu Gln Lys Leu Ile Ala Glu Phe Leu Gly Thr
 50                  55                  60

Tyr Phe Leu Val Phe Thr Gly Cys Ala Ser Val Val Asn Met Gln
 65                  70                  75                  80

Asn Asp Asn Val Val Thr Leu Pro Gly Ile Ala Ile Val Trp Gly Leu
                 85                  90                  95

Thr Ile Met Val Leu Ile Tyr Ser Leu Gly His Ile Ser Gly Ala His
            100                 105                 110

Ile Asn Pro Ala Val Thr Ile Ala Phe Ala Ser Cys Gly Arg Phe Pro
            115                 120                 125

Leu Lys Gln Val Pro Ala Tyr Val Ile Ser Gln Val Ile Gly Ser Thr
            130                 135                 140

Leu Ala Ala Ala Thr Leu Arg Leu Leu Phe Gly Leu Asp His Asp Val
145                 150                 155                 160

Cys Ser Gly Lys His Asp Val Phe Ile Gly Ser Ser Pro Val Gly Ser
                165                 170                 175
```

```
Asp Leu Gln Ala Phe Thr Met Glu Phe Ile Val Thr Phe Tyr Leu Met
            180                 185                 190

Phe Ile Ile Ser Gly Val Ala Thr Asp Asn Arg Ala Ile Gly Glu Leu
            195                 200                 205

Ala Gly Leu Ala Ile Gly Ser Thr Val Leu Leu Asn Val Leu Ile Ala
            210                 215                 220

Ala Pro Val Ser Ala Ser Met Asn Pro Gly Arg Ser Leu Gly Pro
225                 230                 235                 240

Ala Leu Val Tyr Gly Cys Tyr Lys Gly Ile Trp Ile Tyr Leu Val Ala
            245                 250                 255

Pro Thr Leu Gly Ala Ile Ala Gly Ala Trp Val Tyr Asn Thr Val Arg
            260                 265                 270

Tyr Thr Asp Lys Pro Leu Arg Glu Ile Thr Lys Ser Gly Ser Phe Leu
            275                 280                 285

Lys Thr Val Arg Ile Gly Ser Thr
            290                 295

<210> SEQ ID NO 75
<211> LENGTH: 294
<212> TYPE: PRT
<213> ORGANISM: Arabidopsis thaliana

<400> SEQUENCE: 75

Met Ala Glu Ile Ser Gly Asn Gly Gly Asp Ala Arg Asp Gly Ala Val
1               5                   10                  15

Val Val Asn Leu Lys Glu Glu Asp Glu Gln Gln Gln Gln Gln Gln Ala
            20                  25                  30

Ile His Lys Pro Leu Lys Lys Gln Asp Ser Leu Leu Ser Ile Ser Val
        35                  40                  45

Pro Phe Leu Gln Lys Leu Met Ala Glu Val Leu Gly Thr Tyr Phe Leu
    50                  55                  60

Ile Phe Ala Gly Cys Ala Ala Val Ala Val Asn Thr Gln His Asp Lys
65                  70                  75                  80

Ala Val Thr Leu Pro Gly Ile Ala Ile Val Trp Gly Leu Thr Val Met
            85                  90                  95

Val Leu Val Tyr Ser Leu Gly His Ile Ser Gly Ala His Phe Asn Pro
            100                 105                 110

Ala Val Thr Ile Ala Phe Ala Ser Cys Gly Arg Phe Pro Leu Lys Gln
        115                 120                 125

Val Pro Ala Tyr Val Ile Ser Gln Val Ile Gly Ser Thr Leu Ala Ala
    130                 135                 140

Ala Thr Leu Arg Leu Leu Phe Gly Leu Asp Gln Asp Val Cys Ser Gly
145                 150                 155                 160

Lys His Asp Val Phe Val Gly Thr Leu Pro Ser Gly Ser Asn Leu Gln
            165                 170                 175

Ser Phe Val Ile Glu Phe Ile Ile Thr Phe Tyr Leu Met Phe Val Ile
            180                 185                 190

Ser Gly Val Ala Thr Asp Asn Arg Ala Ile Gly Glu Leu Ala Gly Leu
        195                 200                 205

Ala Val Gly Ser Thr Val Leu Leu Asn Val Ile Ala Gly Pro Val
    210                 215                 220

Ser Gly Ala Ser Met Asn Pro Gly Arg Ser Leu Gly Pro Ala Met Val
225                 230                 235                 240

Tyr Ser Cys Tyr Arg Gly Leu Trp Ile Tyr Ile Val Ser Pro Ile Val
            245                 250                 255
```

Gly Ala Val Ser Gly Ala Trp Val Tyr Asn Met Val Arg Tyr Thr Asp
            260                 265                 270

Lys Pro Leu Arg Glu Ile Thr Lys Ser Gly Ser Phe Leu Lys Thr Val
        275                 280                 285

Arg Asn Gly Ser Ser Arg
    290

<210> SEQ ID NO 76
<211> LENGTH: 288
<212> TYPE: PRT
<213> ORGANISM: Arabidopsis thaliana

<400> SEQUENCE: 76

Met Asp Asp Ile Ser Val Ser Lys Ser Asn His Gly Asn Val Val Val
1               5                   10                  15

Leu Asn Ile Lys Ala Ser Ser Leu Ala Asp Thr Ser Leu Pro Ser Asn
            20                  25                  30

Lys His Glu Ser Ser Pro Pro Leu Leu Ser Val His Phe Leu Gln
        35                  40                  45

Lys Leu Leu Ala Glu Leu Val Gly Thr Tyr Tyr Leu Ile Phe Ala Gly
    50                  55                  60

Cys Ala Ala Ile Ala Val Asn Ala Gln His Asn His Val Val Thr Leu
65                  70                  75                  80

Val Gly Ile Ala Val Val Trp Gly Ile Val Ile Met Val Leu Val Tyr
                85                  90                  95

Cys Leu Gly His Leu Ser Ala His Phe Asn Pro Ala Val Thr Leu Ala
            100                 105                 110

Leu Ala Ser Ser Gln Arg Phe Pro Leu Asn Gln Val Pro Ala Tyr Ile
        115                 120                 125

Thr Val Gln Val Ile Gly Ser Thr Leu Ala Ser Ala Thr Leu Arg Leu
    130                 135                 140

Leu Phe Asp Leu Asn Asn Asp Val Cys Ser Lys Lys His Asp Val Phe
145                 150                 155                 160

Leu Gly Ser Ser Pro Ser Gly Ser Asp Leu Gln Ala Phe Val Met Glu
                165                 170                 175

Phe Ile Ile Thr Gly Phe Leu Met Leu Val Val Cys Ala Val Thr Thr
            180                 185                 190

Thr Lys Arg Thr Thr Glu Glu Leu Glu Gly Leu Ile Ile Gly Ala Thr
        195                 200                 205

Val Thr Leu Asn Val Ile Phe Ala Gly Glu Val Ser Gly Ala Ser Met
    210                 215                 220

Asn Pro Ala Arg Ser Ile Gly Pro Ala Leu Val Trp Gly Cys Tyr Lys
225                 230                 235                 240

Gly Ile Trp Ile Tyr Leu Leu Ala Pro Thr Leu Gly Ala Val Ser Gly
                245                 250                 255

Ala Leu Ile His Lys Met Leu Pro Ser Ile Gln Asn Ala Glu Pro Glu
            260                 265                 270

Phe Ser Lys Thr Gly Ser Ser His Lys Arg Val Thr Asp Leu Pro Leu
        275                 280                 285

<210> SEQ ID NO 77
<211> LENGTH: 323
<212> TYPE: PRT
<213> ORGANISM: Arabidopsis thaliana

<400> SEQUENCE: 77

```
Met Ala Glu Ile Ser Asp Ile Thr Thr Gln Thr Gln Thr Val Val Leu
1               5                   10                  15

Asp Ile Glu Asn Tyr Gln Ser Ile Asp Asp Ser Arg Ser Ser Asp Leu
            20                  25                  30

Ser Ala Pro Leu Val Ser Val Ser Phe Val Gln Lys Leu Ile Gly Glu
        35                  40                  45

Phe Val Gly Thr Phe Thr Met Ile Phe Ala Gly Cys Ser Ala Ile Val
    50                  55                  60

Val Asn Glu Thr Tyr Gly Lys Pro Val Thr Leu Pro Gly Ile Ala Leu
65                  70                  75                  80

Val Trp Gly Leu Val Thr Val Met Ile Tyr Ser Ile Gly His Val
                85                  90                  95

Ser Gly Ala His Phe Asn Pro Ala Val Ser Ile Ala Phe Ala Ser Ser
                100                 105                 110

Lys Lys Phe Pro Phe Asn Gln Val Pro Gly Tyr Ile Ala Ala Gln Leu
            115                 120                 125

Leu Gly Ser Thr Leu Ala Ala Ala Val Leu Arg Leu Val Phe His Leu
    130                 135                 140

Asp Asp Asp Val Cys Ser Leu Lys Gly Asp Val Tyr Val Gly Thr Tyr
145                 150                 155                 160

Pro Ser Asn Ser Asn Thr Thr Ser Phe Val Met Glu Phe Ile Ala Thr
                165                 170                 175

Phe Asn Leu Met Phe Val Ile Ser Ala Val Ala Thr Asp Lys Arg Ala
            180                 185                 190

Thr Gly Ser Phe Ala Gly Ile Ala Ile Gly Ala Thr Ile Val Leu Asp
    195                 200                 205

Ile Leu Phe Ser Gly Pro Ile Ser Gly Ala Ser Met Asn Pro Ala Arg
210                 215                 220

Ser Leu Gly Pro Ala Leu Ile Trp Gly Cys Tyr Lys Asp Leu Trp Leu
225                 230                 235                 240

Tyr Ile Val Ser Pro Val Ile Gly Ala Leu Ser Gly Ala Trp Thr Tyr
                245                 250                 255

Gly Leu Leu Arg Ser Thr Lys Lys Ser Tyr Ser Glu Ile Ile Arg Pro
            260                 265                 270

Asn Cys Asn Lys Val Ser Ser Arg Asp Arg Gln Glu Ala Ser Gln Asp
            275                 280                 285

Glu Ile Cys Val Leu Arg Val Val Asp Pro Ala Asn Gln Asn Tyr Phe
            290                 295                 300

Ile Cys Ser Ser Pro Thr Asp Ile Asn Gly Lys Cys Asn Val Thr Cys
305                 310                 315                 320

Lys Leu Ala

<210> SEQ ID NO 78
<211> LENGTH: 282
<212> TYPE: PRT
<213> ORGANISM: Zea mays

<400> SEQUENCE: 78

Met Ala Gly Gly Gly Asp His Ser Gln Thr Asn Gly Gly His Val Asp
1               5                   10                  15

Gln Arg Ala Leu Glu Glu Gly Arg Lys Glu Glu Phe Ala Asp Gln Gly
            20                  25                  30

Cys Ala Ala Met Val Val Ser Val Pro Phe Ile Gln Lys Ile Ile Ala
            35                  40                  45

Glu Ile Phe Gly Thr Tyr Phe Leu Met Phe Ala Gly Cys Gly Ala Val
```

```
                 50                  55                  60
Thr Ile Asn Ala Ser Lys Asn Gly Gln Ile Thr Phe Pro Gly Val Ala
 65                  70                  75                  80

Ile Val Trp Gly Leu Ala Val Met Val Met Val Tyr Ala Val Gly His
                 85                  90                  95

Ile Ser Gly Ala His Phe Asn Pro Ala Val Thr Leu Ala Phe Ala Thr
                100                 105                 110

Ser Gly Arg Phe Pro Trp Arg Gln Leu Pro Ala Tyr Val Leu Ala Gln
                115                 120                 125

Met Leu Gly Ala Thr Leu Ala Ser Gly Thr Leu Arg Leu Met Phe Gly
                130                 135                 140

Gly Arg His Glu His Phe Pro Gly Thr Leu Pro Thr Gly Ser Glu Val
145                 150                 155                 160

Gln Ser Leu Val Ile Glu Ile Thr Thr Phe Tyr Leu Met Phe Val
                165                 170                 175

Ile Ser Gly Val Ala Thr Asp Asn Arg Ala Ile Gly Glu Leu Ala Gly
                180                 185                 190

Leu Ala Val Gly Ala Thr Ile Leu Leu Asn Val Leu Ile Ala Gly Pro
                195                 200                 205

Val Ser Gly Ala Ser Met Asn Pro Ala Arg Ser Val Gly Pro Ala Leu
210                 215                 220

Val Ser Gly Glu Tyr Thr Ser Ile Trp Val Tyr Val Val Gly Pro Val
225                 230                 235                 240

Val Gly Ala Val Ala Gly Ala Trp Ala Tyr Asn Leu Ile Arg Phe Thr
                245                 250                 255

Asn Lys Pro Leu Arg Glu Ile Thr Lys Ser Thr Ser Phe Leu Lys Ser
                260                 265                 270

Thr Ser Arg Met Asn Ser Ala Ala Ser Ala
                275                 280

<210> SEQ ID NO 79
<211> LENGTH: 294
<212> TYPE: PRT
<213> ORGANISM: Zea mays

<400> SEQUENCE: 79

Met Ala Ala Ala Ser Thr Thr Ser Arg Thr Asn Ser Arg Val Asn Tyr
 1               5                  10                  15

Ser Asn Glu Ile His Asp Leu Ser Thr Val Gln Ser Gly Ser Val Val
                20                  25                  30

Pro Thr Leu Phe Tyr Pro Asp Lys Ser Ile Ala Asp Ile Phe Pro Pro
                35                  40                  45

His Leu Gly Lys Lys Val Ile Ser Glu Val Val Ala Thr Phe Leu Leu
                50                  55                  60

Val Phe Val Thr Cys Gly Ala Ala Ser Ile Tyr Gly Glu Asp Asn Arg
 65                  70                  75                  80

Arg Ile Ser Gln Leu Gly Gln Ser Val Ala Gly Gly Leu Ile Val Thr
                85                  90                  95

Val Met Ile Tyr Ala Thr Gly His Ile Ser Gly Ala His Met Asn Pro
                100                 105                 110

Ala Val Thr Leu Ser Phe Ala Cys Phe Arg His Phe Pro Trp Ile Gln
                115                 120                 125

Val Pro Phe Tyr Trp Ala Ala Gln Phe Thr Gly Ala Met Cys Ala Ala
                130                 135                 140

Phe Val Leu Lys Ala Val Leu His Pro Ile Ala Val Ile Gly Thr Thr
```

```
                145                 150                 155                 160
Thr Pro Ser Gly Pro His Trp His Ala Leu Leu Ile Glu Ile Val Val
            165                 170                 175

Thr Phe Asn Met Met Phe Val Thr Cys Ala Val Ala Thr Asp Ser Arg
            180                 185                 190

Ala Val Gly Glu Leu Ala Gly Leu Ala Val Gly Ser Ala Val Cys Ile
            195                 200                 205

Thr Ser Ile Phe Ala Gly Pro Val Ser Gly Gly Ser Met Asn Pro Ala
210                 215                 220

Arg Thr Leu Ala Pro Ala Val Ala Ser Asn Val Phe Thr Gly Leu Trp
225                 230                 235                 240

Ile Tyr Phe Leu Gly Pro Val Ile Gly Thr Leu Ser Gly Ala Trp Val
            245                 250                 255

Tyr Thr Tyr Ile Arg Phe Glu Glu Ala Pro Ala Ala Lys Asp Thr Gln
            260                 265                 270

Arg Leu Ser Ser Phe Lys Leu Arg Arg Met Gln Ser Gln Leu Ala Ala
            275                 280                 285

Asp Glu Phe Asp Thr Val
    290

<210> SEQ ID NO 80
<211> LENGTH: 301
<212> TYPE: PRT
<213> ORGANISM: Zea mays

<400> SEQUENCE: 80

Met Ala Ala Ser Thr Thr Ser Arg Thr Asn Ser Arg Val Asn Tyr Ser
1               5                   10                  15

Asn Glu Ile His Asp Leu Ser Thr Val Gln Gly Gly Ser Ala Ala Ala
            20                  25                  30

Ala Ala Ala Ala Leu Phe Tyr Pro Asp Ser Lys Ser Ile Ala Asp Ile
            35                  40                  45

Phe Pro Pro His Leu Gly Lys Lys Val Ile Ser Glu Val Val Ala Thr
50                  55                  60

Phe Leu Leu Val Phe Val Thr Cys Gly Ala Ala Ser Ile Tyr Gly Glu
65                  70                  75                  80

Asp Asn Ala Arg Ile Ser Gln Leu Gly Gln Ser Val Ala Gly Gly Leu
            85                  90                  95

Ile Val Thr Val Met Ile Tyr Ala Thr Gly His Ile Ser Gly Ala His
            100                 105                 110

Met Asn Pro Ala Val Thr Leu Ser Phe Ala Cys Phe Arg His Phe Pro
            115                 120                 125

Trp Ile Gln Val Pro Phe Tyr Trp Ala Ala Gln Phe Thr Gly Ala Met
            130                 135                 140

Cys Ala Ala Phe Val Leu Lys Ala Val Leu Gln Pro Ile Ala Val Ile
145                 150                 155                 160

Gly Thr Thr Thr Pro Ser Gly Pro His Trp His Ala Leu Ala Ile Glu
            165                 170                 175

Ile Val Val Thr Phe Asn Met Met Phe Val Thr Cys Ala Val Ala Thr
            180                 185                 190

Asp Ser Arg Ala Val Gly Glu Leu Ala Gly Leu Ala Val Gly Ser Ala
            195                 200                 205

Val Cys Ile Thr Ser Ile Phe Ala Gly Pro Val Ser Gly Gly Ser Met
210                 215                 220

Asn Pro Ala Arg Thr Leu Ala Pro Ala Val Ala Ser Asn Val Phe Thr
```

-continued

```
                225                 230                 235                 240
Gly Leu Trp Ile Tyr Phe Leu Gly Pro Val Gly Thr Leu Ser Gly
                245                 250                 255
Ala Trp Val Tyr Thr Tyr Ile Arg Phe Glu Glu Ala Pro Ala Ala Ala
                260                 265                 270
Lys Pro Asp Thr Gln Arg Leu Ser Ser Phe Lys Leu Arg Arg Met Gln
            275                 280                 285
Ser Gln Ser Ala Leu Ala Ala Asp Glu Phe Asp Thr Val
            290                 295                 300

<210> SEQ ID NO 81
<211> LENGTH: 283
<212> TYPE: PRT
<213> ORGANISM: Arabidopsis thaliana

<400> SEQUENCE: 81

Met Ser Ser His Ser Asp Glu Ile Glu Glu Gln Ile Ser Arg Ile
1               5                   10                  15
Glu Lys Gly Lys Gly Lys Asp Cys Gln Gly Gly Ile Glu Thr Val Ile
                20                  25                  30
Cys Thr Ser Pro Ser Ile Val Cys Leu Thr Gln Lys Leu Ile Ala Glu
            35                  40                  45
Met Ile Gly Thr Tyr Phe Ile Val Phe Ser Gly Cys Gly Val Val Val
        50                  55                  60
Val Asn Val Leu Tyr Gly Gly Thr Ile Thr Phe Pro Gly Ile Cys Val
65                  70                  75                  80
Thr Trp Gly Leu Ile Val Met Val Met Ile Tyr Ser Thr Gly His Ile
                85                  90                  95
Ser Gly Ala His Phe Asn Pro Ala Val Thr Val Thr Phe Ala Ile Phe
                100                 105                 110
Arg Arg Phe Pro Trp His Gln Val Pro Leu Tyr Ile Gly Ala Gln Phe
            115                 120                 125
Ala Gly Ser Leu Leu Ala Ser Leu Thr Leu Arg Leu Met Phe Lys Val
        130                 135                 140
Thr Pro Glu Ala Phe Phe Gly Thr Thr Pro Ala Asp Ser Pro Ala Arg
145                 150                 155                 160
Ala Leu Val Ala Glu Ile Ile Ile Ser Phe Leu Leu Met Phe Val Ile
                165                 170                 175
Ser Gly Val Ala Thr Asp Asn Arg Ala Val Gly Glu Leu Ala Gly Ile
                180                 185                 190
Ala Val Gly Met Thr Ile Met Val Asn Val Phe Val Ala Gly Pro Ile
            195                 200                 205
Ser Gly Ala Ser Met Asn Pro Ala Arg Ser Leu Gly Pro Ala Leu Val
        210                 215                 220
Met Gly Val Tyr Lys His Ile Trp Val Tyr Ile Val Gly Pro Val Leu
225                 230                 235                 240
Gly Val Ile Ser Gly Gly Phe Val Tyr Asn Leu Ile Arg Phe Thr Asp
                245                 250                 255
Lys Pro Leu Arg Glu Leu Thr Lys Ser Ala Ser Phe Leu Arg Ala Val
            260                 265                 270
Ser Pro Ser His Lys Gly Ser Ser Lys Thr
        275                 280

<210> SEQ ID NO 82
<211> LENGTH: 283
<212> TYPE: PRT
```

<213> ORGANISM: Arabidopsis thaliana

<400> SEQUENCE: 82

```
Met Thr Ser His Gly Glu Glu Ile Glu Asp Glu Gln Ile Ser Arg Ile
1               5                   10                  15

Glu Lys Gly Asn Cys Lys Asp Ser Gln Gly Gly Met Glu Thr Ala Ile
            20                  25                  30

Cys Ser Ser Pro Ser Ile Val Cys Leu Thr Gln Lys Leu Ile Ala Glu
        35                  40                  45

Met Ile Gly Thr Tyr Phe Ile Ile Phe Ser Gly Cys Gly Val Val Val
    50                  55                  60

Val Asn Val Leu Tyr Gly Gly Thr Ile Thr Phe Pro Gly Ile Cys Val
65                  70                  75                  80

Thr Trp Gly Leu Ile Val Met Val Met Ile Tyr Ser Thr Gly His Ile
                85                  90                  95

Ser Gly Ala His Phe Asn Pro Ala Val Thr Val Thr Phe Ala Val Phe
            100                 105                 110

Arg Arg Phe Pro Trp Tyr Gln Val Pro Leu Tyr Ile Gly Ala Gln Leu
        115                 120                 125

Thr Gly Ser Leu Leu Ala Ser Leu Thr Leu Arg Leu Met Phe Asn Val
    130                 135                 140

Thr Pro Lys Ala Phe Phe Gly Thr Thr Pro Thr Asp Ser Ser Gly Gln
145                 150                 155                 160

Ala Leu Val Ala Glu Ile Ile Ile Ser Phe Leu Leu Met Phe Val Ile
                165                 170                 175

Ser Gly Val Ala Thr Asp Ser Arg Ala Thr Gly Glu Leu Ala Gly Ile
            180                 185                 190

Ala Val Gly Met Thr Ile Ile Leu Asn Val Phe Val Ala Gly Pro Ile
        195                 200                 205

Ser Gly Ala Ser Met Asn Pro Ala Arg Ser Leu Gly Pro Ala Ile Val
    210                 215                 220

Met Gly Arg Tyr Lys Gly Ile Trp Val Tyr Ile Val Gly Pro Phe Val
225                 230                 235                 240

Gly Ile Phe Ala Gly Gly Phe Val Tyr Asn Phe Met Arg Phe Thr Asp
                245                 250                 255

Lys Pro Leu Arg Glu Leu Thr Ser Ala Ser Phe Leu Arg Ser Val
            260                 265                 270

Ala Gln Lys Asp Asn Ala Ser Lys Ser Asp Gly
        275                 280
```

<210> SEQ ID NO 83
<211> LENGTH: 304
<212> TYPE: PRT
<213> ORGANISM: Arabidopsis thaliana

<400> SEQUENCE: 83

```
Met Ala Pro Pro Glu Ala Glu Val Gly Ala Val Met Val Met Ala Pro
1               5                   10                  15

Pro Thr Pro Gly Thr Pro Gly Thr Pro Gly Gly Pro Leu Ile Thr Gly
            20                  25                  30

Met Arg Val Asp Ser Met Ser Phe Asp His Arg Lys Pro Thr Pro Arg
        35                  40                  45

Cys Lys Cys Leu Pro Val Met Gly Ser Thr Trp Gly Gln His Asp Thr
    50                  55                  60

Cys Phe Thr Asp Phe Pro Ser Pro Asp Val Ser Leu Thr Arg Lys Leu
65                  70                  75                  80
```

```
Gly Ala Glu Phe Val Gly Thr Phe Ile Leu Ile Phe Thr Ala Thr Ala
                85                  90                  95

Gly Pro Ile Val Asn Gln Lys Tyr Asp Gly Ala Glu Thr Leu Ile Gly
            100                 105                 110

Asn Ala Ala Cys Ala Gly Leu Ala Val Met Ile Ile Leu Ser Thr
        115                 120                 125

Gly His Ile Ser Gly Ala His Leu Asn Pro Ser Leu Thr Ile Ala Phe
    130                 135                 140

Ala Ala Leu Arg His Phe Pro Trp Ala His Val Pro Ala Tyr Ile Ala
145                 150                 155                 160

Ala Gln Val Ser Ala Ser Ile Cys Ala Ser Phe Ala Leu Lys Gly Val
                165                 170                 175

Phe His Pro Phe Met Ser Gly Val Thr Ile Pro Ser Val Ser Leu
            180                 185                 190

Gly Gln Ala Phe Ala Leu Glu Phe Ile Thr Phe Ile Leu Leu Phe
        195                 200                 205

Val Val Thr Ala Val Ala Thr Asp Thr Arg Ala Val Gly Glu Leu Ala
210                 215                 220

Gly Ile Ala Val Gly Ala Thr Val Met Leu Asn Ile Leu Val Ala Gly
225                 230                 235                 240

Pro Ser Thr Gly Gly Ser Met Asn Pro Val Arg Thr Leu Gly Pro Ala
                245                 250                 255

Val Ala Ser Gly Asn Tyr Arg Ser Leu Trp Val Tyr Leu Val Ala Pro
            260                 265                 270

Thr Leu Gly Ala Ile Ser Gly Ala Ala Val Tyr Thr Gly Val Lys Leu
        275                 280                 285

Asn Asp Ser Val Thr Asp Pro Pro Arg Pro Val Arg Ser Phe Arg Arg
290                 295                 300

<210> SEQ ID NO 84
<211> LENGTH: 305
<212> TYPE: PRT
<213> ORGANISM: Arabidopsis thaliana

<400> SEQUENCE: 84

Met Asp His Glu Glu Ile Pro Ser Thr Pro Ser Thr Pro Ala Thr Thr
1               5                   10                  15

Pro Gly Thr Pro Gly Ala Pro Leu Phe Gly Gly Phe Glu Gly Lys Arg
            20                  25                  30

Asn Gly His Asn Gly Arg Tyr Thr Pro Lys Ser Leu Leu Lys Ser Cys
        35                  40                  45

Lys Cys Phe Ser Val Asp Asn Glu Trp Ala Leu Glu Asp Gly Arg Leu
    50                  55                  60

Pro Pro Val Thr Cys Ser Leu Pro Pro Asn Val Ser Leu Tyr Arg
65                  70                  75                  80

Lys Leu Gly Ala Glu Phe Val Gly Thr Leu Ile Leu Ile Phe Ala Gly
                85                  90                  95

Thr Ala Thr Ala Ile Val Asn Gln Lys Thr Asp Gly Ala Glu Thr Leu
            100                 105                 110

Ile Gly Cys Ala Ala Ser Ala Gly Leu Ala Val Met Ile Val Ile Leu
        115                 120                 125

Ser Thr Gly His Ile Ser Gly Ala His Leu Asn Pro Ala Val Thr Ile
    130                 135                 140

Ala Phe Ala Ala Leu Lys His Phe Pro Trp Lys His Val Pro Val Tyr
145                 150                 155                 160
```

```
Ile Gly Ala Gln Val Met Ala Ser Val Ser Ala Ala Phe Ala Leu Lys
            165                 170                 175

Ala Val Phe Glu Pro Thr Met Ser Gly Gly Val Thr Val Pro Thr Val
        180                 185                 190

Gly Leu Ser Gln Ala Phe Ala Leu Glu Phe Ile Ile Ser Phe Asn Leu
            195                 200                 205

Met Phe Val Val Thr Ala Val Ala Thr Asp Thr Arg Ala Val Gly Glu
210                 215                 220

Leu Ala Gly Ile Ala Val Gly Ala Thr Val Met Leu Asn Ile Leu Ile
225                 230                 235                 240

Ala Gly Pro Ala Thr Ser Ala Ser Met Asn Pro Val Arg Thr Leu Gly
                245                 250                 255

Pro Ala Ile Ala Ala Asn Asn Tyr Arg Ala Ile Trp Val Tyr Leu Thr
            260                 265                 270

Ala Pro Ile Leu Gly Ala Leu Ile Gly Ala Gly Thr Tyr Thr Ile Val
        275                 280                 285

Lys Leu Pro Glu Glu Asp Glu Ala Pro Lys Glu Arg Arg Ser Phe Arg
    290                 295                 300

Arg
305

<210> SEQ ID NO 85
<211> LENGTH: 275
<212> TYPE: PRT
<213> ORGANISM: Arabidopsis thaliana

<400> SEQUENCE: 85

Met Asn Gly Glu Ala Arg Ser Arg Val Val Asp Gln Glu Ala Gly Ser
1               5                   10                  15

Thr Pro Ser Thr Leu Arg Asp Glu Asp His Pro Ser Arg Gln Arg Leu
            20                  25                  30

Phe Gly Cys Leu Pro Tyr Asp Ile Asp Leu Asn Pro Leu Arg Ile Val
        35                  40                  45

Met Ala Glu Leu Val Gly Thr Phe Ile Leu Met Phe Ser Val Cys Gly
    50                  55                  60

Val Ile Ser Ser Thr Gln Leu Ser Gly Gly His Val Gly Leu Leu Glu
65                  70                  75                  80

Tyr Ala Val Thr Ala Gly Leu Ser Val Val Val Val Tyr Ser Ile
                85                  90                  95

Gly His Ile Ser Gly Ala His Leu Asn Pro Ser Ile Thr Ile Ala Phe
            100                 105                 110

Ala Val Phe Gly Gly Phe Pro Trp Ser Gln Val Pro Leu Tyr Ile Thr
        115                 120                 125

Ala Gln Thr Leu Gly Ala Thr Ala Ala Thr Leu Val Gly Val Ser Val
    130                 135                 140

Tyr Gly Val Asn Ala Asp Ile Met Ala Thr Lys Pro Ala Leu Ser Cys
145                 150                 155                 160

Val Ser Ala Phe Phe Val Glu Leu Ile Ala Thr Ser Ile Val Val Phe
                165                 170                 175

Leu Ala Ser Ala Leu His Cys Gly Pro His Gln Asn Leu Gly Asn Leu
            180                 185                 190

Thr Gly Phe Val Ile Gly Thr Val Ser Leu Gly Val Leu Ile Thr
        195                 200                 205

Gly Pro Ile Ser Gly Gly Ser Met Asn Pro Ala Arg Ser Leu Gly Pro
    210                 215                 220
```

```
Ala Val Val Ala Trp Asp Phe Glu Asp Leu Trp Ile Tyr Met Thr Ala
225                 230                 235                 240

Pro Val Ile Gly Ala Ile Ile Gly Val Leu Thr Tyr Arg Ser Ile Ser
            245                 250                 255

Leu Lys Thr Arg Pro Cys Pro Ser Pro Val Ser Pro Ser Val Ser Ser
            260                 265                 270

Leu Leu Arg
        275

<210> SEQ ID NO 86
<211> LENGTH: 302
<212> TYPE: PRT
<213> ORGANISM: Zea mays

<400> SEQUENCE: 86

Met Glu Pro Gly Ser Thr Pro Pro Asn Gly Ser Ala Pro Ala Thr Pro
1               5                   10                  15

Gly Thr Pro Ala Pro Leu Phe Ser Ser Gly Gly Pro Arg Val Asp Ser
            20                  25                  30

Leu Ser Tyr Glu Arg Lys Ser Met Pro Arg Cys Lys Cys Leu Pro Leu
        35                  40                  45

Pro Ala Val Glu Gly Trp Gly Val Ala His Thr Cys Val Val Glu
50                  55                  60

Ile Pro Ala Pro Asp Val Ser Leu Thr Arg Lys Leu Gly Ala Glu Phe
65                  70                  75                  80

Val Gly Thr Phe Ile Leu Ile Phe Phe Ala Thr Ala Ala Pro Ile Val
                85                  90                  95

Asn Gln Lys Tyr Gly Gly Ala Ile Ser Pro Phe Gly Asn Ala Ala Cys
            100                 105                 110

Ala Gly Leu Ala Val Ala Thr Val Ile Leu Ser Thr Gly His Ile Ser
        115                 120                 125

Gly Ala His Leu Asn Pro Ser Leu Thr Ile Ala Phe Ala Ala Leu Arg
    130                 135                 140

His Phe Pro Trp Leu Gln Val Pro Ala Tyr Val Ala Val Gln Ala Leu
145                 150                 155                 160

Ala Ser Val Cys Ala Ala Phe Ala Leu Lys Gly Val Phe His Pro Phe
                165                 170                 175

Leu Ser Gly Gly Val Thr Val Pro Asp Ala Thr Val Ser Thr Ala Gln
            180                 185                 190

Ala Phe Phe Thr Glu Phe Ile Ile Ser Phe Asn Leu Leu Phe Val Val
        195                 200                 205

Thr Ala Val Ala Thr Asp Thr Arg Ala Val Gly Glu Leu Ala Gly Ile
    210                 215                 220

Ala Val Gly Ala Ala Val Thr Leu Asn Ile Leu Val Ala Gly Pro Thr
225                 230                 235                 240

Thr Gly Gly Ser Met Asn Pro Val Arg Thr Leu Gly Pro Ala Val Ala
                245                 250                 255

Ala Gly Asn Tyr Arg Gln Leu Trp Ile Tyr Leu Leu Ala Pro Thr Leu
            260                 265                 270

Gly Ala Leu Ala Gly Ala Ser Val Tyr Lys Ala Val Lys Leu Arg Asp
        275                 280                 285

Glu Asn Gly Glu Thr Pro Arg Thr Gln Arg Ser Phe Arg Arg
    290                 295                 300

<210> SEQ ID NO 87
```

```
<211> LENGTH: 240
<212> TYPE: PRT
<213> ORGANISM: Arabidopsis thaliana

<400> SEQUENCE: 87

Met Met Gly Val Leu Lys Ser Ala Ile Gly Asp Met Leu Met Thr Phe
1               5                   10                  15

Ser Trp Val Val Leu Ser Ala Thr Phe Gly Ile Gln Thr Ala Ala Ile
                20                  25                  30

Ile Ser Ala Gly Asp Phe Gln Ala Ile Thr Trp Ala Pro Leu Val Ile
            35                  40                  45

Leu Thr Ser Leu Ile Phe Val Tyr Val Ser Ile Phe Thr Val Ile Phe
    50                  55                  60

Gly Ser Ala Ser Phe Asn Pro Thr Gly Ser Ala Ala Phe Tyr Val Ala
65                  70                  75                  80

Gly Val Pro Gly Asp Thr Leu Phe Ser Leu Ala Ile Arg Leu Pro Ala
                85                  90                  95

Gln Ala Ile Gly Ala Ala Gly Ala Leu Ala Ile Met Glu Phe Ile
            100                 105                 110

Pro Glu Lys Tyr Lys His Met Ile Gly Pro Ser Leu Gln Val Asp
        115                 120                 125

Val His Thr Gly Ala Ile Ala Glu Thr Ile Leu Ser Phe Gly Ile Thr
130                 135                 140

Phe Ala Val Leu Leu Ile Ile Leu Arg Gly Pro Arg Arg Leu Leu Ala
145                 150                 155                 160

Lys Thr Phe Leu Leu Ala Leu Ala Thr Ile Ser Phe Val Val Ala Gly
                165                 170                 175

Ser Lys Tyr Thr Gly Pro Ala Met Asn Pro Ala Ile Ala Phe Gly Trp
            180                 185                 190

Ala Tyr Met Tyr Ser Ser His Asn Thr Trp Asp His Ile Tyr Val Tyr
        195                 200                 205

Trp Ile Ser Ser Phe Val Gly Ala Leu Ser Ala Ala Leu Leu Phe Arg
    210                 215                 220

Ser Ile Phe Pro Pro Pro Arg Pro Gln Lys Lys Gln Lys Ala
225                 230                 235                 240

<210> SEQ ID NO 88
<211> LENGTH: 243
<212> TYPE: PRT
<213> ORGANISM: Arabidopsis thaliana

<400> SEQUENCE: 88

Met Ser Ala Val Lys Ser Ala Leu Gly Asp Met Val Ile Thr Phe Leu
1               5                   10                  15

Trp Val Ile Leu Ser Ala Thr Phe Gly Ile Gln Thr Ala Ala Ile Val
                20                  25                  30

Ser Ala Val Gly Phe His Gly Ile Thr Trp Ala Pro Leu Val Ile Ser
            35                  40                  45

Thr Leu Val Val Phe Val Ser Ile Ser Ile Phe Thr Val Ile Gly Asn
    50                  55                  60

Val Leu Gly Gly Ala Ser Phe Asn Pro Cys Gly Asn Ala Ala Phe Tyr
65                  70                  75                  80

Thr Ala Gly Val Ser Ser Asp Ser Leu Phe Ser Leu Ala Ile Arg Ser
                85                  90                  95

Pro Ala Gln Ala Ile Gly Ala Ala Gly Ala Ile Thr Ile Met Glu
            100                 105                 110
```

```
Met Ile Pro Glu Lys Tyr Lys Thr Arg Ile Gly Gly Lys Pro Ser Leu
    115                 120                 125

Gln Phe Gly Ala His Asn Gly Ala Ile Ser Glu Val Val Leu Ser Phe
    130                 135                 140

Ser Val Thr Phe Leu Val Leu Ile Ile Leu Arg Gly Pro Arg Lys
145                 150                 155                 160

Leu Leu Ala Lys Thr Phe Leu Leu Ala Leu Ala Thr Val Ser Val Phe
                165                 170                 175

Val Val Gly Ser Lys Phe Thr Arg Pro Phe Met Asn Pro Ala Ile Ala
                180                 185                 190

Phe Gly Trp Ala Tyr Ile Tyr Lys Ser His Asn Thr Trp Asp His Phe
            195                 200                 205

Tyr Val Tyr Trp Ile Ser Ser Tyr Thr Gly Ala Ile Leu Ser Ala Met
    210                 215                 220

Leu Phe Arg Ile Ile Phe Pro Ala Pro Pro Leu Val Gln Lys Lys Gln
225                 230                 235                 240

Lys Lys Ala
```

<210> SEQ ID NO 89
<211> LENGTH: 245
<212> TYPE: PRT
<213> ORGANISM: Zea mays

<400> SEQUENCE: 89

```
Met Ala Met Gly Ala Thr Val Arg Ala Ala Ala Asp Ala Val Val
1               5                   10                  15

Thr Phe Leu Trp Val Leu Cys Ala Ser Ala Leu Gly Ala Ser Thr Ala
                20                  25                  30

Ala Val Thr Ser Tyr Leu Gly Val Gln Glu Gly Ala Gly His Tyr Ala
            35                  40                  45

Leu Leu Val Thr Thr Ser Leu Leu Ser Val Leu Leu Phe Thr Phe Asp
    50                  55                  60

Leu Leu Cys Gly Ala Leu Gly Gly Ala Ser Phe Asn Pro Thr Asp Phe
65                  70                  75                  80

Ala Ala Ser Tyr Ala Ala Gly Leu Asp Ser Pro Ser Leu Phe Ser Val
                85                  90                  95

Ala Leu Arg Phe Pro Ala Gln Ala Ala Gly Ala Val Gly Gly Ala Leu
            100                 105                 110

Ala Ile Ser Glu Leu Met Pro Ala Gln Tyr Lys His Thr Leu Ala Gly
    115                 120                 125

Pro Ser Leu Lys Val Asp Pro His Thr Gly Ala Leu Ala Glu Gly Val
130                 135                 140

Leu Thr Phe Val Ile Thr Leu Thr Val Leu Trp Val Ile Val Lys Gly
145                 150                 155                 160

Pro Arg Asn Val Ile Leu Lys Thr Leu Leu Leu Ser Thr Ser Ile Val
                165                 170                 175

Ser Val Ile Leu Ala Gly Ala Glu Tyr Thr Gly Pro Ser Met Asn Pro
            180                 185                 190

Ala Asn Ala Phe Gly Trp Ala Tyr Val Asn Asn Trp His Asn Thr Trp
    195                 200                 205

Glu Gln Leu Tyr Val Tyr Trp Ile Cys Pro Phe Ile Gly Ala Met Leu
    210                 215                 220

Ala Gly Trp Ile Phe Arg Val Val Phe Leu Pro Pro Ala Pro Lys Pro
225                 230                 235                 240

Lys Thr Lys Lys Ala
```

-continued

```
<210> SEQ ID NO 90
<211> LENGTH: 243
<212> TYPE: PRT
<213> ORGANISM: Zea mays

<400> SEQUENCE: 90

Met Ala Met Gly Glu Ala Leu Arg Ala Ala Ala Asp Ala Val Val
1               5                   10                  15

Thr Phe Leu Trp Val Leu Cys Val Ser Thr Leu Gly Ala Ser Thr Thr
                20                  25                  30

Ala Val Thr Ser Tyr Leu Arg Leu Gln Gly Val His Phe Ala Leu Leu
                35                  40                  45

Val Thr Val Ser Leu Leu Ser Val Leu Leu Phe Val Phe Asn Ile Leu
            50                  55                  60

Cys Asp Ala Leu Gly Gly Ala Ser Phe Asn Pro Thr Gly Val Ala Ala
65                  70                  75                  80

Phe Tyr Ala Ala Gly Val Thr Ser Pro Ser Leu Phe Ser Ile Ala Leu
                    85                  90                  95

Arg Leu Pro Ala Gln Ala Ala Gly Ala Val Gly Gly Ala Leu Ala Ile
                100                 105                 110

Ser Glu Leu Met Pro Ala Gln Tyr Arg His Met Leu Gly Gly Pro Ser
            115                 120                 125

Leu Lys Val Asp Pro His Thr Gly Ala Gly Ala Glu Leu Val Leu Thr
130                 135                 140

Phe Val Ile Thr Leu Ala Val Leu Leu Ile Ile Val Lys Gly Pro Arg
145                 150                 155                 160

Asn Pro Ile Ile Lys Thr Trp Met Ile Ser Ile Cys Thr Leu Cys Leu
                165                 170                 175

Val Leu Ser Gly Ala Ala Tyr Thr Gly Pro Ser Met Asn Pro Ala Asn
            180                 185                 190

Ala Phe Gly Trp Ala Tyr Val Asn Asn Arg His Asn Thr Trp Glu Gln
        195                 200                 205

Phe Tyr Val Tyr Trp Ile Cys Pro Phe Ile Gly Ala Ile Leu Ala Ala
    210                 215                 220

Trp Ile Phe Arg Ala Met Phe Leu Thr Pro Pro Pro Lys Pro Lys Ala
225                 230                 235                 240

Lys Lys Ala

<210> SEQ ID NO 91
<211> LENGTH: 237
<212> TYPE: PRT
<213> ORGANISM: Arabidopsis thaliana

<400> SEQUENCE: 91

Met Gly Arg Ile Gly Leu Val Val Thr Asp Leu Val Leu Ser Phe Met
1               5                   10                  15

Trp Ile Trp Ala Gly Val Leu Val Asn Ile Leu Val His Gly Val Leu
                20                  25                  30

Gly Phe Ser Arg Thr Asp Pro Ser Gly Glu Ile Val Arg Tyr Leu Phe
            35                  40                  45

Ser Ile Ile Ser Met Phe Ile Phe Ala Tyr Leu Gln Gln Ala Thr Lys
        50                  55                  60

Gly Gly Leu Tyr Asn Pro Leu Thr Ala Leu Ala Ala Gly Val Ser Gly
65                  70                  75                  80
```

-continued

```
Gly Phe Ser Ser Phe Ile Phe Ser Val Phe Val Arg Ile Pro Val Glu
             85              90              95

Val Ile Gly Ser Ile Leu Ala Val Lys His Ile Ile His Val Phe Pro
             100             105             110

Glu Ile Gly Lys Gly Pro Lys Leu Asn Val Ala Ile His His Gly Ala
             115             120             125

Leu Thr Glu Gly Ile Leu Thr Phe Phe Ile Val Leu Leu Ser Met Gly
             130             135             140

Leu Thr Arg Lys Ile Pro Gly Ser Phe Phe Met Lys Thr Trp Ile Gly
145              150             155             160

Ser Leu Ala Lys Leu Thr Leu His Ile Leu Gly Ser Asp Leu Thr Gly
             165             170             175

Gly Cys Met Asn Pro Ala Ala Val Met Gly Trp Ala Tyr Ala Arg Gly
             180             185             190

Glu His Ile Thr Lys Glu His Leu Leu Val Tyr Trp Leu Gly Pro Val
             195             200             205

Lys Ala Thr Leu Leu Ala Val Trp Phe Phe Lys Val Val Phe Lys Pro
             210             215             220

Leu Thr Glu Glu Gln Glu Lys Pro Lys Ala Lys Ser Glu
225              230             235
```